United States Patent
Kirby et al.

(10) Patent No.: US 9,150,653 B2
(45) Date of Patent: *Oct. 6, 2015

(54) CD127 BINDING PROTEINS

(75) Inventors: Ian Kirby, Stevenage (GB); Alexander H. Taylor, King of Prussia, PA (US); Thomas Matthew Webb, Stevenage (GB); Yu Xue, King of Prussia, PA (US)

(73) Assignee: Glaxo Group Limited, Brentford, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/574,847

(22) PCT Filed: Jan. 26, 2011

(86) PCT No.: PCT/US2011/022507
§ 371 (c)(1),
(2), (4) Date: Jul. 24, 2012

(87) PCT Pub. No.: WO2011/094259
PCT Pub. Date: Aug. 4, 2011

(65) Prior Publication Data
US 2012/0282254 A1    Nov. 8, 2012

Related U.S. Application Data

(60) Provisional application No. 61/299,010, filed on Jan. 28, 2010.

(51) Int. Cl.
| | |
|---|---|
| *C07K 16/46* | (2006.01) |
| *A61K 39/395* | (2006.01) |
| *C07K 16/28* | (2006.01) |
| *A61P 37/06* | (2006.01) |
| *C12N 1/15* | (2006.01) |
| *C12N 15/62* | (2006.01) |
| *C12P 21/08* | (2006.01) |
| *A61K 39/00* | (2006.01) |

(52) U.S. Cl.
CPC ....... *C07K 16/2866* (2013.01); *A61K 2039/505* (2013.01); *C07K 2317/24* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 5,543,320 A | 8/1996 | Park et al. |
| 2002/0142359 A1 | 10/2002 | Copley et al. |
| 2003/0229208 A1 | 12/2003 | Queen et al. |
| 2005/0025763 A1 | 2/2005 | Williams et al. |
| 2007/0066798 A1 | 3/2007 | Schmitt et al. |
| 2008/0226621 A1 | 9/2008 | Fung et al. |
| 2009/0226442 A1 | 9/2009 | Huet et al. |
| 2010/0016556 A1 | 1/2010 | Carter et al. |
| 2010/0040616 A1 | 2/2010 | Leung et al. |

OTHER PUBLICATIONS

Paul, Fundamental Immunology, 3rd Edition, 1993, pp. 292-295.*
Casset et al (Biochemical and Biophysical Research Communications, 2003, 307:198-20.*
Rudikoff et al. (Proc Natl Acad Sci USA. 1982, vol. 79, p. 1979.*
Stedman's Online Dictionary: Meningitis.*
Stedman's Online Dictionary: multiple sclerosis.*
Stedman's Online Dictionary: myocardial infarction.*
Stedman's Online Dictionary: inflammatory bowel disease.*
Wang et al. Nuc. Acids Res. 1999; vol. 27, pp. 4609-4618.*
Kaufman et al Blood, 1999, vol. 94, pp. 3178-3184.*
Crystal, R. Science, 1995; vol. 270, pp. 404-410.*
Anderson, W. Nature, 1998, vol. 392, pp. 25-30.*

* cited by examiner

*Primary Examiner* — Bridget E Bunner
*Assistant Examiner* — Fozia Hamud
(74) *Attorney, Agent, or Firm* — Haiyan Chen; William R Majarian

(57) ABSTRACT

Antigen binding proteins which bind to human IL-7 receptor (CD127) are provided. The antigen binding proteins are typically antibodies, and are useful in the treatment of diseases or disorders in humans, particularly autoimmune diseases such as multiple sclerosis.

19 Claims, 4 Drawing Sheets

Figure 4A-D
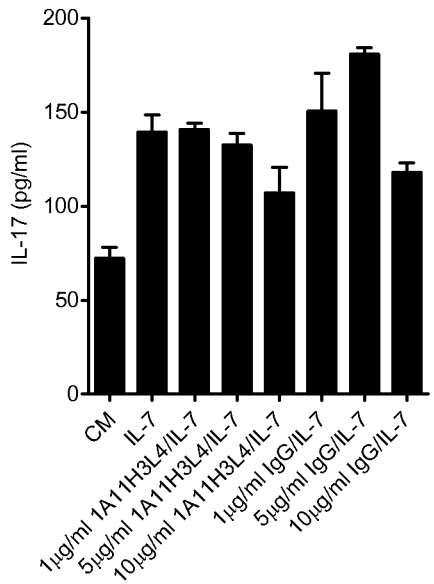
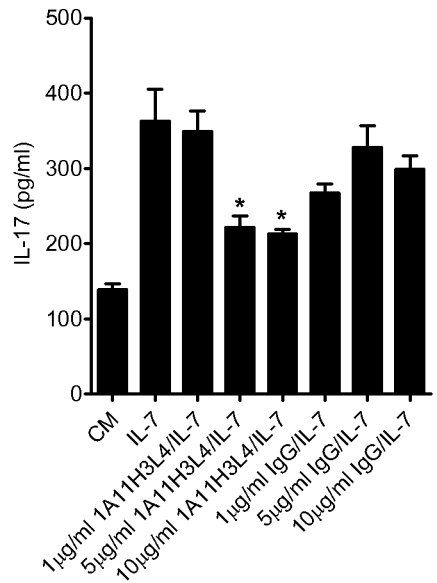
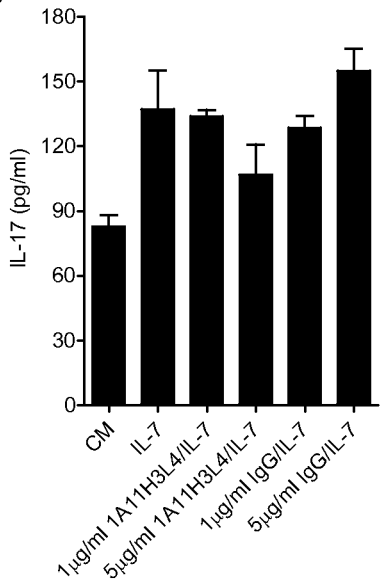
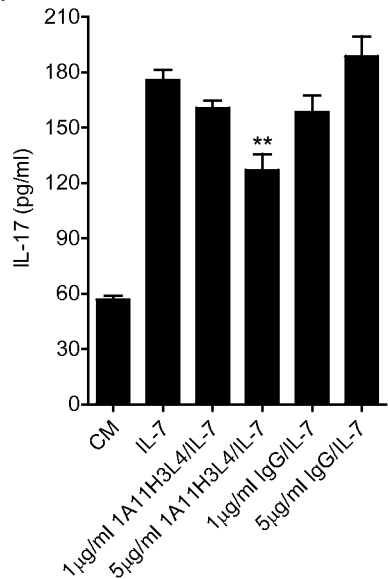

SEQUENCE LISTING

<160> NUMBER OF SEQ ID NOS: 138

<210> SEQ ID NO 1
<211> LENGTH: 455
<212> TYPE: PRT
<213> ORGANISM: Artificial Sequence
<220> FEATURE:
<223> OTHER INFORMATION: human CD127

<400> SEQUENCE: 1

Met Thr Ile Leu Gly Thr Thr Phe Gly Met Val Phe Ser Leu Leu Gln
1               5                   10                  15

Val Val Ser Gly Glu Ser Gly Tyr Ala Gln Asn Gly Asp Leu Glu Asp
                20                  25                  30

Ala Glu Leu Asp Asp Tyr Ser Phe Ser Cys Gln Leu Glu Val Asn Gly
            35                  40                  45

Ser Gln His Ser Leu Thr Cys Ala Phe Glu Asp Pro Asp Val Asn Thr
        50                  55                  60

Thr Asn Leu Glu Phe Glu Ile Cys Gly Ala Leu Val Glu Val Lys Cys
65                  70                  75                  80

Leu Asn Phe Arg Lys Leu Gln Glu Ile Tyr Phe Ile Glu Thr Lys Lys
                85                  90                  95

Phe Leu Leu Ile Gly Lys Ser Asn Ile Cys Val Lys Val Gly Glu Lys
            100                 105                 110

Ser Leu Thr Cys Lys Lys Ile Asp Leu Thr Thr Ile Val Lys Pro Glu
        115                 120                 125

Ala Pro Phe Asp Leu Ser Val Ile Tyr Arg Glu Gly Ala Asn Asp Phe
    130                 135                 140

Val Val Thr Phe Asn Thr Ser His Leu Gln Lys Lys Tyr Val Lys Val
145                 150                 155                 160

Leu Met His Asp Val Ala Tyr Arg Gln Glu Lys Asp Glu Asn Lys Trp
                165                 170                 175

Thr His Val Asn Leu Ser Ser Thr Lys Leu Thr Leu Leu Gln Arg Lys
            180                 185                 190

Leu Gln Pro Ala Ala Met Tyr Glu Ile Lys Val Arg Ser Ile Pro Asp
        195                 200                 205

His Tyr Phe Lys Gly Phe Trp Ser Glu Trp Ser Pro Ser Tyr Tyr Phe
    210                 215                 220

Arg Thr Pro Glu Ile Asn Asn Ser Ser Gly Glu Met Asp Pro Ile Leu
225                 230                 235                 240

Leu Thr Ile Ser Ile Leu Ser Phe Phe Ser Val Leu Val Ile Leu Ala
                245                 250                 255

Cys Val Leu Trp Lys Lys Arg Ile Lys Pro Ile Val Trp Pro Ser Leu
            260                 265                 270

Pro Asp His Lys Lys Thr Leu Glu His Leu Cys Lys Lys Pro Arg Lys
        275                 280                 285

Asn Leu Asn Val Ser Phe Asn Pro Glu Ser Phe Leu Asp Cys Gln Ile
    290                 295                 300

His Arg Val Asp Asp Ile Gln Ala Arg Asp Glu Val Glu Gly Phe Leu
305                 310                 315                 320

Gln Asp Thr Phe Pro Gln Gln Leu Glu Glu Ser Glu Lys Gln Arg Leu
                325                 330                 335

Gly Gly Asp Val Gln Ser Pro Asn Cys Pro Ser Glu Asp Val Val Val
            340                 345                 350

Thr Pro Glu Ser Phe Gly Arg Asp Ser Ser Leu Thr Cys Leu Ala Gly

```
                355                 360                 365
Asn Val Ser Ala Cys Asp Ala Pro Ile Leu Ser Ser Ser Arg Ser Leu
            370                 375                 380

Asp Cys Arg Glu Ser Gly Lys Asn Gly Pro His Val Tyr Gln Asp Leu
385                 390                 395                 400

Leu Leu Ser Leu Gly Thr Thr Asn Ser Thr Leu Pro Pro Pro Phe Ser
                405                 410                 415

Leu Gln Ser Gly Ile Leu Thr Leu Asn Pro Val Ala Gln Gly Gln Pro
            420                 425                 430

Ile Leu Thr Ser Leu Gly Ser Asn Gln Glu Glu Ala Tyr Val Thr Met
                435                 440                 445

Ser Ser Phe Tyr Gln Asn Gln
            450                 455

<210> SEQ ID NO 2
<211> LENGTH: 5
<212> TYPE: PRT
<213> ORGANISM: Mus musculus

<400> SEQUENCE: 2

Gly Tyr Thr Met Asn
1               5

<210> SEQ ID NO 3
<211> LENGTH: 17
<212> TYPE: PRT
<213> ORGANISM: Mus musculus

<400> SEQUENCE: 3

Leu Ile Asn Pro Tyr Asn Gly Val Thr Ser Tyr Asn Gln Lys Phe Lys
1               5                   10                  15

Gly

<210> SEQ ID NO 4
<211> LENGTH: 10
<212> TYPE: PRT
<213> ORGANISM: Mus musculus

<400> SEQUENCE: 4

Gly Asp Gly Asn Tyr Trp Tyr Phe Asp Val
1               5                   10

<210> SEQ ID NO 5
<211> LENGTH: 10
<212> TYPE: PRT
<213> ORGANISM: Mus musculus

<400> SEQUENCE: 5

Ser Ala Ser Ser Ser Val Thr Tyr Met His
1               5                   10

<210> SEQ ID NO 6
<211> LENGTH: 7
<212> TYPE: PRT
<213> ORGANISM: Mus musculus

<400> SEQUENCE: 6

Glu Ile Ser Lys Leu Ala Ser
1               5

<210> SEQ ID NO 7
```

```
<211> LENGTH: 8
<212> TYPE: PRT
<213> ORGANISM: Mus musculus

<400> SEQUENCE: 7

Gln Glu Trp Asn Tyr Pro Tyr Thr
 1               5

<210> SEQ ID NO 8
<211> LENGTH: 119
<212> TYPE: PRT
<213> ORGANISM: Mus musculus

<400> SEQUENCE: 8

Glu Val Gln Leu Gln Gln Ser Gly Pro Glu Leu Leu Lys Pro Gly Ala
 1               5                  10                  15

Ser Met Lys Ile Ser Cys Lys Ala Ser Gly Tyr Ser Phe Thr Gly Tyr
             20                  25                  30

Thr Met Asn Trp Val Lys Gln Ser His Gly Lys Asn Leu Glu Trp Ile
         35                  40                  45

Gly Leu Ile Asn Pro Tyr Asn Gly Val Thr Ser Tyr Asn Gln Lys Phe
     50                  55                  60

Lys Gly Lys Ala Thr Leu Thr Val Ala Lys Ser Ser Ser Thr Ala Tyr
 65                  70                  75                  80

Met Glu Leu Leu Ser Leu Thr Ser Glu Asp Ser Ala Val Tyr Tyr Cys
                 85                  90                  95

Ala Arg Gly Asp Gly Asn Tyr Trp Tyr Phe Asp Val Trp Gly Ala Gly
            100                 105                 110

Thr Thr Val Thr Val Ser Ser
        115

<210> SEQ ID NO 9
<211> LENGTH: 105
<212> TYPE: PRT
<213> ORGANISM: Mus musculus

<400> SEQUENCE: 9

Glu Ile Val Leu Thr Gln Ser Pro Ala Ile Thr Ala Ala Ser Leu Gly
 1               5                  10                  15

Gln Lys Val Thr Ile Thr Cys Ser Ala Ser Ser Ser Val Thr Tyr Met
             20                  25                  30

His Trp Tyr Gln Gln Lys Ser Gly Thr Ser Pro Lys Pro Trp Ile Tyr
         35                  40                  45

Glu Ile Ser Lys Leu Ala Ser Gly Val Pro Val Arg Phe Ser Gly Ser
     50                  55                  60

Gly Ser Gly Thr Ser Tyr Ser Leu Thr Ile Ser Ser Met Glu Ala Glu
 65                  70                  75                  80

Asp Ala Ala Ile Tyr Tyr Cys Gln Glu Trp Asn Tyr Pro Tyr Thr Phe
                 85                  90                  95

Gly Gly Gly Thr Lys Leu Glu Ile Lys
            100                 105

<210> SEQ ID NO 10
<211> LENGTH: 119
<212> TYPE: PRT
<213> ORGANISM: Artificial Sequence
<220> FEATURE:
<223> OTHER INFORMATION: 1A11.H0 VH

<400> SEQUENCE: 10
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Thr Met Asn Trp Val Arg Gln Ala Pro Gly Gln Gly Leu Glu Trp Met
            35                  40                  45

Gly Leu Ile Asn Pro Tyr Asn Gly Val Thr Ser Tyr Asn Gln Lys Phe
        50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Asp Gly Asn Tyr Trp Tyr Phe Asp Val Trp Gly Gln Gly
            100                 105                 110

Thr Thr Val Thr Val Ser Ser
        115

<210> SEQ ID NO 11
<211> LENGTH: 119
<212> TYPE: PRT
<213> ORGANISM: Artificial Sequence
<220> FEATURE:
<223> OTHER INFORMATION: 1A11.H1 VH

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Thr Met Asn Trp Val Arg Gln Ala Pro Gly Gln Gly Leu Glu Trp Met
            35                  40                  45

Gly Leu Ile Asn Pro Tyr Asn Gly Val Thr Ser Tyr Asn Gln Lys Phe
        50                  55                  60

Lys Gly Arg Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Asp Gly Asn Tyr Trp Tyr Phe Asp Val Trp Gly Gln Gly
            100                 105                 110

Thr Thr Val Thr Val Ser Ser
        115

<210> SEQ ID NO 12
<211> LENGTH: 119
<212> TYPE: PRT
<213> ORGANISM: Artificial Sequence
<220> FEATURE:
<223> OTHER INFORMATION: 1A11.H2 VH

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Thr Met Asn Trp Val Arg Gln Ala Pro Gly Gln Gly Leu Glu Trp Met
            35                  40                  45

Gly Leu Ile Asn Pro Tyr Asn Gly Val Thr Ser Tyr Asn Gln Lys Phe

```
                    50                  55                  60
Lys Gly Lys Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Gly Asp Gly Asn Tyr Trp Tyr Phe Asp Val Trp Gly Gln Gly
                100                 105                 110

Thr Thr Val Thr Val Ser Ser
            115

<210> SEQ ID NO 13
<211> LENGTH: 119
<212> TYPE: PRT
<213> ORGANISM: Artificial Sequence
<220> FEATURE:
<223> OTHER INFORMATION: 1A11.H3 VH

<400> SEQUENCE: 13

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Gly Tyr
                 20                  25                  30

Thr Met Asn Trp Val Arg Gln Ala Pro Gly Gln Gly Leu Glu Trp Met
             35                  40                  45

Gly Leu Ile Asn Pro Tyr Asn Gly Val Thr Ser Tyr Asn Gln Lys Phe
 50                  55                  60

Lys Gly Arg Val Thr Leu Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Gly Asp Gly Asn Tyr Trp Tyr Phe Asp Val Trp Gly Gln Gly
                100                 105                 110

Thr Thr Val Thr Val Ser Ser
            115

<210> SEQ ID NO 14
<211> LENGTH: 119
<212> TYPE: PRT
<213> ORGANISM: Artificial Sequence
<220> FEATURE:
<223> OTHER INFORMATION: 1A11.H4 VH

<400> SEQUENCE: 14

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Gly Tyr
                 20                  25                  30

Thr Met Asn Trp Val Arg Gln Ala Pro Gly Gln Gly Leu Glu Trp Met
             35                  40                  45

Gly Leu Ile Asn Pro Tyr Asn Gly Val Thr Ser Tyr Asn Gln Lys Phe
 50                  55                  60

Lys Gly Lys Val Thr Met Thr Val Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Gly Asp Gly Asn Tyr Trp Tyr Phe Asp Val Trp Gly Gln Gly
                100                 105                 110
```

Thr Thr Val Thr Val Ser Ser
        115

<210> SEQ ID NO 15
<211> LENGTH: 119
<212> TYPE: PRT
<213> ORGANISM: Artificial Sequence
<220> FEATURE:
<223> OTHER INFORMATION: 1A11.H5 VH

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Thr Met Asn Trp Val Arg Gln Ala Pro Gly Gln Gly Leu Glu Trp Met
        35                  40                  45

Gly Leu Ile Asn Pro Tyr Asn Gly Val Thr Ser Tyr Asn Gln Lys Phe
    50                  55                  60

Lys Gly Lys Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Asp Gly Asn Tyr Trp Tyr Phe Asp Val Trp Gly Gln Gly
            100                 105                 110

Thr Thr Val Thr Val Ser Ser
        115

<210> SEQ ID NO 16
<211> LENGTH: 119
<212> TYPE: PRT
<213> ORGANISM: Artificial Sequence
<220> FEATURE:
<223> OTHER INFORMATION: 1A11.H6 VH

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Thr Met Asn Trp Val Arg Gln Ala Pro Gly Gln Gly Leu Glu Trp Met
        35                  40                  45

Gly Leu Ile Asn Pro Tyr Asn Gly Val Thr Ser Tyr Asn Gln Lys Phe
    50                  55                  60

Lys Gly Lys Val Thr Leu Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Asp Gly Asn Tyr Trp Tyr Phe Asp Val Trp Gly Gln Gly
            100                 105                 110

Thr Thr Val Thr Val Ser Ser
        115

<210> SEQ ID NO 17
<211> LENGTH: 119
<212> TYPE: PRT
<213> ORGANISM: Artificial Sequence
<220> FEATURE:
<223> OTHER INFORMATION: 1A11.H7 VH

```
<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Thr Met Asn Trp Val Arg Gln Ala Pro Gly Gln Gly Leu Glu Trp Met
        35                  40                  45

Gly Leu Ile Asn Pro Tyr Asn Gly Val Thr Ser Tyr Asn Gln Lys Phe
    50                  55                  60

Lys Gly Lys Val Thr Leu Thr Val Ala Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Asp Gly Asn Tyr Trp Tyr Phe Asp Val Trp Gly Gln Gly
            100                 105                 110

Thr Thr Val Thr Val Ser Ser
        115

<210> SEQ ID NO 18
<211> LENGTH: 105
<212> TYPE: PRT
<213> ORGANISM: Artificial Sequence
<220> FEATURE:
<223> OTHER INFORMATION: 1A11.L0 Vk

<400> SEQUENCE: 18

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Thr Tyr Met
            20                  25                  30

His Trp Tyr Gln Gln Lys Pro Gly Gln Ala Pro Arg Leu Leu Ile Tyr
        35                  40                  45

Glu Ile Ser Lys Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Glu Trp Asn Tyr Pro Tyr Thr Phe
                85                  90                  95

Gly Gly Gly Thr Lys Val Glu Ile Lys
            100                 105

<210> SEQ ID NO 19
<211> LENGTH: 105
<212> TYPE: PRT
<213> ORGANISM: Artificial Sequence
<220> FEATURE:
<223> OTHER INFORMATION: 1A11.L1 Vk

<400> SEQUENCE: 19

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Thr Tyr Met
            20                  25                  30

His Trp Tyr Gln Gln Lys Pro Gly Gln Ala Pro Arg Leu Trp Ile Tyr
        35                  40                  45

Glu Ile Ser Lys Leu Ala Ser Gly Ile Pro Ala Arg Phe Ser Gly Ser
    50                  55                  60
```

-continued

```
Gly Ser Gly Thr Asp Phe Thr Leu Thr Ile Ser Ser Leu Glu Pro Glu
 65                  70                  75                  80

Asp Phe Ala Val Tyr Tyr Cys Gln Glu Trp Asn Tyr Pro Tyr Thr Phe
                 85                  90                  95

Gly Gly Gly Thr Lys Val Glu Ile Lys
            100                 105

<210> SEQ ID NO 20
<211> LENGTH: 105
<212> TYPE: PRT
<213> ORGANISM: Artificial Sequence
<220> FEATURE:
<223> OTHER INFORMATION: 1A11.L2 Vk

<400> SEQUENCE: 20

Glu Ile Val Leu Thr Gln Ser Pro Ala Thr Leu Ser Leu Ser Pro Gly
  1               5                  10                  15

Glu Arg Ala Thr Leu Ser Cys Ser Ala Ser Ser Ser Val Thr Tyr Met
                 20                  25                  30

His Trp Tyr Gln Gln Lys Pro Gly Gln Ala Pro Arg Leu Leu Ile Tyr
             35                  40                  45

Glu Ile Ser Lys Leu Ala Ser Gly Ile Pro Ala Arg Phe Ser Gly Ser
         50                  55                  60

Gly Ser Gly Thr Asp Tyr Thr Leu Thr Ile Ser Ser Leu Glu Pro Glu
 65                  70                  75                  80

Asp Phe Ala Val Tyr Tyr Cys Gln Glu Trp Asn Tyr Pro Tyr Thr Phe
                 85                  90                  95

Gly Gly Gly Thr Lys Val Glu Ile Lys
            100                 105

<210> SEQ ID NO 21
<211> LENGTH: 105
<212> TYPE: PRT
<213> ORGANISM: Artificial Sequence
<220> FEATURE:
<223> OTHER INFORMATION: 1A11.L3 Vk

<400> SEQUENCE: 21

Glu Ile Val Leu Thr Gln Ser Pro Ala Thr Leu Ser Leu Ser Pro Gly
  1               5                  10                  15

Glu Arg Ala Thr Leu Ser Cys Ser Ala Ser Ser Ser Val Thr Tyr Met
                 20                  25                  30

His Trp Tyr Gln Gln Lys Pro Gly Gln Ala Pro Arg Leu Trp Ile Tyr
             35                  40                  45

Glu Ile Ser Lys Leu Ala Ser Gly Ile Pro Ala Arg Phe Ser Gly Ser
         50                  55                  60

Gly Ser Gly Thr Asp Tyr Thr Leu Thr Ile Ser Ser Leu Glu Pro Glu
 65                  70                  75                  80

Asp Phe Ala Val Tyr Tyr Cys Gln Glu Trp Asn Tyr Pro Tyr Thr Phe
                 85                  90                  95

Gly Gly Gly Thr Lys Val Glu Ile Lys
            100                 105

<210> SEQ ID NO 22
<211> LENGTH: 105
<212> TYPE: PRT
<213> ORGANISM: Artificial Sequence
<220> FEATURE:
<223> OTHER INFORMATION: 1A11.L4 Vk
```

<400> SEQUENCE: 22

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Val Thr Tyr Met
            20                  25                  30

His Trp Tyr Gln Gln Lys Pro Gly Gln Ala Pro Arg Pro Leu Ile Tyr
            35                  40                  45

Glu Ile Ser Lys Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Glu Trp Asn Tyr Pro Tyr Thr Phe
                85                  90                  95

Gly Gly Gly Thr Lys Val Glu Ile Lys
            100                 105

<210> SEQ ID NO 23
<211> LENGTH: 105
<212> TYPE: PRT
<213> ORGANISM: Artificial Sequence
<220> FEATURE:
<223> OTHER INFORMATION: 1A11.L5 Vk

<400> SEQUENCE: 23

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Val Thr Tyr Met
            20                  25                  30

His Trp Tyr Gln Gln Lys Pro Gly Gln Ala Pro Arg Pro Trp Ile Tyr
            35                  40                  45

Glu Ile Ser Lys Leu Ala Ser Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Glu Trp Asn Tyr Pro Tyr Thr Phe
                85                  90                  95

Gly Gly Gly Thr Lys Val Glu Ile Lys
            100                 105

<210> SEQ ID NO 24
<211> LENGTH: 105
<212> TYPE: PRT
<213> ORGANISM: Artificial Sequence
<220> FEATURE:
<223> OTHER INFORMATION: 1A11.L6 Vk

<400> SEQUENCE: 24

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Val Thr Tyr Met
            20                  25                  30

His Trp Tyr Gln Gln Lys Pro Gly Gln Ala Pro Arg Pro Trp Ile Tyr
            35                  40                  45

Glu Ile Ser Lys Leu Ala Ser Gly Val Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

```
Asp Phe Ala Val Tyr Tyr Cys Gln Glu Trp Asn Tyr Pro Tyr Thr Phe
                85                  90                  95

Gly Gly Gly Thr Lys Val Glu Ile Lys
            100                 105

<210> SEQ ID NO 25
<211> LENGTH: 105
<212> TYPE: PRT
<213> ORGANISM: Artificial Sequence
<220> FEATURE:
<223> OTHER INFORMATION: 1A11.L7 Vk

<400> SEQUENCE: 25

Glu Ile Val Leu Thr Gln Ser Pro Ala Thr Leu Ser Leu Ser Pro Gly
 1               5                  10                  15

Glu Arg Ala Thr Leu Ser Cys Ser Ala Ser Ser Ser Val Thr Tyr Met
            20                  25                  30

His Trp Tyr Gln Gln Lys Pro Gly Gln Ala Pro Lys Pro Trp Ile Tyr
        35                  40                  45

Glu Ile Ser Lys Leu Ala Ser Gly Val Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Glu Trp Asn Tyr Pro Tyr Thr Phe
                85                  90                  95

Gly Gly Gly Thr Lys Val Glu Ile Lys
            100                 105

<210> SEQ ID NO 26
<211> LENGTH: 105
<212> TYPE: PRT
<213> ORGANISM: Artificial Sequence
<220> FEATURE:
<223> OTHER INFORMATION: 1A11.L8 Vk

<400> SEQUENCE: 26

Glu Ile Val Leu Thr Gln Ser Pro Ala Thr Leu Ser Leu Ser Pro Gly
 1               5                  10                  15

Glu Arg Ala Thr Leu Ser Cys Ser Ala Ser Ser Ser Val Thr Tyr Met
            20                  25                  30

His Trp Tyr Gln Gln Lys Pro Gly Gln Ala Pro Lys Pro Trp Ile Tyr
        35                  40                  45

Glu Ile Ser Lys Leu Ala Ser Gly Val Pro Ala Arg Phe Ser Gly Ser
    50                  55                  60

Gly Ser Gly Thr Ser Tyr Thr Leu Thr Ile Ser Ser Leu Glu Pro Glu
65                  70                  75                  80

Asp Phe Ala Val Tyr Tyr Cys Gln Glu Trp Asn Tyr Pro Tyr Thr Phe
                85                  90                  95

Gly Gly Gly Thr Lys Val Glu Ile Lys
            100                 105

<210> SEQ ID NO 27
<211> LENGTH: 105
<212> TYPE: PRT
<213> ORGANISM: Artificial Sequence
<220> FEATURE:
<223> OTHER INFORMATION: 1A11.L9 Vk

<400> SEQUENCE: 27

Glu Ile Val Leu Thr Gln Ser Pro Ala Thr Leu Ser Leu Ser Pro Gly
```

```
                1               5                  10                 15
            Glu Arg Ala Thr Leu Ser Cys Ser Ala Ser Ser Ser Val Thr Tyr Met
                              20                  25                 30

His Trp Tyr Gln Gln Lys Pro Gly Gln Ala Pro Lys Pro Trp Ile Tyr
                              35                  40                 45

Glu Ile Ser Lys Leu Ala Ser Gly Val Pro Val Arg Phe Ser Gly Ser
                              50                  55                 60

Gly Ser Gly Thr Ser Tyr Thr Leu Thr Ile Ser Ser Leu Glu Pro Glu
            65                70                  75                 80

Asp Phe Ala Val Tyr Tyr Cys Gln Glu Trp Asn Tyr Pro Tyr Thr Phe
                              85                  90                 95

Gly Gly Gly Thr Lys Val Glu Ile Lys
                              100                 105

<210> SEQ ID NO 28
<211> LENGTH: 119
<212> TYPE: PRT
<213> ORGANISM: Artificial Sequence
<220> FEATURE:
<223> OTHER INFORMATION: 1A11c VH

<400> SEQUENCE: 28

Glu Val Gln Leu Gln Gln Ser Gly Pro Glu Leu Leu Lys Pro Gly Ala
            1                 5                  10                 15

Ser Met Lys Ile Ser Cys Lys Ala Ser Gly Tyr Ser Phe Thr Gly Tyr
                              20                  25                 30

Thr Met Asn Trp Val Lys Gln Ser His Gly Lys Asn Leu Glu Trp Ile
                              35                  40                 45

Gly Leu Ile Asn Pro Tyr Asn Gly Val Thr Ser Tyr Asn Gln Lys Phe
                              50                  55                 60

Lys Gly Lys Ala Thr Leu Thr Val Ala Lys Ser Ser Ser Thr Ala Tyr
            65                70                  75                 80

Met Glu Leu Leu Ser Leu Thr Ser Glu Asp Ser Ala Val Tyr Tyr Cys
                              85                  90                 95

Ala Arg Gly Asp Gly Asn Tyr Trp Tyr Phe Asp Val Trp Gly Ala Gly
                              100                 105                110

Thr Thr Val Thr Val Ser Ser
                    115

<210> SEQ ID NO 29
<211> LENGTH: 105
<212> TYPE: PRT
<213> ORGANISM: Artificial Sequence
<220> FEATURE:
<223> OTHER INFORMATION: 1A11c Vk

<400> SEQUENCE: 29

Glu Ile Val Leu Thr Gln Ser Pro Ala Ile Thr Ala Ala Ser Leu Gly
            1                 5                  10                 15

Gln Lys Val Thr Ile Thr Cys Ser Ala Ser Ser Ser Val Thr Tyr Met
                              20                  25                 30

His Trp Tyr Gln Gln Lys Ser Gly Thr Ser Pro Lys Pro Trp Ile Tyr
                              35                  40                 45

Glu Ile Ser Lys Leu Ala Ser Gly Val Pro Val Arg Phe Ser Gly Ser
                              50                  55                 60

Gly Ser Gly Thr Ser Tyr Ser Leu Thr Ile Ser Ser Met Glu Ala Glu
            65                70                  75                 80
```

Asp Ala Ala Ile Tyr Tyr Cys Gln Glu Trp Asn Tyr Pro Tyr Thr Phe
            85                  90                  95

Gly Gly Gly Thr Lys Leu Glu Ile Lys
            100             105

<210> SEQ ID NO 30
<211> LENGTH: 357
<212> TYPE: DNA
<213> ORGANISM: Artificial Sequence
<220> FEATURE:
<223> OTHER INFORMATION: polynucleotide sequence encoding 1A11.H1 VH

<400> SEQUENCE: 30
caggtgcagc tggtgcagag cggagccgag gtgaagaaac ccggagccag cgtgaaggtg     60
agctgcaagg ccagcggcta caccttcacc ggctacacca tgaactgggt gaggcaggcc    120
cccggccagg gactcgagtg gatgggcctg atcaacccct acaacggcgt gaccagctac    180
aaccagaagt tcaagggcag ggtgaccatg accgtggata ccagcatcag caccgcttac    240
atggaactga gcaggctgag gtccgacgac accgccgtgt attactgcgc caggggcgac    300
ggcaactact ggtacttcga tgtgtggggc cagggcacca ccgtcacagt gagcagc      357

<210> SEQ ID NO 31
<211> LENGTH: 357
<212> TYPE: DNA
<213> ORGANISM: Artificial Sequence
<220> FEATURE:
<223> OTHER INFORMATION: polynucleotide sequence encoding 1A11.H2 VH

<400> SEQUENCE: 31
caggtgcagc tggtgcagag cggagccgag gtgaagaaac ccggagccag cgtgaaggtg     60
agctgcaagg ccagcggcta caccttcacc ggctacacca tgaactgggt gaggcaggcc    120
cccggccagg gactcgagtg gatgggcctg atcaacccct acaacggcgt gaccagctac    180
aaccagaagt tcaagggcaa ggtgaccatg accaggdata ccagcatcag caccgcttac    240
atggaactga gcaggctgag gtccgacgac accgccgtgt attactgcgc caggggcgac    300
ggcaactact ggtacttcga tgtgtggggc cagggcacca ccgtcacagt gagcagc      357

<210> SEQ ID NO 32
<211> LENGTH: 357
<212> TYPE: DNA
<213> ORGANISM: Artificial Sequence
<220> FEATURE:
<223> OTHER INFORMATION: polynucleotide sequence encoding 1A11.H3 VH

<400> SEQUENCE: 32
caggtgcagc tggtgcagag cggagccgag gtgaagaaac ccggagccag cgtgaaggtg     60
agctgcaagg ccagcggcta caccttcacc ggctacacca tgaactgggt gaggcaggcc    120
cccggccagg gactcgagtg gatgggcctg atcaacccct acaacggcgt gaccagctac    180
aaccagaagt tcaagggcag ggtgaccctg accaggdata ccagcatcag caccgcttac    240
atggaactga gcaggctgag gtccgacgac accgccgtgt attactgcgc caggggcgac    300
ggcaactact ggtacttcga tgtgtggggc cagggcacca ccgtcacagt gagcagc      357

<210> SEQ ID NO 33
<211> LENGTH: 357
<212> TYPE: DNA
<213> ORGANISM: Artificial Sequence
<220> FEATURE:
<223> OTHER INFORMATION: polynucleotide sequence encoding 1A11.H4 VH

<400> SEQUENCE: 33

```
caggtgcagc tggtgcagag cggagccgag gtgaagaaac ccggagccag cgtgaaggtg    60
agctgcaagg ccagcggcta caccttcacc ggctacacca tgaactgggt gaggcaggcc   120
cccggccagg gactcgagtg gatgggcctg atcaaccct acaacggcgt gaccagctac   180
aaccagaagt tcaagggcaa ggtgaccatg accgtggata ccagcatcag caccgcttac   240
atggaactga gcaggctgag gtccgacgac accgccgtgt attactgcgc caggggcgac   300
ggcaactact ggtacttcga tgtgtggggc cagggcacca ccgtcacagt gagcagc      357
```

<210> SEQ ID NO 34
<211> LENGTH: 357
<212> TYPE: DNA
<213> ORGANISM: Artificial Sequence
<220> FEATURE:
<223> OTHER INFORMATION: polynucleotide sequence encoding 1A11.H5 VH

<400> SEQUENCE: 34

```
caggtgcagc tggtgcagag cggagccgag gtgaagaaac ccggagccag cgtgaaggtg    60
agctgcaagg ccagcggcta caccttcacc ggctacacca tgaactgggt gaggcaggcc   120
cccggccagg gactcgagtg gatgggcctg atcaaccct acaacggcgt gaccagctac   180
aaccagaagt tcaagggcaa ggtgaccctg accgtggata ccagcatcag caccgcttac   240
atggaactga gcaggctgag gtccgacgac accgccgtgt attactgcgc caggggcgac   300
ggcaactact ggtacttcga tgtgtggggc cagggcacca ccgtcacagt gagcagc      357
```

<210> SEQ ID NO 35
<211> LENGTH: 357
<212> TYPE: DNA
<213> ORGANISM: Artificial Sequence
<220> FEATURE:
<223> OTHER INFORMATION: polynucleotide sequence encoding 1A11.H6 VH

<400> SEQUENCE: 35

```
caggtgcagc tggtgcagag cggagccgag gtgaagaaac ccggagccag cgtgaaggtg    60
agctgcaagg ccagcggcta caccttcacc ggctacacca tgaactgggt gaggcaggcc   120
cccggccagg gactcgagtg gatgggcctg atcaaccct acaacggcgt gaccagctac   180
aaccagaagt tcaagggcaa ggtgaccctg accgtggata agagcatcag caccgcttac   240
atggaactga gcaggctgag gtccgacgac accgccgtgt attactgcgc caggggcgac   300
ggcaactact ggtacttcga tgtgtggggc cagggcacca ccgtcacagt gagcagc      357
```

<210> SEQ ID NO 36
<211> LENGTH: 357
<212> TYPE: DNA
<213> ORGANISM: Artificial Sequence
<220> FEATURE:
<223> OTHER INFORMATION: polynucleotide sequence encoding 1A11.H7 VH

<400> SEQUENCE: 36

```
caggtgcagc tggtgcagag cggagccgag gtgaagaaac ccggagccag cgtgaaggtg    60
agctgcaagg ccagcggcta caccttcacc ggctacacca tgaactgggt gaggcaggcc   120
cccggccagg gactcgagtg gatgggcctg atcaaccct acaacggcgt gaccagctac   180
aaccagaagt tcaagggcaa ggtgaccctg accgtggcca agagcatcag caccgcttac   240
atggaactga gcaggctgag gtccgacgac accgccgtgt attactgcgc caggggcgac   300
```

```
ggcaactact ggtacttcga tgtgtggggc cagggcacca ccgtcacagt gagcagc      357
```

<210> SEQ ID NO 37
<211> LENGTH: 357
<212> TYPE: DNA
<213> ORGANISM: Artificial Sequence
<220> FEATURE:
<223> OTHER INFORMATION: polynucleotide encoding 1A11c VH

<400> SEQUENCE: 37

```
gaggtgcagc tgcagcagag cggccccgaa ctgctgaagc ccggcgctag catgaagatc       60
agctgcaagg ccagcggcta cagcttcacc ggctacacca tgaactgggt caagcagtcc      120
cacggcaaga acctggagtg gatcggcctg atcaaccccct acaacggcgt gacctcctac     180
aaccagaagt tcaagggcaa ggccacccctc acagtggcca aaagcagcag caccgcctac    240
atggaactgc tgagcctgac cagcgaggac agcgccgtgt actattgcgc caggggcgac     300
ggcaattact ggtacttcga cgtgtggggc gccggaacca ccgtgaccgt gtctagc        357
```

<210> SEQ ID NO 38
<211> LENGTH: 315
<212> TYPE: DNA
<213> ORGANISM: Artificial Sequence
<220> FEATURE:
<223> OTHER INFORMATION: polynucleotide encoding 1A11c Vk

<400> SEQUENCE: 38

```
gagatcgtgc tgacccagag ccccgcaatt accgccgcca gcctgggcca gaaggtgacc       60
atcacctgca gcgcaagcag cagcgtgacc tacatgcact ggtaccagca gaagagcggc     120
accagcccca agccctggat ctacgagatc tccaagctcg cctctggagt ccctgtgagg     180
ttcagcggca gcggcagcgg cactagctac tcactgacca tcagcagcat ggaggccgaa     240
gacgccgcca tctattactg ccaggagtgg aactacccct acaccttcgg cggcggcacc     300
aaactggaga tcaag                                                     315
```

<210> SEQ ID NO 39
<211> LENGTH: 6
<212> TYPE: PRT
<213> ORGANISM: Mus musculus

<400> SEQUENCE: 39

```
Thr Asp Tyr Ala Trp Asn
 1               5
```

<210> SEQ ID NO 40
<211> LENGTH: 16
<212> TYPE: PRT
<213> ORGANISM: Mus musculus

<400> SEQUENCE: 40

```
Tyr Ile Phe Tyr Ser Gly Ser Thr Thr Tyr Thr Pro Ser Leu Lys Ser
 1               5                  10                  15
```

<210> SEQ ID NO 41
<211> LENGTH: 11
<212> TYPE: PRT
<213> ORGANISM: Mus musculus

<400> SEQUENCE: 41

```
Gly Gly Tyr Asp Val Asn Tyr Phe Asp Tyr Trp
 1               5                  10
```

<210> SEQ ID NO 42
<211> LENGTH: 7
<212> TYPE: PRT
<213> ORGANISM: Mus musculus

<400> SEQUENCE: 42

Leu Ala Ser Gln Thr Ile Gly
1               5

<210> SEQ ID NO 43
<211> LENGTH: 7
<212> TYPE: PRT
<213> ORGANISM: Mus musculus

<400> SEQUENCE: 43

Ala Ala Thr Arg Leu Ala Asp
1               5

<210> SEQ ID NO 44
<211> LENGTH: 9
<212> TYPE: PRT
<213> ORGANISM: Mus musculus

<400> SEQUENCE: 44

Gln Gln Phe Phe Ser Thr Pro Trp Thr
1               5

<210> SEQ ID NO 45
<211> LENGTH: 119
<212> TYPE: PRT
<213> ORGANISM: Mus musculus

<400> SEQUENCE: 45

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Thr Asp
            20                  25                  30

Tyr Ala Trp Asn Trp Ile Arg Gln Phe Pro Gly Asn Lys Leu Glu Trp
        35                  40                  45

Met Gly Tyr Ile Phe Tyr Ser Gly Ser Thr Thr Tyr Thr Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Gly Gly Tyr Asp Val Asn Tyr Phe Asp Tyr Trp Gly Gln Gly
            100                 105                 110

Thr Thr Leu Thr Val Ser Ser
        115

<210> SEQ ID NO 46
<211> LENGTH: 107
<212> TYPE: PRT
<213> ORGANISM: Mus musculus

<400> SEQUENCE: 46

Asp Ile Gln Met Thr Gln Ser Pro Ala Ser Gln Ser Ala Ser Leu Gly
1               5                   10                  15

Glu Ser Val Thr Ile Thr Cys Leu Ala Ser Gln Thr Ile Gly Ala Trp
            20                  25                  30

Leu Ala Trp Tyr Gln Gln Lys Pro Gly Lys Ser Pro Gln Leu Leu Ile
        35                  40                  45

Tyr Ala Ala Thr Arg Leu Ala Asp Gly Val Pro Ser Arg Phe Ser Gly
 50                  55                  60

Ser Gly Ser Gly Thr Lys Phe Ser Phe Lys Ile Ser Ser Leu Gln Ala
 65                  70                  75                  80

Glu Asp Phe Val Ser Tyr Tyr Cys Gln Gln Phe Ser Thr Pro Trp
                 85                  90                  95

Thr Phe Gly Gly Gly Thr Lys Leu Glu Ile Lys
            100                 105

<210> SEQ ID NO 47
<211> LENGTH: 119
<212> TYPE: PRT
<213> ORGANISM: Artificial Sequence
<220> FEATURE:
<223> OTHER INFORMATION: 6A3.IGHV4_61.H0 VH

<400> SEQUENCE: 47

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Val Ser Thr Asp
            20                  25                  30

Tyr Ala Trp Asn Trp Ile Arg Gln Pro Pro Gly Lys Gly Leu Glu Trp
        35                  40                  45

Ile Gly Tyr Ile Phe Tyr Ser Gly Ser Thr Tyr Thr Pro Ser Leu
 50                  55                  60

Lys Ser Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Gly Gly Tyr Asp Val Asn Tyr Phe Asp Tyr Trp Gly Gln Gly
            100                 105                 110

Thr Thr Val Thr Val Ser Ser
        115

<210> SEQ ID NO 48
<211> LENGTH: 119
<212> TYPE: PRT
<213> ORGANISM: Artificial Sequence
<220> FEATURE:
<223> OTHER INFORMATION: 6A3.IGHV4_61.H1 VH

<400> SEQUENCE: 48

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Val Ser Thr Asp
            20                  25                  30

Tyr Ala Trp Asn Trp Ile Arg Gln Pro Pro Gly Lys Gly Leu Glu Trp
        35                  40                  45

Ile Gly Tyr Ile Phe Tyr Ser Gly Ser Thr Tyr Thr Pro Ser Leu
 50                  55                  60

Lys Ser Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Gly Gly Tyr Asp Val Asn Tyr Phe Asp Tyr Trp Gly Gln Gly
            100                 105                 110

Thr Thr Val Thr Val Ser Ser
        115

<210> SEQ ID NO 49
<211> LENGTH: 119
<212> TYPE: PRT
<213> ORGANISM: Artificial Sequence
<220> FEATURE:
<223> OTHER INFORMATION: 6A3.IGHV4_61.H2 VH

<400> SEQUENCE: 49

Gln Val Gln Leu Gln Glu Ser Gly Pro Gly Leu Val Lys Pro Ser Glu
 1               5                  10                  15

Thr Leu Ser Leu Thr Cys Thr Val Ser Gly Tyr Ser Val Ser Thr Asp
            20                  25                  30

Tyr Ala Trp Asn Trp Ile Arg Gln Pro Pro Gly Lys Gly Leu Glu Trp
        35                  40                  45

Ile Gly Tyr Ile Phe Tyr Ser Gly Ser Thr Tyr Thr Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Tyr Asp Val Asn Tyr Phe Asp Tyr Trp Gly Gln Gly
            100                 105                 110

Thr Thr Val Thr Val Ser Ser
        115

<210> SEQ ID NO 50
<211> LENGTH: 119
<212> TYPE: PRT
<213> ORGANISM: Artificial Sequence
<220> FEATURE:
<223> OTHER INFORMATION: 6A3.IGHV4_61.H3 VH

<400> SEQUENCE: 50

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Val Thr Thr Asp
            20                  25                  30

Tyr Ala Trp Asn Trp Ile Arg Gln Pro Pro Gly Lys Gly Leu Glu Trp
        35                  40                  45

Ile Gly Tyr Ile Phe Tyr Ser Gly Ser Thr Tyr Thr Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Tyr Asp Val Asn Tyr Phe Asp Tyr Trp Gly Gln Gly
            100                 105                 110

Thr Thr Val Thr Val Ser Ser
        115

<210> SEQ ID NO 51
<211> LENGTH: 119
<212> TYPE: PRT
<213> ORGANISM: Artificial Sequence
<220> FEATURE:
<223> OTHER INFORMATION: 6A3.IGHV4_61.H5 VH

<400> SEQUENCE: 51

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Thr Asp
            20                  25                  30

Tyr Ala Trp Asn Trp Ile Arg Gln Pro Pro Gly Lys Gly Leu Glu Trp
        35                  40                  45

Met Gly Tyr Ile Phe Tyr Ser Gly Ser Thr Thr Tyr Thr Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Tyr Asp Val Asn Tyr Phe Asp Tyr Trp Gly Gln Gly
            100                 105                 110

Thr Thr Val Thr Val Ser Ser
            115

<210> SEQ ID NO 52
<211> LENGTH: 119
<212> TYPE: PRT
<213> ORGANISM: Artificial Sequence
<220> FEATURE:
<223> OTHER INFORMATION: 6A3.IGHV4_61.H5 VH

<400> SEQUENCE: 52

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Thr Asp
            20                  25                  30

Tyr Ala Trp Asn Trp Ile Arg Gln Pro Pro Gly Lys Gly Leu Glu Trp
        35                  40                  45

Met Gly Tyr Ile Phe Tyr Ser Gly Ser Thr Thr Tyr Thr Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Tyr Asp Val Asn Tyr Phe Asp Tyr Trp Gly Gln Gly
            100                 105                 110

Thr Thr Val Thr Val Ser Ser
            115

<210> SEQ ID NO 53
<211> LENGTH: 119
<212> TYPE: PRT
<213> ORGANISM: Artificial Sequence
<220> FEATURE:
<223> OTHER INFORMATION: 6A3.IGHV4_61.H6 VH

<400> SEQUENCE: 53

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Val Ser Thr Asp
            20                  25                  30

Tyr Ala Trp Asn Trp Ile Arg Gln Pro Pro Gly Lys Gly Leu Glu Trp
        35                  40                  45

Ile Gly Tyr Ile Phe Tyr Ser Gly Ser Thr Tyr Thr Pro Ser Leu
        50                  55                  60

Lys Ser Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                85                  90                  95

Ala Arg Gly Gly Tyr Asp Val Asn Tyr Phe Asp Tyr Trp Gly Gln Gly
                100                 105                 110

Thr Thr Val Thr Val Ser Ser
        115

<210> SEQ ID NO 54
<211> LENGTH: 119
<212> TYPE: PRT
<213> ORGANISM: Artificial Sequence
<220> FEATURE:
<223> OTHER INFORMATION: 6A3.IGHV4_61.H7 VH

<400> SEQUENCE: 54

Gln Val Gln Leu Gln Glu Ser Gly Pro Gly Leu Val Lys Pro Ser Glu
 1               5                   10                  15

Thr Leu Ser Leu Thr Cys Thr Val Ser Gly Tyr Ser Val Thr Thr Asp
                20                  25                  30

Tyr Ala Trp Asn Trp Ile Arg Gln Pro Pro Gly Lys Gly Leu Glu Trp
            35                  40                  45

Ile Gly Tyr Ile Phe Tyr Ser Gly Ser Thr Tyr Thr Pro Ser Leu
        50                  55                  60

Lys Ser Arg Val Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                85                  90                  95

Ala Arg Gly Gly Tyr Asp Val Asn Tyr Phe Asp Tyr Trp Gly Gln Gly
                100                 105                 110

Thr Thr Val Thr Val Ser Ser
        115

<210> SEQ ID NO 55
<211> LENGTH: 119
<212> TYPE: PRT
<213> ORGANISM: Artificial Sequence
<220> FEATURE:
<223> OTHER INFORMATION: 6A3.IGHV4_61.H8 VH

<400> SEQUENCE: 55

Gln Val Gln Leu Gln Glu Ser Gly Pro Gly Leu Val Lys Pro Ser Glu
 1               5                   10                  15

Thr Leu Ser Leu Thr Cys Thr Val Ser Gly Tyr Ser Val Thr Thr Asp
                20                  25                  30

Tyr Ala Trp Asn Trp Ile Arg Gln Pro Pro Gly Lys Gly Leu Glu Trp
            35                  40                  45

Ile Gly Tyr Ile Phe Tyr Ser Gly Ser Thr Tyr Thr Pro Ser Leu
        50                  55                  60

Lys Ser Arg Ile Thr Ile Ser Arg Asp Thr Ser Lys Asn Gln Phe Ser
 65                  70                  75                  80

Leu Lys Leu Ser Ser Val Thr Ala Ala Asp Thr Ala Val Tyr Tyr Cys
                85                  90                  95

Ala Arg Gly Gly Tyr Asp Val Asn Tyr Phe Asp Tyr Trp Gly Gln Gly

Thr Thr Val Thr Val Ser Ser
        115

<210> SEQ ID NO 56
<211> LENGTH: 119
<212> TYPE: PRT
<213> ORGANISM: Artificial Sequence
<220> FEATURE:
<223> OTHER INFORMATION: 6A3.IGHV4_61.H9 VH

<400> SEQUENCE: 56

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Val Thr Thr Asp
            20                  25                  30

Tyr Ala Trp Asn Trp Ile Arg Gln Pro Pro Gly Lys Gly Leu Glu Trp
        35                  40                  45

Met Gly Tyr Ile Phe Tyr Ser Gly Ser Thr Thr Tyr Thr Pro Ser Leu
    50                  55                  60

Lys Ser Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Gly Tyr Asp Val Asn Tyr Phe Asp Tyr Trp Gly Gln Gly
            100                 105                 110

Thr Thr Val Thr Val Ser Ser
        115

<210> SEQ ID NO 57
<211> LENGTH: 119
<212> TYPE: PRT
<213> ORGANISM: Artificial Sequence
<220> FEATURE:
<223> OTHER INFORMATION: 6A3.IGHV3-33.H0 VH

<400> SEQUENCE: 57

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Asp
            20                  25                  30

Tyr Ala Trp Asn Trp Val Arg Gln Ala Pro Gly Lys Gly Leu Glu Trp
        35                  40                  45

Val Ala Tyr Ile Phe Tyr Ser Gly Ser Thr Thr Tyr Thr Pro Ser Leu
    50                  55                  60

Lys Ser Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Tyr Asp Val Asn Tyr Phe Asp Tyr Trp Gly Gln Gly
            100                 105                 110

Thr Thr Val Thr Val Ser Ser
        115

<210> SEQ ID NO 58
<211> LENGTH: 119
<212> TYPE: PRT
<213> ORGANISM: Artificial Sequence
<220> FEATURE:

<223> OTHER INFORMATION: 6A3.IGHV3-33.H1 VH

<400> SEQUENCE: 58

Gln Val Gln Leu Val Glu Ser Gly Gly Gly Val Val Gln Pro Gly Arg
1               5                   10                  15

Ser Leu Arg Leu Ser Cys Ala Ala Ser Gly Tyr Thr Phe Ser Thr Asp
            20                  25                  30

Tyr Ala Trp Asn Trp Val Arg Gln Ala Pro Gly Lys Gly Leu Glu Trp
        35                  40                  45

Val Ala Tyr Ile Phe Tyr Ser Gly Ser Thr Thr Tyr Thr Pro Ser Leu
    50                  55                  60

Lys Ser Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Tyr Asp Val Asn Tyr Phe Asp Tyr Trp Gly Gln Gly
            100                 105                 110

Thr Thr Val Thr Val Ser Ser
            115

<210> SEQ ID NO 59
<211> LENGTH: 119
<212> TYPE: PRT
<213> ORGANISM: Artificial Sequence
<220> FEATURE:
<223> OTHER INFORMATION: 6A3.IGHV3-33.H2 VH

<400> SEQUENCE: 59

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Thr Thr Asp
            20                  25                  30

Tyr Ala Trp Asn Trp Val Arg Gln Ala Pro Gly Lys Gly Leu Glu Trp
        35                  40                  45

Val Ala Tyr Ile Phe Tyr Ser Gly Ser Thr Thr Tyr Thr Pro Ser Leu
    50                  55                  60

Lys Ser Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Tyr Asp Val Asn Tyr Phe Asp Tyr Trp Gly Gln Gly
            100                 105                 110

Thr Thr Val Thr Val Ser Ser
            115

<210> SEQ ID NO 60
<211> LENGTH: 119
<212> TYPE: PRT
<213> ORGANISM: Artificial Sequence
<220> FEATURE:
<223> OTHER INFORMATION: 6A3.IGHV3-33.H3 VH

<400> SEQUENCE: 60

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Phe Ser Thr Asp
            20                  25                  30

Tyr Ala Trp Asn Trp Val Arg Gln Ala Pro Gly Lys Gly Leu Glu Trp

```
                35                  40                  45
Val Ala Tyr Ile Phe Tyr Ser Gly Ser Thr Thr Tyr Thr Pro Ser Leu
         50                  55                  60
Lys Ser Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Gly Gly Tyr Asp Val Asn Tyr Phe Asp Tyr Trp Gly Gln Gly
            100                 105                 110
Thr Thr Val Thr Val Ser Ser
            115

<210> SEQ ID NO 61
<211> LENGTH: 119
<212> TYPE: PRT
<213> ORGANISM: Artificial Sequence
<220> FEATURE:
<223> OTHER INFORMATION: 6A3.IGHV3-33.H4 VH

<400> SEQUENCE: 61

Gln Val Gln Leu Val Glu Ser Gly Gly Gly Val Val Gln Pro Gly Arg
 1               5                  10                  15
Ser Leu Arg Leu Ser Cys Ala Ala Ser Gly Phe Thr Ile Ser Thr Asp
            20                  25                  30
Tyr Ala Trp Asn Trp Val Arg Gln Ala Pro Gly Lys Gly Leu Glu Trp
         35                  40                  45
Val Ala Tyr Ile Phe Tyr Ser Gly Ser Thr Thr Tyr Thr Pro Ser Leu
         50                  55                  60
Lys Ser Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Arg Gly Gly Tyr Asp Val Asn Tyr Phe Asp Tyr Trp Gly Gln Gly
            100                 105                 110
Thr Thr Val Thr Val Ser Ser
            115

<210> SEQ ID NO 62
<211> LENGTH: 119
<212> TYPE: PRT
<213> ORGANISM: Artificial Sequence
<220> FEATURE:
<223> OTHER INFORMATION: 6A3.IGHV3-33.H5 VH

<400> SEQUENCE: 62

Gln Val Gln Leu Val Glu Ser Gly Gly Gly Val Val Gln Pro Gly Arg
 1               5                  10                  15
Ser Leu Arg Leu Ser Cys Ala Ala Ser Gly Phe Thr Phe Ser Thr Asp
            20                  25                  30
Tyr Ala Trp Asn Trp Val Arg Gln Ala Pro Gly Lys Gly Leu Glu Trp
         35                  40                  45
Val Ala Tyr Ile Phe Tyr Ser Gly Ser Thr Thr Tyr Thr Pro Ser Leu
         50                  55                  60
Lys Ser Arg Ile Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
```

-continued

Ala Arg Gly Gly Tyr Asp Val Asn Tyr Phe Asp Tyr Trp Gly Gln Gly
            100                 105                 110

Thr Thr Val Thr Val Ser Ser
        115

<210> SEQ ID NO 63
<211> LENGTH: 119
<212> TYPE: PRT
<213> ORGANISM: Artificial Sequence
<220> FEATURE:
<223> OTHER INFORMATION: 6A3.IGHV3-33.H6 VH

<400> SEQUENCE: 63

Gln Val Gln Leu Val Glu Ser Gly Gly Gly Val Val Gln Pro Gly Arg
 1               5                   10                  15

Ser Leu Arg Leu Ser Cys Ala Ala Ser Gly Phe Thr Phe Ser Thr Asp
            20                  25                  30

Tyr Ala Trp Asn Trp Val Arg Gln Ala Pro Gly Lys Gly Leu Glu Trp
        35                  40                  45

Val Ala Tyr Ile Phe Tyr Ser Gly Ser Thr Thr Tyr Thr Pro Ser Leu
    50                  55                  60

Lys Ser Arg Phe Thr Ile Ser Arg Asp Thr Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Tyr Asp Val Asn Tyr Phe Asp Tyr Trp Gly Gln Gly
            100                 105                 110

Thr Thr Val Thr Val Ser Ser
        115

<210> SEQ ID NO 64
<211> LENGTH: 119
<212> TYPE: PRT
<213> ORGANISM: Artificial Sequence
<220> FEATURE:
<223> OTHER INFORMATION: 6A3.IGHV3-33.H8 VH

<400> SEQUENCE: 64

Gln Val Gln Leu Val Glu Ser Gly Gly Gly Val Val Gln Pro Gly Arg
 1               5                   10                  15

Ser Leu Arg Leu Ser Cys Ala Ala Ser Gly Phe Thr Phe Ser Thr Asp
            20                  25                  30

Tyr Ala Trp Asn Trp Val Arg Gln Ala Pro Gly Lys Gly Leu Glu Trp
        35                  40                  45

Val Gly Tyr Ile Phe Tyr Ser Gly Ser Thr Thr Tyr Thr Pro Ser Leu
    50                  55                  60

Lys Ser Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Tyr Asp Val Asn Tyr Phe Asp Tyr Trp Gly Gln Gly
            100                 105                 110

Thr Thr Val Thr Val Ser Ser
        115

<210> SEQ ID NO 65
<211> LENGTH: 119
<212> TYPE: PRT
<213> ORGANISM: Artificial Sequence

```
<220> FEATURE:
<223> OTHER INFORMATION: 6A3.IGHV3-33.H8 VH

<400> SEQUENCE: 65

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Asp
            20                  25                  30

Tyr Ala Trp Asn Trp Val Arg Gln Ala Pro Gly Lys Gly Leu Glu Trp
        35                  40                  45

Val Gly Tyr Ile Phe Tyr Ser Gly Ser Thr Tyr Thr Pro Ser Leu
    50                  55                  60

Lys Ser Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Tyr Asp Val Asn Tyr Phe Asp Tyr Trp Gly Gln Gly
            100                 105                 110

Thr Thr Val Thr Val Ser Ser
        115

<210> SEQ ID NO 66
<211> LENGTH: 119
<212> TYPE: PRT
<213> ORGANISM: Artificial Sequence
<220> FEATURE:
<223> OTHER INFORMATION: 6A3.IGHV3-33.H9 VH

<400> SEQUENCE: 66

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Thr Asp
            20                  25                  30

Tyr Ala Trp Asn Trp Val Arg Gln Ala Pro Gly Lys Gly Leu Glu Trp
        35                  40                  45

Val Ala Tyr Ile Phe Tyr Ser Gly Ser Thr Tyr Thr Pro Ser Leu
    50                  55                  60

Lys Ser Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Tyr Asp Val Asn Tyr Phe Asp Tyr Trp Gly Gln Gly
            100                 105                 110

Thr Thr Val Thr Val Ser Ser
        115

<210> SEQ ID NO 67
<211> LENGTH: 119
<212> TYPE: PRT
<213> ORGANISM: Artificial Sequence
<220> FEATURE:
<223> OTHER INFORMATION: 6A3.IGHV3-33.H10 VH

<400> SEQUENCE: 67

Gln Val Gln Leu Val Glu Ser Gly Gly Gly Val Val Gln Pro Gly Arg
1               5                   10                  15

Ser Leu Arg Leu Ser Cys Ala Val Ser Gly Phe Thr Phe Ser Thr Asp
            20                  25                  30
```

```
Tyr Ala Trp Asn Trp Val Arg Gln Ala Pro Gly Lys Gly Leu Glu Trp
            35                  40                  45

Val Ala Tyr Ile Phe Tyr Ser Gly Ser Thr Thr Tyr Thr Pro Ser Leu
 50                      55                  60

Lys Ser Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gly Tyr Asp Val Asn Tyr Phe Asp Tyr Trp Gly Gln Gly
             100                 105                 110

Thr Thr Val Thr Val Ser Ser
             115

<210> SEQ ID NO 68
<211> LENGTH: 119
<212> TYPE: PRT
<213> ORGANISM: Artificial Sequence
<220> FEATURE:
<223> OTHER INFORMATION: 6A3.IGHV3-33.H11 VH

<400> SEQUENCE: 68

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Thr Asp
             20                  25                  30

Tyr Ala Trp Asn Trp Val Arg Gln Ala Pro Gly Lys Gly Leu Glu Trp
            35                  40                  45

Met Ala Tyr Ile Phe Tyr Ser Gly Ser Thr Thr Tyr Thr Pro Ser Leu
 50                      55                  60

Lys Ser Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gly Tyr Asp Val Asn Tyr Phe Asp Tyr Trp Gly Gln Gly
             100                 105                 110

Thr Thr Val Thr Val Ser Ser
             115

<210> SEQ ID NO 69
<211> LENGTH: 107
<212> TYPE: PRT
<213> ORGANISM: Artificial Sequence
<220> FEATURE:
<223> OTHER INFORMATION: 6A3.L0 Vk

<400> SEQUENCE: 69

Asp Ile Gln Met Thr Gln Ser Pro Ser Ser Leu Ser Ala Ser Val Gly
 1               5                  10                  15

Asp Arg Val Thr Ile Thr Cys Leu Ala Ser Gln Thr Ile Gly Ala Trp
             20                  25                  30

Leu Ala Trp Tyr Gln Gln Lys Pro Gly Lys Ala Pro Lys Leu Leu Ile
            35                  40                  45

Tyr Ala Ala Thr Arg Leu Ala Asp Gly Val Pro Ser Arg Phe Ser Gly
 50                      55                  60

Ser Gly Ser Gly Thr Asp Phe Thr Leu Thr Ile Ser Ser Leu Gln Pro
 65                  70                  75                  80

Glu Asp Phe Ala Val Tyr Tyr Cys Gln Gln Phe Phe Ser Thr Pro Trp
                 85                  90                  95
```

```
Thr Phe Gly Gln Gly Thr Lys Leu Glu Ile Lys
            100                 105

<210> SEQ ID NO 70
<211> LENGTH: 107
<212> TYPE: PRT
<213> ORGANISM: Artificial Sequence
<220> FEATURE:
<223> OTHER INFORMATION: 6A3.L1 Vk

<400> SEQUENCE: 70

Asp Ile Gln Met Thr Gln Ser Pro Ser Ser Leu Ser Ala Ser Val Gly
 1               5                  10                  15

Asp Arg Val Thr Ile Thr Cys Leu Ala Ser Gln Thr Ile Gly Ala Trp
            20                  25                  30

Leu Ala Trp Tyr Gln Gln Lys Pro Gly Lys Ala Pro Gln Leu Leu Ile
        35                  40                  45

Tyr Ala Ala Thr Arg Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Phe Phe Ser Thr Pro Trp
                85                  90                  95

Thr Phe Gly Gln Gly Thr Lys Leu Glu Ile Lys
            100                 105

<210> SEQ ID NO 71
<211> LENGTH: 107
<212> TYPE: PRT
<213> ORGANISM: Artificial Sequence
<220> FEATURE:
<223> OTHER INFORMATION: 6A3.L2 Vk

<400> SEQUENCE: 71

Asp Ile Gln Met Thr Gln Ser Pro Ser Ser Leu Ser Ala Ser Val Gly
 1               5                  10                  15

Asp Arg Val Thr Ile Thr Cys Leu Ala Ser Gln Thr Ile Gly Ala Trp
            20                  25                  30

Leu Ala Trp Tyr Gln Gln Lys Pro Gly Lys Ala Pro Lys Leu Leu Ile
        35                  40                  45

Tyr Ala Ala Thr Arg Leu Ala Asp Gly Val Pro Ser Arg Phe Ser Gly
    50                  55                  60

Ser Gly Ser Gly Thr Lys Phe Thr Leu Thr Ile Ser Ser Leu Gln Pro
65                  70                  75                  80

Glu Asp Phe Ala Val Tyr Tyr Cys Gln Gln Phe Phe Ser Thr Pro Trp
                85                  90                  95

Thr Phe Gly Gln Gly Thr Lys Leu Glu Ile Lys
            100                 105

<210> SEQ ID NO 72
<211> LENGTH: 107
<212> TYPE: PRT
<213> ORGANISM: Artificial Sequence
<220> FEATURE:
<223> OTHER INFORMATION: 6A3.L3 Vk

<400> SEQUENCE: 72

Asp Ile Gln Met Thr Gln Ser Pro Ser Ser Leu Ser Ala Ser Val Gly
 1               5                  10                  15
```

```
Asp Arg Val Thr Ile Thr Cys Leu Ala Ser Gln Thr Ile Gly Ala Trp
            20                  25                  30

Leu Ala Trp Tyr Gln Gln Lys Pro Gly Lys Ala Pro Gln Leu Leu Ile
        35                  40                  45

Tyr Ala Ala Thr Arg Leu Ala Asp Gly Val Pro Ser Arg Phe Ser Gly
50                  55                  60

Ser Gly Ser Gly Thr Lys Phe Thr Leu Thr Ile Ser Ser Leu Gln Pro
65                  70                  75                  80

Glu Asp Phe Ala Val Tyr Tyr Cys Gln Gln Phe Phe Ser Thr Pro Trp
                85                  90                  95

Thr Phe Gly Gln Gly Thr Lys Leu Glu Ile Lys
            100                 105
```

<210> SEQ ID NO 73
<211> LENGTH: 119
<212> TYPE: PRT
<213> ORGANISM: Mus musculus

<400> SEQUENCE: 73

```
Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Thr Asp
            20                  25                  30

Tyr Ala Trp Asn Trp Ile Arg Gln Phe Pro Gly Asn Lys Leu Glu Trp
        35                  40                  45

Met Gly Tyr Ile Phe Tyr Ser Gly Ser Thr Tyr Thr Pro Ser Leu
50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Gly Gly Tyr Asp Val Asn Tyr Phe Asp Tyr Trp Gly Gln Gly
            100                 105                 110

Thr Thr Leu Thr Val Ser Ser
        115
```

<210> SEQ ID NO 74
<211> LENGTH: 107
<212> TYPE: PRT
<213> ORGANISM: Mus musculus

<400> SEQUENCE: 74

```
Asp Ile Gln Met Thr Gln Ser Pro Ala Ser Gln Ser Ala Ser Leu Gly
1               5                   10                  15

Glu Ser Val Thr Ile Thr Cys Leu Ala Ser Gln Thr Ile Gly Ala Trp
            20                  25                  30

Leu Ala Trp Tyr Gln Gln Lys Pro Gly Lys Ser Pro Gln Leu Leu Ile
        35                  40                  45

Tyr Ala Ala Thr Arg Leu Ala Asp Gly Val Pro Ser Arg Phe Ser Gly
50                  55                  60

Ser Gly Ser Gly Thr Lys Phe Ser Phe Lys Ile Ser Ser Leu Gln Ala
65                  70                  75                  80

Glu Asp Phe Val Ser Tyr Tyr Cys Gln Gln Phe Phe Ser Thr Pro Trp
                85                  90                  95

Thr Phe Gly Gly Gly Thr Lys Leu Glu Ile Lys
            100                 105
```

<210> SEQ ID NO 75
<211> LENGTH: 357
<212> TYPE: DNA
<213> ORGANISM: Artificial Sequence
<220> FEATURE:
<223> OTHER INFORMATION: polynucleotide sequence encoding
      6A3.IGHV4_61.H0 VH

<400> SEQUENCE: 75

```
caggtgcagc tgcaggagag cggacccggc ctggtgaaac ccagcgagac cctgagcctg    60
acctgcacag tgagcggcgg ctccgtgagc accgactacg cttggaactg gatcaggcag   120
cctcccggca agggcctgga gtggatcggc tacatcttct acagcggcag caccacctac   180 accccccagcc tcaagtccag ggtgaccatc agcgtcgaca ccagcaagaa ccagttcagc   240
ctgaagctga gcagcgtgac cgccgccgat accgccgtgt actactgcgc caggggaggc   300
tacgacgtga actacttcga ctactggggc cagggcacca cctatactgt gagcagc      357
```

<210> SEQ ID NO 76
<211> LENGTH: 357
<212> TYPE: DNA
<213> ORGANISM: Artificial Sequence
<220> FEATURE:
<223> OTHER INFORMATION: polynucleotide sequence encoding
      6A3.IGHV4_61.H1 VH

<400> SEQUENCE: 76

```
caggtgcagc tgcaggagag cggacccggc ctggtgaaac ccagcgagac cctgagcctg    60
acctgcacag tgagcggcgg ctccgtgagc accgactacg cttggaactg gatcaggcag   120
cctcccggca agggcctgga gtggatcggc tacatcttct acagcggcag caccacctac   180 accccccagcc tcaagtccag ggtgaccatc agcagggaca ccagcaagaa ccagttcagc   240
ctgaagctga gcagcgtgac cgccgccgat accgccgtgt actactgcgc caggggaggc   300
tacgacgtga actacttcga ctactggggc cagggcacca cctatactgt gagcagc      357
```

<210> SEQ ID NO 77
<211> LENGTH: 357
<212> TYPE: DNA
<213> ORGANISM: Artificial Sequence
<220> FEATURE:
<223> OTHER INFORMATION: polynucleotide sequence encoding
      6A3.IGHV4_61.H2 VH

<400> SEQUENCE: 77

```
caggtgcagc tgcaggagag cggacccggc ctggtgaaac ccagcgagac cctgagcctg    60
acctgcacag tgagcggcta ctccgtgagc accgactacg cttggaactg gatcaggcag   120
cctcccggca agggcctgga gtggatcggc tacatcttct acagcggcag caccacctac   180 accccccagcc tcaagtccag ggtgaccatc agcgtcgaca ccagcaagaa ccagttcagc   240
ctgaagctga gcagcgtgac cgccgccgat accgccgtgt actactgcgc caggggaggc   300
tacgacgtga actacttcga ctactggggc cagggcacca cctatactgt gagcagc      357
```

<210> SEQ ID NO 78
<211> LENGTH: 357
<212> TYPE: DNA
<213> ORGANISM: Artificial Sequence
<220> FEATURE:
<223> OTHER INFORMATION: polynucleotide sequence encoding
      6A3.IGHV4_61.H3 VH

<400> SEQUENCE: 78

| | |
|---|---|
| caggtgcagc tgcaggagag cggacccggc ctggtgaaac ccagcgagac cctgagcctg | 60 |
| acctgcacag tgagcggcgg ctccgtgacc accgactacg cttggaactg gatcaggcag | 120 |
| cctccccggca agggcctgga gtggatcggc tacatcttct acagcggcag caccacctac | 180 |
| acccccagcc tcaagtccag ggtgaccatc agcgtcgaca ccagcaagaa ccagttcagc | 240 |
| ctgaagctga gcagcgtgac cgccgccgat accgccgtgt actactgcgc caggggaggc | 300 |
| tacgacgtga actacttcga ctactggggc cagggcacca cctatactgt gagcagc | 357 |

<210> SEQ ID NO 79
<211> LENGTH: 357
<212> TYPE: DNA
<213> ORGANISM: Artificial Sequence
<220> FEATURE:
<223> OTHER INFORMATION: polynucleotide sequence encoding
      6A3.IGHV4_61.H4 VH

<400> SEQUENCE: 79

| | |
|---|---|
| caggtgcagc tgcaggagag cggacccggc ctggtgaaac ccagcgagac cctgagcctg | 60 |
| acctgcacag tgagcggcgg ctccgtgagc accgactacg cttggaactg gatcaggcag | 120 |
| cctccccggca agggcctgga gtggatcggc tacatcttct acagcggcag caccacctac | 180 |
| acccccagcc tcaagtccag gatcaccatc agcgtcgaca ccagcaagaa ccagttcagc | 240 |
| ctgaagctga gcagcgtgac cgccgccgat accgccgtgt actactgcgc caggggaggc | 300 |
| tacgacgtga actacttcga ctactggggc cagggcacca cctatactgt gagcagc | 357 |

<210> SEQ ID NO 80
<211> LENGTH: 357
<212> TYPE: DNA
<213> ORGANISM: Artificial Sequence
<220> FEATURE:
<223> OTHER INFORMATION: polynucleotide sequence encoding
      6A3.IGHV4_61.H5 VH

<400> SEQUENCE: 80

| | |
|---|---|
| caggtgcagc tgcaggagag cggacccggc ctggtgaaac ccagcgagac cctgagcctg | 60 |
| acctgcacag tgagcggcgg ctccgtgagc accgactacg cttggaactg gatcaggcag | 120 |
| cctccccggca agggcctgga gtggatgggc tacatcttct acagcggcag caccacctac | 180 |
| acccccagcc tcaagtccag ggtgaccatc agcgtcgaca ccagcaagaa ccagttcagc | 240 |
| ctgaagctga gcagcgtgac cgccgccgat accgccgtgt actactgcgc caggggaggc | 300 |
| tacgacgtga actacttcga ctactggggc cagggcacca cctatactgt gagcagc | 357 |

<210> SEQ ID NO 81
<211> LENGTH: 357
<212> TYPE: DNA
<213> ORGANISM: Artificial Sequence
<220> FEATURE:
<223> OTHER INFORMATION: polynucleotide sequence encoding
      6A3.IGHV4_61.H6 VH

<400> SEQUENCE: 81

| | |
|---|---|
| caggtgcagc tgcaggagag cggacccggc ctggtgaaac ccagcgagac cctgagcctg | 60 |
| acctgcacag tgagcggcta ctccgtgagc accgactacg cttggaactg gatcaggcag | 120 |
| cctccccggca agggcctgga gtggatcggc tacatcttct acagcggcag caccacctac | 180 |
| acccccagcc tcaagtccag ggtgaccatc agcagggaca ccagcaagaa ccagttcagc | 240 |
| ctgaagctga gcagcgtgac cgccgccgat accgccgtgt actactgcgc caggggaggc | 300 |

```
tacgacgtga actacttcga ctactggggc cagggcacca cctatactgt gagcagc    357
```

<210> SEQ ID NO 82
<211> LENGTH: 357
<212> TYPE: DNA
<213> ORGANISM: Artificial Sequence
<220> FEATURE:
<223> OTHER INFORMATION: polynucleotide sequence encoding
      6A3.IGHV4_61.H7 VH

<400> SEQUENCE: 82

```
caggtgcagc tgcaggagag cggacccggc ctggtgaaac ccagcgagac cctgagcctg    60
acctgcacag tgagcggcta ctccgtgacc accgactacg cttggaactg gatcaggcag    120
cctcccggca agggcctgga gtggatcggc tacatcttct acagcggcag caccacctac    180
acccccagcc tcaagtccag ggtgaccatc agcagggaca ccagcaagaa ccagttcagc    240
ctgaagctga gcagcgtgac cgccgccgat accgccgtgt actactgcgc caggggaggc    300
tacgacgtga actacttcga ctactggggc cagggcacca cctatactgt gagcagc      357
```

<210> SEQ ID NO 83
<211> LENGTH: 357
<212> TYPE: DNA
<213> ORGANISM: Artificial Sequence
<220> FEATURE:
<223> OTHER INFORMATION: polynucleotide sequence encoding
      6A3.IGHV4_61.H8 VH

<400> SEQUENCE: 83

```
caggtgcagc tgcaggagag cggacccggc ctggtgaaac ccagcgagac cctgagcctg    60
acctgcacag tgagcggcgg ctccgtgagc accgactacg cttggaactg gatcaggcag    120
cctcccggca agggcctgga gtggatcggc tacatcttct acagcggcag caccacctac    180
acccccagcc tcaagtccag ggtgaccatc agcgtcgaca ccagcaagaa ccagttcagc    240
ctgaagctga gcagcgtgac cgccgccgat accgccgtgt actactgcgc caggggaggc    300
tacgacgtga actacttcga ctactggggc cagggcacca cctatactgt gagcagc      357
```

<210> SEQ ID NO 84
<211> LENGTH: 357
<212> TYPE: DNA
<213> ORGANISM: Artificial Sequence
<220> FEATURE:
<223> OTHER INFORMATION: polynucleotide sequence encoding
      6A3.IGHV4_61.H9 VH

<400> SEQUENCE: 84

```
caggtgcagc tgcaggagag cggacccggc ctggtgaaac ccagcgagac cctgagcctg    60
acctgcacag tgagcggcta ctccgtgacc accgactacg cttggaactg gatcaggcag    120
cctcccggca agggcctgga gtggatcggc tacatcttct acagcggcag caccacctac    180
acccccagcc tcaagtccag gatcaccatc agcagggaca ccagcaagaa ccagttcagc    240
ctgaagctga gcagcgtgac cgccgccgat accgccgtgt actactgcgc caggggaggc    300
tacgacgtga actacttcga ctactggggc cagggcacca cctatactgt gagcagc      357
```

<210> SEQ ID NO 85
<211> LENGTH: 357
<212> TYPE: DNA
<213> ORGANISM: Artificial Sequence
<220> FEATURE:
<223> OTHER INFORMATION: polynucleotide sequence encoding

6A3.IGHV3_33.H0 VH

<400> SEQUENCE: 85

| | | | | | |
|---|---|---|---|---|---|
| caggtgcagc | tggtggagag | cggcggcggc | gtggtgcagc | ccggcaggag | cctgaggctc | 60 |
| tcttgcgccg | ccagcggatt | caccttcagc | accgactacg | cctggaattg | ggtgaggcag | 120 |
| gccccggga | agggcctgga | gtgggtcgcc | tacatcttct | acagcggcag | caccacctac | 180 |
| acccccagcc | tgaagagcag | gttcaccatc | agcaggaca | acagcaagaa | cacctgtac | 240 |
| ctgcagatga | acagcctgag | ggccgaggac | accgccgtgt | attactgcgc | tagggggggc | 300 |
| tacgacgtga | actacttcga | ctactggggc | cagggcacaa | ccgtgaccgt | gagcagc | 357 |

<210> SEQ ID NO 86
<211> LENGTH: 357
<212> TYPE: DNA
<213> ORGANISM: Artificial Sequence
<220> FEATURE:
<223> OTHER INFORMATION: polynucleotide sequence encoding
      6A3.IGHV3_33.H1 VH

<400> SEQUENCE: 86

| | | | | | |
|---|---|---|---|---|---|
| caggtgcagc | tggtggagag | cggcggcggc | gtggtgcagc | ccggcaggag | cctgaggctc | 60 |
| tcttgcgccg | ccagcggata | caccttcagc | accgactacg | cctggaattg | ggtgaggcag | 120 |
| gccccggga | agggcctgga | gtgggtcgcc | tacatcttct | acagcggcag | caccacctac | 180 |
| acccccagcc | tgaagagcag | gttcaccatc | agcaggaca | acagcaagaa | cacctgtac | 240 |
| ctgcagatga | acagcctgag | ggccgaggac | accgccgtgt | attactgcgc | tagggggggc | 300 |
| tacgacgtga | actacttcga | ctactggggc | cagggcacaa | ccgtgaccgt | gagcagc | 357 |

<210> SEQ ID NO 87
<211> LENGTH: 357
<212> TYPE: DNA
<213> ORGANISM: Artificial Sequence
<220> FEATURE:
<223> OTHER INFORMATION: polynucleotide sequence encoding
      6A3.IGHV3_33.H2 VH

<400> SEQUENCE: 87

| | | | | | |
|---|---|---|---|---|---|
| caggtgcagc | tggtggagag | cggcggcggc | gtggtgcagc | ccggcaggag | cctgaggctc | 60 |
| tcttgcgccg | ccagcggatt | caccttcacc | accgactacg | cctggaattg | ggtgaggcag | 120 |
| gccccggga | agggcctgga | gtgggtcgcc | tacatcttct | acagcggcag | caccacctac | 180 |
| acccccagcc | tgaagagcag | gttcaccatc | agcaggaca | acagcaagaa | cacctgtac | 240 |
| ctgcagatga | acagcctgag | ggccgaggac | accgccgtgt | attactgcgc | tagggggggc | 300 |
| tacgacgtga | actacttcga | ctactggggc | cagggcacaa | ccgtgaccgt | gagcagc | 357 |

<210> SEQ ID NO 88
<211> LENGTH: 357
<212> TYPE: DNA
<213> ORGANISM: Artificial Sequence
<220> FEATURE:
<223> OTHER INFORMATION: polynucleotide sequence encoding
      6A3.IGHV3_33.H3 VH

<400> SEQUENCE: 88

| | | | | | |
|---|---|---|---|---|---|
| caggtgcagc | tggtggagag | cggcggcggc | gtggtgcagc | ccggcaggag | cctgaggctc | 60 |
| tcttgcgccg | ccagcggatt | cagcttcagc | accgactacg | cctggaattg | ggtgaggcag | 120 |
| gccccggga | agggcctgga | gtgggtcgcc | tacatcttct | acagcggcag | caccacctac | 180 |

```
acccccagcc tgaagagcag gttcaccatc agcagggaca acagcaagaa caccctgtac    240
ctgcagatga acagcctgag ggccgaggac accgccgtgt attactgcgc tagggggggc    300
tacgacgtga actacttcga ctactggggc cagggcacaa ccgtgaccgt gagcagc       357

<210> SEQ ID NO 89
<211> LENGTH: 357
<212> TYPE: DNA
<213> ORGANISM: Artificial Sequence
<220> FEATURE:
<223> OTHER INFORMATION: polynucleotide sequence encoding
      6A3.IGHV3_33.H4 VH

<400> SEQUENCE: 89
caggtgcagc tggtggagag cggcggcggc gtggtgcagc ccggcaggag cctgaggctc    60
tcttgcgccg ccagcggatt caccatcagc accgactacg cctggaattg ggtgaggcag    120
gcccccggga agggcctgga gtgggtcgcc tacatcttct acagcggcag caccacctac    180
acccccagcc tgaagagcag gttcaccatc agcagggaca acagcaagaa caccctgtac    240
ctgcagatga acagcctgag ggccgaggac accgccgtgt attactgcgc tagggggggc    300
tacgacgtga actacttcga ctactggggc cagggcacaa ccgtgaccgt gagcagc       357

<210> SEQ ID NO 90
<211> LENGTH: 357
<212> TYPE: DNA
<213> ORGANISM: Artificial Sequence
<220> FEATURE:
<223> OTHER INFORMATION: polynucleotide sequence encoding
      6A3.IGHV3_33.H5 VH

<400> SEQUENCE: 90
caggtgcagc tggtggagag cggcggcggc gtggtgcagc ccggcaggag cctgaggctc    60
tcttgcgccg ccagcggatt caccttcagc accgactacg cctggaattg ggtgaggcag    120
gcccccggga agggcctgga gtgggtcgcc tacatcttct acagcggcag caccacctac    180
acccccagcc tgaagagcag gatcaccatc agcagggaca acagcaagaa caccctgtac    240
ctgcagatga acagcctgag ggccgaggac accgccgtgt attactgcgc tagggggggc    300
tacgacgtga actacttcga ctactggggc cagggcacaa ccgtgaccgt gagcagc       357

<210> SEQ ID NO 91
<211> LENGTH: 357
<212> TYPE: DNA
<213> ORGANISM: Artificial Sequence
<220> FEATURE:
<223> OTHER INFORMATION: polynucleotide sequence encoding
      6A3.IGHV3_33.H6 VH

<400> SEQUENCE: 91
caggtgcagc tggtggagag cggcggcggc gtggtgcagc ccggcaggag cctgaggctc    60
tcttgcgccg ccagcggatt caccttcagc accgactacg cctggaattg ggtgaggcag    120
gcccccggga agggcctgga gtgggtcgcc tacatcttct acagcggcag caccacctac    180
acccccagcc tgaagagcag gttcaccatc agcagggaca ccagcaagaa caccctgtac    240
ctgcagatga acagcctgag ggccgaggac accgccgtgt attactgcgc tagggggggc    300
tacgacgtga actacttcga ctactggggc cagggcacaa ccgtgaccgt gagcagc       357

<210> SEQ ID NO 92
<211> LENGTH: 357
<212> TYPE: DNA
```

<213> ORGANISM: Artificial Sequence
<220> FEATURE:
<223> OTHER INFORMATION: polynucleotide sequence encoding
      6A3.IGHV3_33.H7 VH

<400> SEQUENCE: 92

```
caggtgcagc tggtggagag cggcggcggc gtggtgcagc ccggcaggag cctgaggctc    60
tcttgcgccg ccagcggatt caccttcagc accgactacg cctggaattg ggtgaggcag   120
gcccccggga agggcctgga gtgggtcgcc tacatcttct acagcggcag caccacctac   180 accccagcc tgaagagcag gttcaccatc agcagggaca acagcaagaa caccttctac   240
ctgcagatga acagcctgag ggccgaggac accgccgtgt attactgcgc tagggggggc   300
tacgacgtga actacttcga ctactggggc cagggcacaa ccgtgaccgt gagcagc      357
```

<210> SEQ ID NO 93
<211> LENGTH: 357
<212> TYPE: DNA
<213> ORGANISM: Artificial Sequence
<220> FEATURE:
<223> OTHER INFORMATION: polynucleotide sequence encoding
      6A3.IGHV3_33.H8 VH

<400> SEQUENCE: 93

```
caggtgcagc tggtggagag cggcggcggc gtggtgcagc ccggcaggag cctgaggctc    60
tcttgcgccg ccagcggatt caccttcagc accgactacg cctggaattg ggtgaggcag   120
gcccccggga agggcctgga gtgggtcggc tacatcttct acagcggcag caccacctac   180 accccagcc tgaagagcag gttcaccatc agcagggaca acagcaagaa caccctgtac   240
ctgcagatga acagcctgag ggccgaggac accgccgtgt attactgcgc tagggggggc   300
tacgacgtga actacttcga ctactggggc cagggcacaa ccgtgaccgt gagcagc      357
```

<210> SEQ ID NO 94
<211> LENGTH: 357
<212> TYPE: DNA
<213> ORGANISM: Artificial Sequence
<220> FEATURE:
<223> OTHER INFORMATION: polynucleotide sequence encoding
      6A3.IGHV3_33.H9 VH

<400> SEQUENCE: 94

```
caggtgcagc tggtggagag cggcggcggc gtggtgcagc ccggcaggag cctgaggctc    60
tcttgcgccg ccagcggatt caccttcagc accgactacg cctggaattg ggtgaggcag   120
gcccccggga agggcctgga gtgggtcgcc tacatcttct acagcggcag caccacctac   180 accccagcc tgaagagcag gttcagcatc agcagggaca acagcaagaa caccctgtac   240
ctgcagatga acagcctgag ggccgaggac accgccgtgt attactgcgc tagggggggc   300
tacgacgtga actacttcga ctactggggc cagggcacaa ccgtgaccgt gagcagc      357
```

<210> SEQ ID NO 95
<211> LENGTH: 357
<212> TYPE: DNA
<213> ORGANISM: Artificial Sequence
<220> FEATURE:
<223> OTHER INFORMATION: polynucleotide sequence encoding
      6A3.IGHV3_33.H10 VH

<400> SEQUENCE: 95

```
caggtgcagc tggtggagag cggcggcggc gtggtgcagc ccggcaggag cctgaggctc    60
tcttgcgccg tgagcggatt caccttcagc accgactacg cctggaattg ggtgaggcag   120
```

```
gcccccggga agggcctgga gtgggtcgcc tacatcttct acagcggcag caccacctac    180 accccccagcc tgaagagcag gttcaccatc agcaggaca acagcaagaa cacccctgtac   240 ctgcagatga acagcctgag ggccgaggac accgccgtgt attactgcgc taggggggc    300 tacgacgtga actacttcga ctactggggc cagggcacaa ccgtgaccgt gagcagc       357
```

<210> SEQ ID NO 96
<211> LENGTH: 357
<212> TYPE: DNA
<213> ORGANISM: Artificial Sequence
<220> FEATURE:
<223> OTHER INFORMATION: polynucleotide sequence encoding
    6A3.IGHV3_33.H11 VH

<400> SEQUENCE: 96

```
caggtgcagc tggtggagag cggcggcggc gtggtgcagc ccggcaggag cctgaggctc    60
tcttgcgccg ccagcggatt caccttcagc accgactacg cctggaattg ggtgaggcag   120
gcccccggga agggcctgga gtggatggcc tacatcttct acagcggcag caccacctac    180 accccccagcc tgaagagcag gttcaccatc agcaggaca acagcaagaa cacccctgtac   240 ctgcagatga acagcctgag ggccgaggac accgccgtgt attactgcgc taggggggc    300 tacgacgtga actacttcga ctactggggc cagggcacaa ccgtgaccgt gagcagc       357
```

<210> SEQ ID NO 97
<211> LENGTH: 321
<212> TYPE: DNA
<213> ORGANISM: Artificial Sequence
<220> FEATURE:
<223> OTHER INFORMATION: polynucleotide sequence encoding 6A3.L0 Vk

<400> SEQUENCE: 97

```
gacatccaga tgacccagag ccccagctcc ctgagcgcca gcgtgggcga tagggtgacc    60
atcacctgcc tggccagcca gaccattggc gcctggctgg cctggtacca gcagaagccc   120
ggcaaggccc ccaaactgct gatctacgcc gcaactaggc tcgccgacgg cgtgccctct    180
aggtttagcg gcagcggaag cggcaccgac ttcaccctga ccatcagcag cctgcagccc    240
gaggacttcg ccacctacta ctgccagcag ttcttcagca cccctggac cttcggcggg     300 ggcacaaagg tggagatcaa g                                              321
```

<210> SEQ ID NO 98
<211> LENGTH: 321
<212> TYPE: DNA
<213> ORGANISM: Artificial Sequence
<220> FEATURE:
<223> OTHER INFORMATION: polynucleotide sequence encoding 6A3.L1 Vk

<400> SEQUENCE: 98

```
gacatccaga tgacccagag ccccagctcc ctgagcgcca gcgtgggcga tagggtgacc    60
atcacctgcc tggccagcca gaccattggc gcctggctgg cctggtacca gcagaagccc   120
ggcaaggccc ccagctgct gatctacgcc gcaactaggc tcgccgacgg cgtgccctct    180
aggtttagcg gcagcggaag cggcaccgac ttcaccctga ccatcagcag cctgcagccc    240
gaggacttcg ccacctacta ctgccagcag ttcttcagca cccctggac cttcggcggg     300 ggcacaaagg tggagatcaa g                                              321
```

<210> SEQ ID NO 99
<211> LENGTH: 321

```
<212> TYPE: DNA
<213> ORGANISM: Artificial Sequence
<220> FEATURE:
<223> OTHER INFORMATION: polynucleotide sequence encoding 6A3.L2 Vk

<400> SEQUENCE: 99
gacatccaga tgacccagag ccccagctcc ctgagcgcca gcgtgggcga tagggtgacc      60
atcacctgcc tggccagcca gaccattggc gcctggctgg cctggtacca gcagaagccc     120
ggcaaggccc ccaaactgct gatctacgcc gcaactaggc tcgccgacgg cgtgccctct     180
aggtttagcg gcagcggaag cggcaccaag ttcaccctga ccatcagcag cctgcagccc     240
gaggacttcg ccacctacta ctgccagcag ttcttcagca cccccctgga cttcggcggg     300
ggcacaaagg tggagatcaa g                                               321

<210> SEQ ID NO 100
<211> LENGTH: 321
<212> TYPE: DNA
<213> ORGANISM: Artificial Sequence
<220> FEATURE:
<223> OTHER INFORMATION: polynucleotide sequence encoding 6A3.L3 Vk

<400> SEQUENCE: 100
gacatccaga tgacccagag ccccagctcc ctgagcgcca gcgtgggcga tagggtgacc      60
atcacctgcc tggccagcca gaccattggc gcctggctgg cctggtacca gcagaagccc     120
ggcaaggccc ccagctgct gatctacgcc gcaactaggc tcgccgacgg cgtgccctct      180
aggtttagcg gcagcggaag cggcaccaag ttcaccctga ccatcagcag cctgcagccc     240
gaggacttcg ccacctacta ctgccagcag ttcttcagca cccccctgga cttcggcggg     300
ggcacaaagg tggagatcaa g                                               321

<210> SEQ ID NO 101
<211> LENGTH: 357
<212> TYPE: DNA
<213> ORGANISM: Artificial Sequence
<220> FEATURE:
<223> OTHER INFORMATION: polynucleotide sequence encoding 6A3c VH

<400> SEQUENCE: 101
gacgtccagc tgcaggagag cggcccccggg ctggtgaagc cctctcagag cctgagcctg     60
acctgcaccg tgaccggcta cagcatcacc accgactacg cctggaactg gatcaggcag    120
ttccccggca caagctgga gtggatgggc tacatcttct acagcggcag caccacctat     180
acccccagcc tcaagagcag gatcagcatc accaggaca cctccaagaa ccagttcttc     240
ctgcagctga acagcgtgac cacagaggac accgccacct actactgcgc caggggcgga    300
tacgacgtga actacttcga ctactggggc cagggcacca ctctgaccgt gagcagc       357

<210> SEQ ID NO 102
<211> LENGTH: 321
<212> TYPE: DNA
<213> ORGANISM: Artificial Sequence
<220> FEATURE:
<223> OTHER INFORMATION: polynucleotide sequence encoding 6A3c Vk

<400> SEQUENCE: 102
gacatccaga tgacccagag cccgccagc cagagcgcct ctctgggcga gagcgtgaca      60
atcacctgcc tggccagcca gaccattggc gcttggctgg cctggtacca gcagaagccc    120
ggcaagagcc cccagctgct gatctacgcc gccactaggc tggccgacgg cgtgcccagc    180
```

```
aggtttagcg gcagcggcag cggcaccaag ttcagcttca agatcagcag cctgcaggcc      240
gaggacttcg tgtcctacta ctgccagcag ttcttcagca cccccctggac cttcggcggc     300 ggaaccaaac tcgagatcaa g                                                321
```

```
<210> SEQ ID NO 103
<211> LENGTH: 357
<212> TYPE: DNA
<213> ORGANISM: Artificial Sequence
<220> FEATURE:
<223> OTHER INFORMATION: nucleic acid sequence encoding 1A11.H0

<400> SEQUENCE: 103
caggtgcagc tggtgcagag cggagccgag gtgaagaagc ccggagccag cgtgaaggtg      60
agctgcaaag cctccggcta caccttcacc ggctacacca tgaactgggt caggcaggct     120
cccggccagg gcctggagtg gatgggcctg atcaaccct acaacggcgt gaccagctac     180
aaccagaagt tcaagggcag ggtgaccatg accaggaca ccagcatcag caccgcctac      240
atggaactga gcaggctgag gagcgacgac accgccgtgt attactgcgc caggggcgac     300
gggaactact ggtacttcga cgtatggggc cagggaacaa ccgtgaccgt gagcagc        357
```

```
<210> SEQ ID NO 104
<211> LENGTH: 315
<212> TYPE: DNA
<213> ORGANISM: Artificial Sequence
<220> FEATURE:
<223> OTHER INFORMATION: nucleic acid sequence encoding 1A11.L0

<400> SEQUENCE: 104
gagatcgtgc tgacacagag cccccgccacc ctgtctctga gccctggcga gagggccacc      60
ctgagctgca gcgccagcag cagcgtgacc tacatgcact ggtaccagca gaaacccggc     120
caggcccctc gcctgctgat ctacgagatc tctaagctgg ccagcggcat tcccgctagg     180
ttcagcggca gcggctcagg caccgacttc accctcacca tcagcagcct ggagcccgaa     240
gacttcgccg tctactactg ccaggagtgg aactacccct ataccttcgg cggcgggacc      300
aaggtggaga tcaag                                                       315
```

```
<210> SEQ ID NO 105
<211> LENGTH: 315
<212> TYPE: DNA
<213> ORGANISM: Artificial Sequence
<220> FEATURE:
<223> OTHER INFORMATION: nucleic acid sequence encoding 1A11.L1

<400> SEQUENCE: 105
gagatcgtgc tgactcagag cccccgccacc ctgagcctga gccccggcga aagggccaca      60
ctgagctgca gcgctagcag cagcgtgacc tacatgcact ggtaccagca gaagcccggc     120
caggccccta ggctgtggat ctacgagatc agcaagctgg ccagcggcat tcccgccagg     180
ttctcaggca gcggaagcgg caccgacttc accctcacca tcagctctct ggagcccgag     240
gacttcgccg tctactactg ccaggagtgg aactacccct ataccttcgg cggcggcacc     300
aaggtggaga tcaag                                                       315
```

```
<210> SEQ ID NO 106
<211> LENGTH: 315
<212> TYPE: DNA
<213> ORGANISM: Artificial Sequence
<220> FEATURE:
<223> OTHER INFORMATION: nucleic acid sequence encoding 1A11.L2
```

<400> SEQUENCE: 106

```
gagatcgtgc tgacccagag ccccgcaacc ctgagcctca gccctggcga gagggccact    60
ctgagctgct ctgccagcag cagcgtgacc tacatgcact ggtaccagca gaagcccgga   120
caggccccca ggctgctgat ctacgagatc agcaagctgg cctctggcat tcccgccagg   180
ttcagcggct caggcagcgg caccgactac accctgacca tcagcagcct ggaacccgag   240
gacttcgccg tctactactg ccaggagtgg aactatccct acaccttcgg cggcggcacc   300
aaggtggaga tcaag                                                    315
```

<210> SEQ ID NO 107
<211> LENGTH: 315
<212> TYPE: DNA
<213> ORGANISM: Artificial Sequence
<220> FEATURE:
<223> OTHER INFORMATION: nucleic acid sequence encoding 1A11.L3

<400> SEQUENCE: 107

```
gagatcgtgc tgacccagag ccccgccaca ctgtcactgt ctcccggcga aagggccacc    60
ctgagctgca gcgcctctag cagcgtgacc tacatgcact ggtaccagca gaagcccggc   120
caggctccca ggctgtggat ctacgagatc agcaagctgg ccagcggcat ccctgccagg   180
ttcagcggca gcggcagcgg caccgactat accctgacca tcagcagcct cgagcccgag   240
gacttcgccg tctactactg ccaggagtgg aactaccct acaccttcgg cggcgggacc   300
aaagtggaga tcaag                                                    315
```

<210> SEQ ID NO 108
<211> LENGTH: 315
<212> TYPE: DNA
<213> ORGANISM: Artificial Sequence
<220> FEATURE:
<223> OTHER INFORMATION: nucleic acid sequence encoding 1A11.L4

<400> SEQUENCE: 108

```
gaaattgtgc tgacccagag ccccgccacc ctgagcctgt caccaggcga gagggcaact    60
ctgagctgca gcgccagctc tagcgtgacc tacatgcact ggtaccagca gaaacccgga   120
caggcccccc ggccccctgat ctacgagatc tccaagctgg ccagcggcat ccccgccagg   180
tttagcggca gcggcagcgg caccgacttc accctgacca tcagcagcct cgagcccgag   240
gacttcgccg tgtattactg ccaggagtgg aactaccct acaccttcgg cggcggcacc   300
aaggtggaga tcaag                                                    315
```

<210> SEQ ID NO 109
<211> LENGTH: 315
<212> TYPE: DNA
<213> ORGANISM: Artificial Sequence
<220> FEATURE:
<223> OTHER INFORMATION: nucleic acid sequence encoding 1A11.L5

<400> SEQUENCE: 109

```
gaaatcgtgc tgacccagag ccccgcaacc ctgagcctga gccccggaga gagggccact    60
ctgagctgca gcgccagcag cagcgtgacc tacatgcact ggtaccagca gaagcccggc   120
caggccccaa ggccctggat ctacgagatt agcaagctgg cctccggcat ccctgccagg   180
ttcagcggct caggcagcgg caccgactat accctcacca tcagcagcct ggagcccgag   240
gacttcgccg tctactactg ccaggagtgg aactaccct acaccttcgg cggcggcacc   300
```

```
aaggtggaga tcaag                                                     315

<210> SEQ ID NO 110
<211> LENGTH: 315
<212> TYPE: DNA
<213> ORGANISM: Artificial Sequence
<220> FEATURE:
<223> OTHER INFORMATION: nucleic acid sequence encoding 1A11.L6

<400> SEQUENCE: 110
gagatcgtgc tgacccagtc acccgcaaca ctgagcctga gcccaggaga gagggccacc    60
ctgagctgca gcgcctctag ctccgtgacc tacatgcact ggtaccagca gaagcccggc   120
caggccccca gaccctggat ctacgagatc agcaagctcg ccagcggcgt ccccgccagg   180
ttcagcggaa gcggcagcgg gaccgactac accctgacca tcagcagcct ggaacccgag   240
gacttcgccg tgtattactg ccaggagtgg aactacccct acaccttcgg cggcggcacc   300
aaggtggaga tcaag                                                     315

<210> SEQ ID NO 111
<211> LENGTH: 315
<212> TYPE: DNA
<213> ORGANISM: Artificial Sequence
<220> FEATURE:
<223> OTHER INFORMATION: nucleic acid sequence encoding 1A11.L7

<400> SEQUENCE: 111
gaaattgtgc tgacccagag ccccgccacc ctgagcctgt caccaggcga gagggcaact    60
ctgagctgca gcgccagctc tagcgtgacc tacatgcact ggtaccagca gaaacccgga   120
caggccccca gccctggat ctacgagatc tccaagctgg ccagcggcgt gcccgccagg    180
tttagcggca gcggcagcgg caccgactac accctgacca tcagcagcct cgagcccgag   240
gacttcgccg tgtattactg ccaggagtgg aactacccct acaccttcgg cggcggcacc   300
aaggtggaga tcaag                                                     315

<210> SEQ ID NO 112
<211> LENGTH: 315
<212> TYPE: DNA
<213> ORGANISM: Artificial Sequence
<220> FEATURE:
<223> OTHER INFORMATION: nucleic acid sequence encoding 1A11.L8

<400> SEQUENCE: 112
gaaatcgtgc tgacccagag ccccgcaacc ctgagcctga gccccggaga gagggccact    60
ctgagctgca gcgccagcag cagcgtgacc tacatgcact ggtaccagca gaagcccggc   120
caggccccaa agccctggat ctacgagatt agcaagctgg cctccggcgt ccctgccagg   180
ttcagcggct caggcagcgg cacctcctat accctcacca tcagcagcct ggagcccgag   240
gacttcgccg tctactactg ccaggagtgg aactacccct acaccttcgg cggcggcacc   300
aaggtggaga tcaag                                                     315

<210> SEQ ID NO 113
<211> LENGTH: 315
<212> TYPE: DNA
<213> ORGANISM: Artificial Sequence
<220> FEATURE:
<223> OTHER INFORMATION: nucleic acid sequence encoding 1A11.L9

<400> SEQUENCE: 113
gagatcgtgc tgacccagtc acccgcaaca ctgagcctga gcccaggaga gagggccacc    60
```

```
ctgagctgca gcgcctctag ctccgtgacc tacatgcact ggtaccagca gaagcccggc    120 caggcccca agccctggat ctacgagatc agcaagctcg ccagcggcgt ccccgtcagg    180
ttcagcggaa gcggcagcgg gaccagctac accctgacca tcagcagcct ggaacccgag    240
gacttcgccg tgtattactg ccaggagtgg aactacccct acaccttcgg cggcggcacc    300
aaggtggaga tcaag                                                    315
```

<210> SEQ ID NO 114
<211> LENGTH: 449
<212> TYPE: PRT
<213> ORGANISM: Artificial Sequence
<220> FEATURE:
<223> OTHER INFORMATION: 1A11.H3FL (Full length)

<400> SEQUENCE: 114

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
             20                  25                  30

Thr Met Asn Trp Val Arg Gln Ala Pro Gly Gln Gly Leu Glu Trp Met
         35                  40                  45

Gly Leu Ile Asn Pro Tyr Asn Gly Val Thr Ser Tyr Asn Gln Lys Phe
     50                  55                  60

Lys Gly Arg Val Thr Leu Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Gly Asp Gly Asn Tyr Trp Tyr Phe Asp Val Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
```

```
            305                 310                 315                 320
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 115
<211> LENGTH: 212
<212> TYPE: PRT
<213> ORGANISM: Artificial Sequence
<220> FEATURE:
<223> OTHER INFORMATION: 1A11.L4FL (Full length)

<400> SEQUENCE: 115

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Thr Tyr Met
            20                  25                  30

His Trp Tyr Gln Gln Lys Pro Gly Gln Ala Pro Arg Pro Leu Ile Tyr
        35                  40                  45

Glu Ile Ser Lys Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Glu Trp Asn Tyr Pro Tyr Thr Phe
                85                  90                  95

Gly Gly Gly Thr Lys Val Glu Ile Lys Arg Thr Val Ala Ala Pro Ser
            100                 105                 110

Val Phe Ile Phe Pro Pro Ser Asp Glu Gln Leu Lys Ser Gly Thr Ala
        115                 120                 125

Ser Val Val Cys Leu Leu Asn Asn Phe Tyr Pro Arg Glu Ala Lys Val
    130                 135                 140

Gln Trp Lys Val Asp Asn Ala Leu Gln Ser Gly Asn Ser Gln Glu Ser
145                 150                 155                 160

Val Thr Glu Gln Asp Ser Lys Asp Ser Thr Tyr Ser Leu Ser Ser Thr
                165                 170                 175

Leu Thr Leu Ser Lys Ala Asp Tyr Glu Lys His Lys Val Tyr Ala Cys
            180                 185                 190

Glu Val Thr His Gln Gly Leu Ser Ser Pro Val Thr Lys Ser Phe Asn
        195                 200                 205

Arg Gly Glu Cys
    210
```

<210> SEQ ID NO 116
<211> LENGTH: 117
<212> TYPE: PRT
<213> ORGANISM: Homo sapiens

<400> SEQUENCE: 116

Met Asp Trp Thr Trp Arg Ile Leu Phe Leu Val Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Gly Tyr Tyr Met His Trp Val Arg Gln Ala Pro Gly Gln Gly Leu
    50                  55                  60

Glu Trp Met Gly Trp Ile Asn Pro Asn Ser Gly Gly Thr Asn Tyr Ala
65                  70                  75                  80

Gln Lys Phe Gln Gly Arg Val Thr Met Thr Arg Asp Thr Ser Ile Ser
                85                  90                  95

Thr Ala Tyr Met Glu Leu Ser Arg Leu Arg Ser Asp Asp Thr Ala Val
            100                 105                 110

Tyr Tyr Cys Ala Arg
        115

<210> SEQ ID NO 117
<211> LENGTH: 113
<212> TYPE: PRT
<213> ORGANISM: Homo sapiens

<400> SEQUENCE: 117

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Asn Arg Ala Thr Gly Ile Pro Ala Arg Phe
65                  70                  75                  80

Ser Gly Ser Gly Ser Gly Thr Asp Phe Thr Leu Thr Ile Ser Ser Leu
                85                  90                  95

Glu Pro Glu Asp Phe Ala Val Tyr Tyr Cys Gln Gln Arg Ser Asn Trp
            100                 105                 110

Pro

<210> SEQ ID NO 118
<211> LENGTH: 449
<212> TYPE: PRT
<213> ORGANISM: Artificial Sequence
<220> FEATURE:
<223> OTHER INFORMATION: 1A11_H3-Fc (FULL LENGTH)

<400> SEQUENCE: 118

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

```
Thr Met Asn Trp Val Arg Gln Ala Pro Gly Gln Gly Leu Glu Trp Met
         35                  40                  45
Gly Leu Ile Asn Pro Tyr Asn Gly Val Thr Ser Tyr Asn Gln Lys Phe
 50                  55                  60
Lys Gly Arg Val Thr Leu Thr Arg Asp Thr Ser Ile Ser Thr Ala Tyr
 65                  70                  75                  80
Met Glu Leu Ser Arg Leu Arg Ser Asp Thr Ala Val Tyr Tyr Cys
                 85                  90                  95
Ala Arg Gly Asp Gly Asn Tyr Trp Tyr Phe Asp Val Trp Gly Gln Gly
                100                 105                 110
Thr Thr Val Thr Val Ser Ser Ala Ser Thr Lys Gly Pro Ser Val Phe
                115                 120                 125
Pro Leu Ala Pro Ser Ser Lys Ser Thr Ser Gly Gly Thr Ala Ala Leu
            130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
                180                 185                 190
Ser Ser Leu Gly Thr Gln Thr Tyr Ile Cys Asn Val Asn His Lys Pro
            195                 200                 205
Ser Asn Thr Lys Val Asp Lys Lys Val Glu Pro Lys Ser Cys Asp Lys
            210                 215                 220
Thr His Thr Cys Pro Pro Cys Pro Ala Pro Glu Leu Ala Gly Ala Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
                260                 265                 270
Pro Glu Val Lys Phe Asn Trp Tyr Val Asp Gly Val Glu Val His Asn
            275                 280                 285
Ala Lys Thr Lys Pro Arg Glu Glu Gln Tyr Asn Ser Thr Tyr Arg Val
            290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
            355                 360                 365
Cys Leu Val Lys Gly Phe Tyr Pro Ser Asp Ile Ala Val Glu Trp Glu
370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
            435                 440                 445
```

Lys

<210> SEQ ID NO 119
<211> LENGTH: 1407
<212> TYPE: DNA
<213> ORGANISM: Artificial Sequence
<220> FEATURE:
<223> OTHER INFORMATION: 1A11_VH3-Fc DNA (FULL LENGTH, WITH SIGNAL
      SEQUENCE)

<400> SEQUENCE: 119

| | | | | | |
|---|---|---|---|---|---|
| atgggctggt | cctgcatcat | cctgtttctg | gtggccaccg | ccaccggtgt | gcacagccag | 60 |
| gtgcagctgg | tgcagagcgg | agccgaggtg | aagaaacccg | gagccagcgt | gaaggtgagc | 120 |
| tgcaaggcca | gcggctacac | cttcaccggc | tacaccatga | actgggtgag | gcaggccccc | 180 |
| ggccagggac | tcgagtggat | gggcctgatc | aaccccatca | acggcgtgac | cagctacaac | 240 |
| cagaagttca | agggcagggt | gaccctgacc | agggatacca | gcatcagcac | cgcttacatg | 300 |
| gaactgagca | gcctgaggtc | cgacgacacc | gccgtgtatt | actgcgccag | ggcgacggc | 360 |
| aactactggt | acttcgatgt | gtggggccag | ggcaccaccg | tcacagtgag | cagcgccagc | 420 |
| accaagggcc | ccagcgtgtt | cccccctggcg | cccagcagca | agagcaccag | cggcggcaca | 480 |
| gccgccctgg | gctgcctggt | gaaggactac | ttccccgagc | cagtgaccgt | gtcctggaac | 540 |
| agcggagccc | tgaccagcgg | cgtgcacacc | ttcccagctg | tcctgcagag | cagcggcctg | 600 |
| tacagcctga | gcagcgtggt | gaccgtgccc | agcagcagcc | tgggcaccca | gacctacatc | 660 |
| tgtaacgtga | accacaagcc | cagcaacacc | aaggtggaca | agaaggtgga | gcccaagagc | 720 |
| tgtgacaaga | cccacacctg | ccccccctgc | cctgcccccg | agctggccgg | agcccccagc | 780 |
| gtgttcctgt | tccccccaa | gcctaaggac | accctgatga | tcagcagaac | ccccgaggtg | 840 |
| acctgtgtgg | tggtggatgt | gagccacgag | gaccctgagg | tgaagttcaa | ctggtacgtg | 900 |
| gacggcgtgg | aggtgcacaa | tgccaagacc | aagcccaggg | aggagcagta | caacagcacc | 960 |
| taccgggtgg | tgtccgtgct | gaccgtgctg | caccaggatt | ggctgaacgg | caaggagtac | 1020 |
| aagtgtaagg | tgtccaacaa | ggccctgcct | gcccctatcg | agaaaaccat | cagcaaggcc | 1080 |
| aagggccagc | ccagagagcc | ccaggtgtac | accctgcccc | ctagcagaga | tgagctgacc | 1140 |
| aagaaccagg | tgtccctgac | ctgcctggtg | aagggcttct | accccagcga | catcgccgtg | 1200 |
| gagtgggaga | gcaacggcca | gcccgagaac | aactacaaga | ccaccccccc | tgtgctggac | 1260 |
| agcgatggca | gcttcttcct | gtacagcaag | ctgaccgtgg | acaagagcag | atggcagcag | 1320 |
| ggcaacgtgt | tcagctgctc | cgtgatgcac | gaggccctgc | acaatcacta | cacccagaag | 1380 |
| agcctgagcc | tgtcccctgg | caagtga | | | | 1407 |

<210> SEQ ID NO 120
<211> LENGTH: 357
<212> TYPE: DNA
<213> ORGANISM: Artificial Sequence
<220> FEATURE:
<223> OTHER INFORMATION: nucleic acid encoding 1A11 VH3 N98D

<400> SEQUENCE: 120

| | | | | | |
|---|---|---|---|---|---|
| caggtgcagc | tggtgcagag | cggagccgag | gtgaagaaac | ccggagccag | cgtgaaggtg | 60 |
| agctgcaagg | ccagcggcta | caccttcacc | ggctacacca | tgaactgggt | gaggcaggcc | 120 |
| cccggccagg | gactcgagtg | gatgggcctg | atcaacccct | acaacggcgt | gaccagctac | 180 |
| aaccagaagt | tcaagggcag | ggtgaccctg | accagggata | ccagcatcag | caccgcttac | 240 |

```
atggaactga gcaggctgag gtccgacgac accgccgtgt attactgcgc cagggggcgac    300 ggcgactact ggtacttcga tgtgtggggc cagggcacca ccgtcacagt gagcagc        357
```

<210> SEQ ID NO 121
<211> LENGTH: 119
<212> TYPE: PRT
<213> ORGANISM: Artificial Sequence
<220> FEATURE:
<223> OTHER INFORMATION: 1A11 VH3 N98D

<400> SEQUENCE: 121

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Thr Met Asn Trp Val Arg Gln Ala Pro Gly Gln Gly Leu Glu Trp Met
        35                  40                  45

Gly Leu Ile Asn Pro Tyr Asn Gly Val Thr Ser Tyr Asn Gln Lys Phe
    50                  55                  60

Lys Gly Arg Val Thr Leu Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Asp Gly Asp Tyr Trp Tyr Phe Asp Val Trp Gly Gln Gly
            100                 105                 110

Thr Thr Val Thr Val Ser Ser
        115
```

<210> SEQ ID NO 122
<211> LENGTH: 357
<212> TYPE: DNA
<213> ORGANISM: Artificial Sequence
<220> FEATURE:
<223> OTHER INFORMATION: nucleic acid encoding 1A11 VH3 N98E

<400> SEQUENCE: 122

```
caggtgcagc tggtgcagag cggagccgag gtgaagaaac ccggagccag cgtgaaggtg    60
agctgcaagg ccagcggcta caccttcacc ggctacacca tgaactgggt gaggcaggcc   120
cccggccagg gactcgagtg gatgggcctg atcaacccct acaacggcgt gaccagctac   180
aaccagaagt tcaagggcag ggtgaccctg accagggata ccagcatcag caccgcttac   240
atggaactga gcaggctgag gtccgacgac accgccgtgt attactgcgc cagggggcgac   300 ggcgagtact ggtacttcga tgtgtggggc cagggcacca ccgtcacagt gagcagc       357
```

<210> SEQ ID NO 123
<211> LENGTH: 119
<212> TYPE: PRT
<213> ORGANISM: Artificial Sequence
<220> FEATURE:
<223> OTHER INFORMATION: 1A11 VH3 N98E

<400> SEQUENCE: 123

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Thr Met Asn Trp Val Arg Gln Ala Pro Gly Gln Gly Leu Glu Trp Met
        35                  40                  45
```

```
Gly Leu Ile Asn Pro Tyr Asn Gly Val Thr Ser Tyr Asn Gln Lys Phe
        50                  55                  60

Lys Gly Arg Val Thr Leu Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                85                  90                  95

Ala Arg Gly Asp Gly Glu Tyr Trp Tyr Phe Asp Val Trp Gly Gln Gly
                100                 105                 110

Thr Thr Val Thr Val Ser Ser
            115
```

<210> SEQ ID NO 124
<211> LENGTH: 357
<212> TYPE: DNA
<213> ORGANISM: Artificial Sequence
<220> FEATURE:
<223> OTHER INFORMATION: nucleic acid encoding 1A11 VH3 F100bE

<400> SEQUENCE: 124

```
caggtgcagc tggtgcagag cggagccgag gtgaagaaac ccggagccag cgtgaaggtg    60
agctgcaagg ccagcggcta caccttcacc ggctacacca tgaactgggt gaggcaggcc   120
cccggccagg gactcgagtg gatgggcctg atcaacccct acaacggcgt gaccagctac   180
aaccagaagt tcaagggcag ggtgacccta accagggata ccagcatcag caccgcttac   240
atggaactga gcaggctgag gtccgacgac accgccgtgt attactgcgc caggggcgac   300
ggcaactact ggtacgagga tgtgtggggc cagggcacca ccgtcacagt gagcagc      357
```

<210> SEQ ID NO 125
<211> LENGTH: 119
<212> TYPE: PRT
<213> ORGANISM: Artificial Sequence
<220> FEATURE:
<223> OTHER INFORMATION: 1A11 VH3 F100bE

<400> SEQUENCE: 125

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
                20                  25                  30

Thr Met Asn Trp Val Arg Gln Ala Pro Gly Gln Gly Leu Glu Trp Met
            35                  40                  45

Gly Leu Ile Asn Pro Tyr Asn Gly Val Thr Ser Tyr Asn Gln Lys Phe
        50                  55                  60

Lys Gly Arg Val Thr Leu Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                85                  90                  95

Ala Arg Gly Asp Gly Asn Tyr Trp Tyr Glu Asp Val Trp Gly Gln Gly
                100                 105                 110

Thr Thr Val Thr Val Ser Ser
            115
```

<210> SEQ ID NO 126
<211> LENGTH: 357
<212> TYPE: DNA
<213> ORGANISM: Artificial Sequence
<220> FEATURE:
<223> OTHER INFORMATION: nucleic acid encoding VH3 F100bH

<400> SEQUENCE: 126

```
caggtgcagc tggtgcagag cggagccgag gtgaagaaac ccggagccag cgtgaaggtg    60
agctgcaagg ccagcggcta caccttcacc ggctacacca tgaactgggt gaggcaggcc   120
cccggccagg gactcgagtg gatgggcctg atcaaccct acaacggcgt gaccagctac    180
aaccagaagt tcaagggcag ggtgaccctg accagggata ccagcatcag caccgcttac   240
atggaactga gcaggctgag gtccgacgac accgccgtgt attactgcgc caggggcgac   300
ggcaactact ggtaccacga tgtgtggggc cagggcacca ccgtcacagt gagcagc      357
```

<210> SEQ ID NO 127
<211> LENGTH: 119
<212> TYPE: PRT
<213> ORGANISM: Artificial Sequence
<220> FEATURE:
<223> OTHER INFORMATION: 1A11 VH3 F100bH

<400> SEQUENCE: 127

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Gly Tyr
             20                  25                  30

Thr Met Asn Trp Val Arg Gln Ala Pro Gly Gln Gly Leu Glu Trp Met
         35                  40                  45

Gly Leu Ile Asn Pro Tyr Asn Gly Val Thr Ser Tyr Asn Gln Lys Phe
     50                  55                  60

Lys Gly Arg Val Thr Leu Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Gly Asp Gly Asn Tyr Trp Tyr His Asp Val Trp Gly Gln Gly
                100                 105                 110

Thr Thr Val Thr Val Ser Ser
        115
```

<210> SEQ ID NO 128
<211> LENGTH: 357
<212> TYPE: DNA
<213> ORGANISM: Artificial Sequence
<220> FEATURE:
<223> OTHER INFORMATION: nucleic acid encoding VH3 F100bI

<400> SEQUENCE: 128

```
caggtgcagc tggtgcagag cggagccgag gtgaagaaac ccggagccag cgtgaaggtg    60
agctgcaagg ccagcggcta caccttcacc ggctacacca tgaactgggt gaggcaggcc   120
cccggccagg gactcgagtg gatgggcctg atcaaccct acaacggcgt gaccagctac    180
aaccagaagt tcaagggcag ggtgaccctg accagggata ccagcatcag caccgcttac   240
atggaactga gcaggctgag gtccgacgac accgccgtgt attactgcgc caggggcgac   300
ggcaactact ggtacatcga tgtgtggggc cagggcacca ccgtcacagt gagcagc      357
```

<210> SEQ ID NO 129
<211> LENGTH: 119
<212> TYPE: PRT
<213> ORGANISM: Artificial Sequence
<220> FEATURE:
<223> OTHER INFORMATION: VH3 F100bI

<400> SEQUENCE: 129

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Thr Met Asn Trp Val Arg Gln Ala Pro Gly Gln Gly Leu Glu Trp Met
            35                  40                  45

Gly Leu Ile Asn Pro Tyr Asn Gly Val Thr Ser Tyr Asn Gln Lys Phe
        50                  55                  60

Lys Gly Arg Val Thr Leu Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Asp Gly Asn Tyr Trp Tyr Ile Asp Val Trp Gly Gln Gly
                100                 105                 110

Thr Thr Val Thr Val Ser Ser
        115

<210> SEQ ID NO 130
<211> LENGTH: 357
<212> TYPE: DNA
<213> ORGANISM: Artificial Sequence
<220> FEATURE:
<223> OTHER INFORMATION: nucleic acid encoding VH3 F100bV

<400> SEQUENCE: 130
caggtgcagc tggtgcagag cggagccgag gtgaagaaac ccggagccag cgtgaaggtg        60
agctgcaagg ccagcggcta caccttcacc ggctacacca tgaactgggt gaggcaggcc       120
cccggccagg gactcgagtg gatgggcctg atcaacccct acaacggcgt gaccagctac       180
aaccagaagt tcaagggcag ggtgaccctg accaggata ccagcatcag caccgcttac        240
atggaactga gcaggctgag gtccgacgac accgccgtgt attactgcgc caggggcgac       300
ggcaactact ggtacgtgga tgtgtggggc cagggcacca ccgtcacagt gagcagc          357

<210> SEQ ID NO 131
<211> LENGTH: 119
<212> TYPE: PRT
<213> ORGANISM: Artificial Sequence
<220> FEATURE:
<223> OTHER INFORMATION: VH3 F100bV

<400> SEQUENCE: 131

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Thr Met Asn Trp Val Arg Gln Ala Pro Gly Gln Gly Leu Glu Trp Met
            35                  40                  45

Gly Leu Ile Asn Pro Tyr Asn Gly Val Thr Ser Tyr Asn Gln Lys Phe
        50                  55                  60

Lys Gly Arg Val Thr Leu Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Asp Gly Asn Tyr Trp Tyr Val Asp Val Trp Gly Gln Gly
                100                 105                 110

Thr Thr Val Thr Val Ser Ser

```
              115

<210> SEQ ID NO 132
<211> LENGTH: 10
<212> TYPE: PRT
<213> ORGANISM: Artificial Sequence
<220> FEATURE:
<223> OTHER INFORMATION: VH3 N98D CDRH3

<400> SEQUENCE: 132

Gly Asp Gly Asp Tyr Trp Tyr Phe Asp Val
1               5                   10

<210> SEQ ID NO 133
<211> LENGTH: 10
<212> TYPE: PRT
<213> ORGANISM: Artificial Sequence
<220> FEATURE:
<223> OTHER INFORMATION: VH3 N98E CDRH3

<400> SEQUENCE: 133

Gly Asp Gly Glu Tyr Trp Tyr Phe Asp Val
1               5                   10

<210> SEQ ID NO 134
<211> LENGTH: 10
<212> TYPE: PRT
<213> ORGANISM: Artificial Sequence
<220> FEATURE:
<223> OTHER INFORMATION: VH3 F100bE CDRH3

<400> SEQUENCE: 134

Gly Asp Gly Asn Tyr Trp Tyr Glu Asp Val
1               5                   10

<210> SEQ ID NO 135
<211> LENGTH: 10
<212> TYPE: PRT
<213> ORGANISM: Artificial Sequence
<220> FEATURE:
<223> OTHER INFORMATION: VH3 F100bH CDRH3

<400> SEQUENCE: 135

Gly Asp Gly Asn Tyr Trp Tyr His Asp Val
1               5                   10

<210> SEQ ID NO 136
<211> LENGTH: 10
<212> TYPE: PRT
<213> ORGANISM: Artificial Sequence
<220> FEATURE:
<223> OTHER INFORMATION: VH3 F100bI CDRH3

<400> SEQUENCE: 136

Gly Asp Gly Asn Tyr Trp Tyr Ile Asp Val
1               5                   10

<210> SEQ ID NO 137
<211> LENGTH: 10
<212> TYPE: PRT
<213> ORGANISM: Artificial Sequence
<220> FEATURE:
<223> OTHER INFORMATION: VH3 F100bV CDRH3

<400> SEQUENCE: 137

Gly Asp Gly Asn Tyr Trp Tyr Val Asp Val
1               5                   10
```

```
<210> SEQ ID NO 138
<211> LENGTH: 107
<212> TYPE: PRT
<213> ORGANISM: Artificial Sequence
<220> FEATURE:
<223> OTHER INFORMATION: 6A3.L27 Vk

<400> SEQUENCE: 138

Asp Ile Gln Met Leu Gln Ser Pro Ser Ser Leu Ser Ala Ser Val Gly
1               5                   10                  15

Asp Arg Val Thr Ile Thr Cys Leu Ala Ser Gln Thr Ile Gly Tyr Trp
                20                  25                  30

Leu Ala Trp Tyr Gln Gln Lys Pro Gly Lys Ala Pro Lys Leu Leu Ile
            35                  40                  45

Tyr Ala Ala Thr Arg Leu Ala Asp Gly Val Pro Ser Arg Phe Ser Gly
        50                  55                  60

Ser Gly Ser Gly Thr Met Phe Thr Leu Thr Ile Ser Ser Leu Gln Pro
65                  70                  75                  80

Glu Asp Phe Ala Thr Tyr Tyr Cys Gln Gln Phe Phe Ser Tyr Pro Trp
                85                  90                  95

Thr Phe Gly Gly Gly Thr Lys Val Glu Ile Lys
                100                 105
```

CD127 BINDING PROTEINS

This application is a 371 of International Application No. PCT/US2011/022507, filed 26 Jan. 2011, which claims the benefit of U.S. Provisional Application No. 61/299,010, filed 28 Jan. 2010, both of which are herein incorporated by reference in their entireties.

FIELD OF THE INVENTION

The present invention relates to antigen binding proteins, in particular immunoglobulins, that specifically bind to the α-chain of the human IL-7 receptor (CD127). The invention also concerns methods of treating diseases or disorders with said proteins, pharmaceutical compositions comprising said proteins and methods of their manufacture. Other aspects of the present invention will be apparent from the description below.

BACKGROUND OF THE INVENTION

Multiple Sclerosis (MS) is a chronic inflammatory, demyelinating disease that affects the central nervous system. In MS, it is believed that infiltrating inflammatory immune cells are involved in the destruction of oligodendrocytes, which are the cells responsible for creating and maintaining a fatty layer, known as the myelin sheath. MS results in the thinning or complete loss of myelin. When the myelin is lost, the neurons can no longer effectively conduct their electrical signals leading to numerous neurologic dysfunctions. Individuals with MS produce autoreactive T cells that participate in the formation of inflammatory lesions along the myelin sheath of nerve fibres. The cerebrospinal fluid of patients with active MS contains activated T cells, which infiltrate the brain tissue and cause characteristic inflammatory lesions, destroying the myelin. While the multiple sclerosis symptoms and course of illness can vary from person to person, there are three principle forms of the disease—relapsing-remitting MS, secondary progressive MS, and primary progressive MS.

In the early stages of MS, inflammatory attacks occur over short intervals of acutely heightened disease activity. These episodes are followed by periods of recovery and remission. During the remission period, the local swelling in the nervous system lesion resolves, the immune cells become less active or inactive, and the myelin-producing cells remyelinate the axons. Nerve signalling improves, and the disability caused by the inflammation becomes less severe or goes away entirely. This phase of the disease is called relapsing-remitting MS (RRMS). The lesions do not all heal completely, though. Some remain as "chronic" lesions, which usually have a demyelinated core region which lacks immune cells. Over time, the cells in the centre of such lesions mostly die, although inflammation often continues at their edges. The brain can adapt well to the loss of some neurons, and permanent disability may not occur for many years. However, more than 50% of patients with MS eventually enter a stage of progressive deterioration, called secondary progressive MS (SPMS). In this stage, the disease no longer responds well to disease-modifying drugs, and patients' disabilities steadily worsen. The destruction of neurons from early in the natural course of MS suggests that the progressive disabilities of SPMS might be the result of an accumulated neuronal loss that eventually overwhelms the brain's compensatory abilities. Primary progressive MS is a type of multiple sclerosis where there are no relapses, but over a period of years, there is gradual loss of physical and cognitive functions.

The goal of treatment in patients with relapsing-remitting multiple sclerosis is to reduce the frequency and severity of relapses (and thereby prevent exacerbations) as well as to prevent or postpone the onset of the progressive phase of the disease. To achieve this goal, in the past especially, immunomodulatory or immunosuppressive drugs have been used, but they have never found widespread acceptance owing to limited efficacy and considerable toxicity. For example, large randomized controlled trials have been performed successfully with interferon beta-1a, interferon beta-1 b, and glatiramer acetate.

Both altered autoimmune T cell responses and dysfunction of the regulatory network of the immune system play an important role in human autoimmune pathologies, such as MS and rheumatoid arthritis (Kuchroo et al., (2002) Annu. Rev. Immunol. 20:101-123; Sospedra and Martin (2005) Annu. Rev. Immunol. 23: 683-747; Toh and Miossec (2007) Curr. Opin. Rheumatol. 19:284-288).

Although the aetiology and pathogenesis of MS remain unknown, it is generally considered an autoimmune pathology in which autoreactive T cells of pathogenic potential, such as $T_H1$ and $T_H17$ cells, are thought to play an important role. There is evidence that these effector T cells are activated in vivo during the disease process and are attributable to the central nervous system (CNS) inflammation. There is also evidence that these T cells mediate destruction of myelin-expressing cells in lesions of EAE and MS during the active phase of the disease. On the other hand, regulatory T cells ($T_{reg}$) that normally keep pathogenic $T_H1$ and $T_H17$ cells in check are deficient in patients with MS, further tilting the immune system toward an pro-inflammatory state.

Three separate groups recently reported the results of genome wide single nucleotide polymorphisms (SNPs) scanning in a total of 17,947 donors with or without MS. After scanning 334,923 SNPs, they found a highly significant association (overall $P=2.9\times10^{-7}$) of a nonsynonymous coding SNP in the human IL-7 receptor alpha chain (IL-7Rα) with MS susceptibility. The SNP corresponds to a change from T to C in exon 6 of CD127 (also known as IL-7Rα). This change enhances the chance of exon 6 skipping during RNA splicing, resulting in a soluble form of CD127. Furthermore, expressions of CD127 and IL-7 RNAs in the cerebrospinal fluids (CSFs) of MS patients are significantly higher relative to CSFs of patients with other neurological disorders.

IL-7 and IL-7 receptor (IL-7R) are known to play an important role in T cell and B cell development and homeostasis mainly in a thymic environment. Indeed, thymic stromal cells, fetal thymus, and bone marrow are sites of IL-7 of production. The IL-7 receptor consists of two subunits, CD127 and a common chain (gamma chain or γc) which is shared by receptors of IL-2, IL-4, IL-9, IL-15, and IL-21.

CD127 is also known as IL-7 receptor alpha (IL-7Rα) and p90 IL-7R. Human CD127 (Swiss Prot accession number P16871) has a total of 459 amino acids (20 signal sequence). It comprises a 219 amino acid extra cellular region, a 25 amino acid transmembrane region and a 195 amino acid intracellular region. The numbering of residues within CD127, as used herein (e.g. for the description of antibody epitopes) is based on the full length protein, including signal sequence residues. CD127 may exist in four isoforms, the isoform H20 (Swissprot accession number P16871-1) has the following amino acid sequence (including signal sequence):

(SEQ ID NO: 1)
```
MTILGTTFGM VFSLLQVVSG ESGYAQNGDL EDAELDDYSF
SCYSQLEVNG SQHSLTCAFE
```

-continued

```
DPDVNTTNLE FEICGALVEV KCLNFRKLQE IYFIETKKFL
LIGKSNICVK VGEKSLTCKK

IDLTTIVKPE APFDLSVIYR EGANDFVVTF NTSHLQKKYV
KVLMHDVAYR QEKDENKWTH

VNLSSTKLTL LQRKLQPAAM YEIKVRSIPD HYFKGFWSEW
SPSYYFRTPE INNSSGEMDP

ILLTISILSF FSVALLVILA CVLWKKRIKP IVWPSLPDHK
KTLEHLCKKP RKNLNVSFNP

ESFLDCQIHR VDDIQARDEV EGFLQDTFPQ QLEESEKQRL
GGDVQSPNCP SEDVVVTPES

FGRDSSLTCL AGNVSACDAP ILSSSRSLDC RESGKNGPHV
YQDLLLSLGT TNSTLPPPFS

LQSGILTLNP VAQGQPILTS LGSNQEEAYV TMSSFYQNQ
```

CD127 is also found in the receptor of thymic stromal derived lymphopoietin (TSLP). The TSLP receptor is a heterodimer of CD127 and cytokine receptor-like factor 2 (CRLF2).

Binding of IL-7 to the IL-7R activates multiple signalling pathways including the activation of JAK kinases 1 and 3 leading to the phosphorylation and activation of Stat5. This pathway is crucial to the survival of thymic developing T cell precursors because Stat5 activation is required in the induction of the anti-apoptotic protein Bcl-2 and the prevention of the pro-apoptotic protein Bax entry into the mitochondrion. Another IL-7R mediated pathway is the activation of PI3 kinase, resulting in the phosphorylation of the pro-apoptotic protein Bad and its cytoplasm retention. CD127 is expressed in peripheral resting and memory T cells. The mechanism of IL-7 regulation of T cell survival and homeostasis and the source of IL-7 in the periphery are not completely understood. Furthermore, its potential role in the differentiation and function of pathogenic T cells in autoimmune disease is poorly studied and largely unknown. There are few reports suggesting that IL-7 may contribute to the pathogenesis of autoimmune diseases.

Recently, Liu and colleagues (Liu et al, (2010) Nature Medicine 16:191-197) have described the role of IL-7 in $T_H17$ survival and expansion. Murine anti-CD127 antibodies (including the anti-CD127 antibodies 1A11 and 6A3) and their role in the treatment of MS and other autoimmune diseases have been described in PCT application number PCT/US2009/053136.

It is desirable to isolate and develop further monoclonal antibodies that bind to and/or inhibit the biological effect of human CD127. Such antibodies may be therapeutically useful in the treatment of MS and other inflammatory and autoimmune diseases and disorders, particularly those in which pathogenic $T_H17$ cells have been implicated.

SUMMARY OF THE INVENTION

The invention provides antigen binding proteins which specifically bind to CD127. The antigen binding proteins can be used in therapeutic methods, in particular, in the treatment or prevention of diseases in which pathogenic $T_H17$ cells are implicated. The antigen binding proteins may bind to CD127 and inhibit, e.g. neutralize, the biological function of CD127.

In a first aspect, the invention provides antigen binding proteins, such as antibodies, which comprise from one to six of the following complementarity determining regions, or variants thereof:

(i) CDRH1 as set out in SEQ ID NO:2
(ii) CDRH2 as set out in SEQ ID NO:3
(iii) CDRH3 as set out in SEQ ID NO:4 or in any of SEQ ID NO:132-SEQ ID NO:137,
(iv) CDRL1 as set out in SEQ ID NO:5
(v) CDRL2 as set out in SEQ ID NO:6
(vi) CDRL3 as set out in SEQ ID NO:7.

In another aspect, the invention provides antigen binding proteins, such as antibodies, which comprise from one to six of the following complementarity determining regions, or variants thereof:

(i) CDRH1 as set out in SEQ ID NO:39
(ii) CDRH2 as set out in SEQ ID NO:40
(iii) CDRH3 as set out in SEQ ID NO:41
(iv) CDRL1 as set out in SEQ ID NO:42
(v) CDRL2 as set out in SEQ ID NO:43
(vi) CDRL3 as set out in SEQ ID NO:44.

In an embodiment the antigen binding protein is an antibody, optionally a chimeric, humanized or human antibody. The antibody may comprise the one or more CDR (of SEQ ID NO:2-7 or 39-44 from a donor antibody) in an acceptor antibody framework. The acceptor antibody framework may be a human antibody.

In an aspect, the invention provides a humanised antibody which comprises a heavy chain variable region comprising one or more of the following complementarity determining regions:

(i) CDRH1 as set out in SEQ ID NO:2
(ii) CDRH2 as set out in SEQ ID NO:3
(iii) CDRH3 as set out in SEQ ID NO:4 or in any of SEQ ID NO:132-SEQ ID NO:137, wherein the antibody further comprises at least one of: a lysine residue at position 66, a phenylalanine, methionine, isoleucine, leucine or valine residue at position 69, and a valine, arginine, alanine or leucine residue at position 71 of the heavy chain variable region (numbering according to Kabat).

In an embodiment, the humanised antibody comprises a leucine at position 69. In an embodiment, the humanised antibody comprises a valine at position 71. In an embodiment, the humanised antibody comprises a leucine at position 69 and a valine at position 71. In an embodiment, the humanised antibody comprises a lysine at position 66, a leucine at position 69 and a valine at position 71. With the exception of the abovementioned point mutations, the heavy chain variable region may have the framework sequence of a human germline variable region. For instance, in an embodiment, the heavy chain variable region is derived from the IGHV1_2 human framework (SEQ ID NO:116).

In another aspect, therefore, the invention provides an antibody comprising one or more of the following complementarity determining regions:

(i) CDRH1 as set out in SEQ ID NO:2
(ii) CDRH2 as set out in SEQ ID NO:3
(iii) CDRH3 as set out in SEQ ID NO:4 or in any of SEQ ID NO:132-SEQ ID NO:137, in a $V_H$ framework, wherein $V_H$ framework is derived from a human germline $V_H$ framework and comprises at least one of: a lysine residue at position 66, a phenylalanine, methionine, isoleucine, leucine or valine residue at position 69, and a valine, arginine, alanine or leucine residue at position 71 of the heavy chain variable region (numbering according to Kabat). In an embodiment, the human $V_H$ framework is the IGHV1_2 human framework (SEQ ID NO:116).

The antibody of the invention may comprise a heavy chain variable region comprising CDRH1 (SEQ ID NO:2) and CDRH3 (SEQ ID NO:4); CDRH2 (SEQ ID NO:3) and CDRH3 (SEQ ID NO:4); CDRH1 (SEQ ID NO:2) and CDRH2 (SEQ ID NO:3); or CDRH1 (SEQ ID NO:2), CDRH2 (SEQ ID NO:3) and CDRH3 (SEQ ID NO:4). The antibody may comprise a heavy chain variable region of any of SEQ ID NOs:10-17 (1A11.H0 $V_H$ to 1A11.H7 $V_H$). In an embodiment, the humanised antibody comprises a heavy chain variable region of SEQ ID NO:13 (1A11.H3 $V_H$). In any of these embodiments, CDRH3 of SEQ ID NO:4 may be substituted with CDRH3 as set out in any of SEQ ID NO:132-SEQ ID NO:137. Alternatively, the heavy chain variable region of SEQ ID NO:13 may comprises one or more substitutions selected from N98D, N98E, F100bE, F100bH, F100bI and F100bV (Kabat). In another embodiment, the heavy chain variable domain has an amino acid sequence of SEQ ID NOs:121, 123, 125, 127, 129, or 131. In an embodiment, the heavy chain variable region is paired with a light chain variable region of SEQ ID NO:16.

The invention also provides an antibody which comprises a light chain variable region comprising one or more of the following complementarity determining regions:
 (i) CDRL1 as set out in SEQ ID NO:5
 (ii) CDRL2 as set out in SEQ ID NO:6
 (iii) CDRL3 as set out in SEQ ID NO:7
wherein the antibody further comprises at least one of: a lysine residue at position 45, a proline residue at position 46, a tryptophan residue at position 47, a valine residue at position 58, a valine residue at position 60, a serine residue at position 70, and a tyrosine or phenylalanine residue at position 71 of the variable region light chain (numbering according to Kabat).

In an embodiment, the antibody comprises a proline residue at position 46. In an embodiment, the antibody comprises a tyrosine residue at position 71. In an embodiment, the antibody comprises a proline residue at position 46 and a tyrosine residue at position 71.

The antibody may comprise a light chain variable region comprising CDRL1 (SEQ ID NO:5) and CDRL3 (SEQ ID NO:7); CDRL2 (SEQ ID NO:6) and CDRL3 (SEQ ID NO:7); CDRL1 (SEQ ID NO:5) and CDRL2 (SEQ ID NO:6); or CDRL1 (SEQ ID NO:5), CDRL2 (SEQ ID NO:6) and CDRL3 (SEQ ID NO:7). The antibody may comprise a light chain variable region of any of SEQ ID NOs:18-27 (1A11.L0 Vκ to 1A11.L9 Vκ). In an embodiment, the antibody comprises a light chain variable region of SEQ ID NO:22 (1A11.L4 Vκ).

In another aspect, the invention provides a antibody comprising: a heavy chain variable region comprising one, two or three of the following complementarity determining regions:
 (i) CDRH1 as set out in SEQ ID NO:2
 (ii) CDRH2 as set out in SEQ ID NO:3
 (iii) CDRH3 as set out in SEQ ID NO:4 or in any of SEQ ID NO:132-SEQ ID NO:137,
wherein the antibody further comprises at least one of: a lysine residue at position 66, a phenylalanine, methionine, isoleucine, leucine or valine residue at position 69, and a valine, arginine, alanine or leucine at position 71 of the heavy chain variable region (numbering according to Kabat); and a light chain variable region comprising one, two or three of the following complementarity determining regions:
 (i) CDRL1 as set out in SEQ ID NO:5
 (ii) CDRL2 as set out in SEQ ID NO:6
 (iii) CDRL3 as set out in SEQ ID NO:7
wherein the antibody further comprises at least one of: a lysine residue at position 45, a proline residue at position 46, a tryptophan residue at position 47, a valine residue at position 58, a valine residue at position 60, a serine residue at position 70, and a tyrosine or phenylalanine residue at position 71 of the variable region light chain (numbering according to Kabat).

The antibody may comprise any combination of CDRH1, CDRH2, CDRH3, CDRL1, CDRL2 and CDRL3, including from one heavy chain CDR and one light chain CDR, to all six of said CDRs (i.e. all 3 heavy chain and 3 light chain CDRs). In an embodiment, the antibody comprises all six of CDRH1, CDRH2, CDRH3, CDRL1, CDRL2 and CDRL3.

In one embodiment, the antibody comprises: a heavy chain variable region comprising the following complementarity determining regions:
 (i) CDRH1 as set out in SEQ ID NO:2
 (ii) CDRH2 as set out in SEQ ID NO:3
 (iii) CDRH3 as set out in SEQ ID NO:4 or in any of SEQ ID NO:133-SEQ ID NO:138,
and a light chain variable region comprising the following complementarity determining regions:
 (iv) CDRL1 as set out in SEQ ID NO:5
 (v) CDRL2 as set out in SEQ ID NO:6
 (vi) CDRL3 as set out in SEQ ID NO:7
wherein the antibody further comprises a leucine residue at position 69 of the heavy chain variable region, and a proline residue at position 46 of the light chain variable region.

In an embodiment, the antigen binding protein comprises a heavy chain variable region comprising the amino acid sequence of SEQ ID NO:13 (1A11.H3 $V_H$) or an amino acid sequence having 75% or greater, 80% or greater, 85% or greater, 90% or greater, 95% or greater, 98% or greater, 99% or greater identity to the amino acid sequence of SEQ ID NO:13, or a heavy chain variable region comprising the amino acid sequence set out in any of SEQ ID NO:121, 123, 125, 127, 129 or 131, and a light chain variable region comprising the amino acid sequence of SEQ ID NO:22 (1A11.L4 Vκ) or an amino acid sequence having 75% or greater, 80% or greater, 85% or greater, 90% or greater, 95% or greater, 98% or greater, 99% or greater identity to the amino acid sequence of SEQ ID NO:22.

In an embodiment, the antigen binding protein comprises a heavy chain comprising the amino acid sequence of SEQ ID NO:114 or an amino acid sequence having 75% or greater, 80% or greater, 85% or greater, 90% or greater, 95% or greater, 98% or greater, 99% or greater identity to the amino acid sequence of SEQ ID NO:114 or SEQ ID NO:118. In particular embodiments, the heavy chain comprises one or more substitutions selected from N98D, N98E, F100bE, F100bH, F100bI and F100bV (Kabat). In an embodiment, the antigen binding protein comprises a light chain comprising the amino acid sequence of SEQ ID NO:115 or an amino acid sequence having 75% or greater, 80% or greater, 85% or greater, 90% or greater, 95% or greater, 98% or greater, 99% or greater identity to the amino acid sequence of SEQ ID NO:115. In an embodiment, the antigen binding protein comprises a heavy chain comprising the amino acid sequence of SEQ ID NO:114 or 118, or an amino acid sequence having 75% or greater, 80% or greater, 85% or greater, 90% or greater, 95% or greater, 98% or greater, 99% or greater identity to the amino acid sequence of SEQ ID NO:114 or 118 and a light chain comprising the amino acid sequence of SEQ ID NO:115 or an amino acid sequence having 75% or greater, 80% or greater, 85% or greater, 90% or greater, 95% or greater, 98% or greater, 99% or greater identity to the amino acid sequence of SEQ ID NO:115. A particular embodiment comprises an antigen binding protein having a heavy chain amino acid sequence of SEQ ID NO:118 and a light chain amino acid sequence of SEQ ID NO:115.

In another aspect, the invention provides an antigen binding protein which comprises one or more of:
- (i) CDRH1 as set out in SEQ ID NO:2 or a variant CDR thereof,
- (ii) CDRH2 as set out in SEQ ID NO:3 or a variant CDR thereof,
- (iii) CDRH3 as set out in SEQ ID NO:4 or a variant CDR thereof, or a CDRH3 as set out in any of SEQ ID NO:132-SEQ ID NO:137,
- (iv) CDRL1 as set out in SEQ ID NO:5 or a variant CDR thereof,
- (v) CDRL2 as set out in SEQ ID NO:6 or a variant CDR thereof,
- (vi) CDRL3 as set out in SEQ ID NO:7 or a variant CDR thereof, further comprising a heavy chain framework having at least one of the following residues:
- (a) Val, Ile or Gly at position 2
- (b) Leu or Val at position 4
- (c) Leu, Ile, Met or Val at position 20
- (d) Cys at position 22
- (e) Thr, Ala, Val, Gly or Ser at position 24
- (f) Gly at position 26
- (g) Trp or Tyr at position 47
- (h) Ile, Met, Val or Leu at position 48
- (i) Ile, Leu, Phe, Met or Val at position 69
- (j) Arg, Val, Ala or Leu at position 71
- (k) Ala, Leu, Val, Tyr or Phe at position 78
- (l) Leu or Met at position 80
- (m) Tyr or Phe at position 90
- (n) Cys at position 92
- (o) Arg, Lys, Gly, Ser, His or Asn at position 94, and/or a light chain framework having at least one of the following residues:
- (p) Ile at position 2
- (q) Leu at position 4
- (r) Cys at position 23
- (s) Trp at position 35
- (t) Tyr at position 36
- (u) Tyr or Phe at position 71
- (v) Cys at position 88
- (w) Phe at position 98, wherein the antigen binding protein is capable of binding to CD127.

The antigen binding protein may comprise any combination of CDRH1, CDRH2, CDRH3, CDRL1, CDRL2 and CDRL3, including from one CDR to six of said CDRs (SEQ ID NOs:2-7). In one embodiment, the antigen binding protein comprises all six of said CDRs (SEQ ID NOs:2-7).

In an embodiment, the antigen binding protein comprises both of the heavy chain framework and the light chain framework regions as described above.

In an embodiment, the antigen binding protein is an antibody, optionally a humanised or human antibody, or an antigen binding fragment thereof.

The one or more variant CDRs of this aspect of the invention may comprise:
- (a) a variant of CDRH1 (SEQ ID NO:2), wherein:
  - i. the tyrosine residue at position 32 is substituted for isoleucine, histidine, phenylalanine, threonine, asparagine, cysteine, glutamic acid or aspartic acid;
  - ii. the threonine residue at position 33 is substituted for a tyrosine, alanine, tryptophan, glycine, leucine or valine;
  - iii. the methionine residue at position 34 is substituted for isoleucine, valine or tryptophan; and/or
  - iv. the asparagine residue at position 35 is substituted for histidine, glutamic acid, glutamine, serine, tyrosine or threonine;
- (b) a variant of CDRH2 (SEQ ID NO:3) wherein:
  - i. the leucine residue at position 50 is substituted for arginine, glutamic acid, tryptophan, tyrosine, glycine, glutamine, valine, asparagine, lysine or alanine;
  - ii. the isoleucine residue at position 51 is substituted for leucine, valine, threonine, serine or asparagine;
  - iii. the asparagine residue at position 52 is substituted for asparagine, leucine, serine or tyrosine;
  - iv. the tyrosine residue at position 53 is substituted for alanine, glycine, serine, lysine, threonine or asparagine;
  - v. the asparagine at position 54 is substituted for serine, threonine, lysine, asparagine or glycine;
  - vi. the valine at position 56 is substituted for tyrosine, arginine, glutamic acid, aspartic acid, glycine, serine or alanine; and/or
  - vii. the serine at position 58 is substituted for lysine, asparagine, threonine, arginine, glycine, phenylalanine or tyrosine;
- (c) a variant of CDRH3 (SEQ ID NO:4) wherein the valine at position 102 is substituted for tyrosine, histidine, isoleucine, serine, aspartic acid or glycine;
- (d) a variant of CDRL1 (SEQ ID NO:5) wherein:
  - i. the serine at position 29 is substituted for a valine; and/or
  - ii. the methionine at position 33 is substituted for a leucine; and/or
- (e) a variant of CDRL3 (SEQ ID NO:7) comprising one or more of the following substitutions:
  - i. the glutamine at position 89 is substituted for leucine;
  - ii. the glutamic acid at position 90 is substituted for glutamine;
  - iii. the tryptophan at position 91 is substituted for tyrosine; and/or
  - iv. the tyrosine at position 93 is substituted for serine or arginine.

The antigen binding protein may comprise a heavy chain variable region of any of SEQ ID NOs:10-17 (1A11.H0 V$_H$ to 1A11.H7 V$_H$) or a heavy chain variable region of any of SEQ ID NO:121, 123, 125, 127, 129 or 131. In an embodiment, the antigen binding protein comprises a heavy chain variable region of SEQ ID NO:13 (1A11.H3 V$_H$). The antigen binding protein may comprise a light chain variable region of any of SEQ ID NOs:18-27 (1A11.L0 Vκ to 1A11.L9 Vκ). In an embodiment, the antigen binding protein comprises a light chain variable region of SEQ ID NO:22 (1A11.L4 Vκ).

In a particular embodiment, the antigen binding protein comprises a heavy chain variable region of SEQ ID NO:13 (1A11.H3 V$_H$), and a light chain variable region of SEQ ID NO:22 (1A11.L4 Vκ). In another embodiment, the antigen binding protein comprises a heavy chain of SEQ ID NO: 114 or SEQ ID NO:118, particularly SEQ ID NO:118, and a light chain of SEQ ID NO:115. The heavy chain may further comprise any of the following substitutions: N98D, N98E, F100bE, F100bH, F100bI and F100bV (Kabat).

In another embodiment, the antigen binding protein comprises one or more point mutations within CDRH3, and wherein the antigen binding protein has a higher binding affinity for IL-7R than the antigen binding protein lacking said mutation. For example, in an embodiment, the antigen binding protein comprises a CDRH3 as set out in SEQ ID NOs:132-137. In an embodiment, the antigen binding protein comprises a heavy chain variable region as set out in SEQ ID NOs:121, 123, 125, 127, 129 or 131.

In another aspect, the invention provides an antigen binding protein comprising a heavy chain variable domain as set out in:
(a) SEQ ID NO:11
(b) SEQ ID NO:12
(c) SEQ ID NO:13
(d) SEQ ID NO:14
(e) SEQ ID NO:15
(f) SEQ ID NO:16
(g) SEQ ID NO:17
(h) SEQ ID NO:121
(i) SEQ ID NO:123
(j) SEQ ID NO:125
(k) SEQ ID NO:127
(l) SEQ ID NO:129
(m) SEQ ID NO:131,
or a heavy chain variable domain having 70% or more identity to one of SEQ ID NOs:11 to 17, wherein the antigen binding protein is capable of binding to CD127.

In an embodiment, the heavy chain variable domain has 75% or greater, 80% or greater, 85% or greater, 90% or greater, 95% or greater, 98% or greater, 99% or greater identity to one of SEQ ID NOs:11 to 17.

In an embodiment, the antigen binding protein comprises a heavy chain variable domain as set out in SEQ ID NO:13, or a heavy chain variable domain having 70% or greater, 75% or greater, 80% or greater, 85% or greater, 90% or greater, 95% or greater, 98% or greater, 99% or greater identity to SEQ ID NO:13.

In an embodiment, the antigen binding protein has a heavy chain having 70% or greater, 75% or greater, 80% or greater, 85% or greater, 90% or greater, 95% or greater, 98% or greater, 99% or greater identity to SEQ ID NO:115 or SEQ ID NO:118.

In an embodiment, the heavy chain, or heavy chain variable domain, is a variant of one of SEQ ID NOs: 11 to 17, 121, 123, 125, 127, 129, 131, and wherein the extent of variation consists of one or more of:
i. Val, Ile or Gly at position 2
ii. Leu or Val at position 4
iii. Leu, Ile, Met or Val at position 20
iv. Thr, Ala, Val, Gly or Ser at position 24
v. Trp or Tyr at position 47
vi. Ile, Met, Val or Leu at position 48
vii. Ile, Leu, Phe, Met or Val at position 69
viii. Arg, Val, Ala or Leu at position 71
ix. Ala, Leu, Val, Tyr or Phe at position 78
x. Leu or Met at position 80
xi. Tyr or Phe at position 90; and
xii. Arg, Lys, Gly, Ser, His or Asn at position 94.

In another aspect, the invention provides an antigen binding protein comprising a light chain variable domain as set out in:
(a) SEQ ID NO:19
(b) SEQ ID NO:20
(c) SEQ ID NO:21
(d) SEQ ID NO:22
(e) SEQ ID NO:23
(f) SEQ ID NO:24
(g) SEQ ID NO:25
(h) SEQ ID NO:26
(i) SEQ ID NO:27
or a light chain variable domain having 70% or more identity to one of SEQ ID NOs:19 to 27, wherein the antigen binding protein is capable of binding to CD127.

In an embodiment, the antigen binding protein comprises a light chain variable domain as set out in SEQ ID NO:22, or a light chain variable domain having 70% or more identity to SEQ ID NO:22.

In an embodiment, the light chain variable domain has 75% or greater, 80% or greater, 85% or greater, 90% or greater, 95% or greater, 98% or greater, 99% or greater identity to one of SEQ ID NOs:19 to 27.

In an embodiment, the antigen binding protein has a light chain having 70% or greater, 75% or greater, 80% or greater, 85% or greater, 90% or greater, 95% or greater, 98% or greater, 99% or greater identity to SEQ ID NO: 115.

The invention contemplates any pairing of the described heavy and light variable domains. In an embodiment, therefore, the invention also provides an antigen binding protein comprising any one of the following heavy and light chain variable domain combinations: a heavy chain variable domain of SEQ ID NO:11 (or a sequence having 75% or greater, 80% or greater, 85% or greater, 90% or greater, 95% or greater, 98% or greater, 99% or greater identity thereto), with a light chain variable domain of any one of SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27 (or a sequence having 75% or greater, 80% or greater, 85% or greater, 90% or greater, 95% or greater, 98% or greater, or 99% or greater identity to any of SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27); a heavy chain variable domain of SEQ ID NO:12 (or a sequence having 75% or greater, 80% or greater, 85% or greater, 90% or greater, 95% or greater, 98% or greater, 99% or greater identity thereto), with a light chain variable domain of any one of SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27 (or a sequence having 75% or greater, 80% or greater, 85% or greater, 90% or greater, 95% or greater, 98% or greater, or 99% or greater identity to any of SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27); a heavy chain variable domain of SEQ ID NO:13 (or a sequence having 75% or greater, 80% or greater, 85% or greater, 90% or greater, 95% or greater, 98% or greater, 99% or greater identity thereto), with a light chain variable domain of any one of SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27 (or a sequence having 75% or greater, 80% or greater, 85% or greater, 90% or greater, 95% or greater, 98% or greater, or 99% or greater identity to any of SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27); a heavy chain variable domain of SEQ ID NO:14 (or a sequence having 75% or greater, 80% or greater, 85% or greater, 90% or greater, 95% or greater, 98% or greater, 99% or greater identity thereto), with a light chain variable domain of any one of SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27 (or a sequence having 75% or greater, 80% or greater, 85% or greater, 90% or greater, 95% or greater, 98% or greater, or 99% or greater identity to any of SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27); a heavy chain variable domain of SEQ ID NO:15 (or a sequence having 75% or greater, 80% or greater, 85% or greater, 90% or greater, 95% or greater, 98% or greater, 99% or greater identity thereto), with a light chain variable domain of any one of SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27 (or a sequence having 75% or greater, 80% or greater, 85% or greater, 90% or greater, 95% or greater, 98% or greater, or 99% or greater identity to any of SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27); a heavy chain variable domain of SEQ ID NO:16 (or a sequence having 75% or greater, 80% or greater, 85% or greater, 90% or greater, 95% or greater, 98% or greater, 99% or greater identity thereto), with a light chain variable domain of any one of SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27 (or a sequence having 75% or greater, 80% or greater, 85% or greater, 90% or greater, 95% or greater, 98% or greater, or 99% or greater identity to any of SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27); a heavy chain variable domain of SEQ ID NO:17 (or a sequence having 75% or greater, 80% or greater, 85% or greater, 90% or greater, 95% or greater, 98% or greater, 99% or greater identity thereto), with a light chain variable domain of any one of SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27 (or a sequence having 75% or greater, 80% or greater, 85% or greater, 90% or greater, 95% or greater, 98% or greater, or 99% or greater identity to any of SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27); a heavy chain variable domain of SEQ ID NO:121 (or a sequence having 75% or greater, 80% or greater, 85% or greater, 90% or greater, 95% or greater, 98% or greater, 99% or greater identity thereto), with a light chain variable domain of any one of SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27 (or a sequence having 75% or greater, 80% or greater, 85% or greater, 90% or greater, 95% or greater, 98% or greater, or 99% or greater identity to any of SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27); a heavy chain variable domain of SEQ ID NO:123 (or a sequence having 75% or greater, 80% or greater, 85% or greater, 90% or greater, 95% or greater, 98% or greater, 99% or greater identity thereto), with a light chain variable domain of any one of SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27 (or a sequence having 75% or greater, 80% or greater, 85% or greater, 90% or greater, 95% or greater, 98% or greater, or 99% or greater identity to any of SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27); a heavy chain variable domain of SEQ ID NO:125 (or a sequence having 75% or greater, 80% or greater, 85% or greater, 90% or greater, 95% or greater, 98% or greater, 99% or greater identity thereto), with a light chain variable domain of any one of SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27 (or a sequence having 75% or greater, 80% or greater, 85% or greater, 90% or greater, 95% or greater, 98% or greater, or 99% or greater identity to any of SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27); a heavy chain variable domain of SEQ ID NO:127 (or a sequence having 75% or greater, 80% or greater, 85% or greater, 90% or greater, 95% or greater, 98% or greater, 99% or greater identity thereto), with a light chain variable domain of any one of SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27 (or a sequence having 75% or greater, 80% or greater, 85% or greater, 90% or greater, 95% or greater, 98% or greater, or 99% or greater identity to any of SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27); a heavy chain variable domain of SEQ ID NO:129 (or a sequence having 75% or greater, 80% or greater, 85% or greater, 90% or greater, 95% or greater, 98% or greater, 99% or greater identity thereto), with a light chain variable domain of any one of SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27 (or a sequence having 75% or greater, 80% or greater, 85% or greater, 90% or greater, 95% or greater, 98% or greater, or 99% or greater identity to any of SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27); or, a heavy chain variable domain of SEQ ID NO:131 (or a sequence having 75% or greater, 80% or greater, 85% or greater, 90% or greater, 95% or greater, 98% or greater, 99% or greater identity thereto), with a light chain variable domain of any one of SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27 (or a sequence having 75% or greater, 80% or greater, 85% or greater, 90% or greater, 95% or greater, 98% or greater, or 99% or greater identity to any of SEQ ID NO:19, SEQ ID NO:20, SEQ ID NO:21, SEQ ID NO:22, SEQ ID NO:23, SEQ ID NO:24, SEQ ID NO:25, SEQ ID NO:26, or SEQ ID NO:27).

In one embodiment, the antigen binding protein comprises a heavy chain variable domain comprising an amino acid sequence having 75% or greater, 80% or greater, 85% or greater, 90% or greater, 95% or greater, 98% or greater, 99% or greater identity to the sequence set out in SEQ ID NO:13 and a light chain variable domain comprising an amino acid sequence having 75% or greater, 80% or greater, 85% or greater, 90% or greater, 95% or greater, 98% or greater, 99% or greater identity to the sequence set out in SEQ ID NO:22.

In one embodiment, the antigen binding protein comprises a heavy chain variable domain as set out in SEQ ID NO:13 and a light chain variable domain as set out in SEQ ID NO:22.

In another aspect, the invention provides an antigen binding protein comprising one or more of the following complementarity determining regions:
  (i) CDRH1 as set out in SEQ ID NO:2 or a variant CDR thereof
  (ii) CDRH2 as set out in SEQ ID NO:3 or a variant CDR thereof
  (iii) CDRH3 as set out in SEQ ID NO:4 or a variant CDR thereof, or a CDRH3 as set out in any of SEQ ID NO:132-SEQ ID NO:137,
  (iv) CDRL1 as set out in SEQ ID NO:5 or a variant CDR thereof
  (v) CDRL2 as set out in SEQ ID NO:6 or a variant CDR thereof
  (vi) CDRL3 as set out in SEQ ID NO:7 or a variant CDR thereof wherein at least one of said CDRs is a variant CDR, and wherein said antigen binding protein is capable of binding to CD127.

In an embodiment, the antigen binding protein comprises at least CDRL2 as set out in SEQ ID NO:6, or a variant thereof. In an embodiment, the antigen binding protein comprises at least CDRH3 as set out in SEQ ID NO:4, or a variant CDR thereof. The variant CDR of this aspect of the invention may comprise:

(f) a variant of CDRH1 (SEQ ID NO:2), wherein:
  i. the tyrosine residue at position 32 is substituted for isoleucine, histidine, phenylalanine, threonine, asparagine, cysteine, glutamic acid or aspartic acid;
  ii. the threonine residue at position 33 is substituted for a tyrosine, alanine, tryptophan, glycine, leucine or valine,
  iii. the methionine residue at position 34 is substituted for isoleucine, valine or tryptophan; and/or
  iv. the asparagine residue at position 35 is substituted for histidine, glutamic acid, glutamine, serine, tyrosine or threonine;
(g) a variant of CDRH2 (SEQ ID NO:3) wherein:
  i. the leucine residue at position 50 is substituted for arginine, glutamic acid, tryptophan, tyrosine, glycine, glutamine, valine, asparagine, lysine or alanine;
  ii. the isoleucine residue at position 51 is substituted for leucine, valine, threonine, serine or asparagine;
  iii. the asparagine residue at position 52 is substituted for asparagine, leucine, serine or tyrosine;
  iv. the tyrosine residue at position 53 is substituted for alanine, glycine, serine, lysine, threonine or asparagine;
  v. the asparagine at position 54 is substituted for serine, threonine, lysine, asparagine or glycine;
  vi. the valine at position 56 is substituted for tyrosine, arginine, glutamic acid, aspartic acid, glycine, serine or alanine; and/or
  vii. the serine at position 58 is substituted for lysine, asparagine, threonine, arginine, glycine, phenylalanine or tyrosine;
(h) a variant of CDRH3 (SEQ ID NO:4) wherein the valine at position 102 is substituted for tyrosine, histidine, isoleucine, serine, aspartic acid or glycine;
(i) a variant of CDRL1 (SEQ ID NO:5) wherein:
  i. the serine at position 29 is substituted for a valine; and/or
  ii. the methionine at position 33 is substituted for a leucine; and/or
(j) a variant of CDRL3 (SEQ ID NO:7) comprising one or more of the following substitutions:
  i. the glutamine at position 89 is substituted for leucine;
  ii. the glutamic acid at position 90 is substituted for glutamine;
  iii. the tryptophan at position 91 is substituted for tyrosine; and/or
  iv. the tyrosine at position 93 is substituted for serine or arginine.

In another aspect, the invention provides an antigen binding protein comprising: a heavy chain variable domain comprising:
  (i) CDRH1 as set out in SEQ ID NO:2 or a variant CDR thereof
  (ii) CDRH2 as set out in SEQ ID NO:3 or a variant CDR thereof
  (iii) CDRH3 as set out in SEQ ID NO:4 or a variant CDR thereof, or a CDRH3 as set out in any of SEQ ID NO:132-SEQ ID NO:137 in a heavy chain variable domain framework, which comprises at least one of:
  (a) Val, Ile or Gly at position 2
  (b) Leu or Val at position 4
  (c) Leu, Ile, Met or Val at position 20
  (d) Cys at position 22
  (e) Thr, Ala, Val, Gly or Ser at position 24
  (f) Gly at position 26
  (g) Trp or Tyr at position 47
  (h) Ile, Met, Val or Leu at position 48
  (i) Ile, Leu, Phe, Met or Val at position 69
  (j) Arg, Val, Ala or Leu at position 71
  (k) Ala, Leu, Val, Tyr or Phe at position 78
  (l) Leu or Met at position 80
  (m) Tyr or Phe at position 90
  (n) Cys at position 92
  (o) Arg, Lys, Gly, Ser, His or Asn at position 94;
and a light chain variable domain comprising:
  (iv) CDRL1 as set out in SEQ ID NO:5 or a variant CDR thereof
  (v) CDRL2 as set out in SEQ ID NO:6 or a variant CDR thereof
  (vi) CDRL3 as set out in SEQ ID NO:7 or a variant CDR thereof
in a light chain variable domain framework, which comprises at least one of:
  (a) Ile at position 2
  (b) Leu at position 4
  (c) Cys at position 23
  (d) Trp at position 35
  (e) Tyr at position 36
  (f) Tyr or Phe at position 71
  (g) Cys at position 88
  (h) Phe at position 98;
wherein the antigen binding protein is capable of binding to CD127.

The variant CDR of this aspect of the invention may comprise:
(a) a variant of CDRH1 (SEQ ID NO:2), wherein:
  i. the tyrosine residue at position 32 is substituted for isoleucine, histidine, phenylalanine, threonine, asparagine, cysteine, glutamic acid or aspartic acid;
  ii. the threonine residue at position 33 is substituted for a tyrosine, alanine, tryptophan, glycine, leucine or valine,
  iii. the methionine residue at position 34 is substituted for isoleucine, valine or tryptophan; and/or
  iv. the asparagine residue at position 35 is substituted for histidine, glutamic acid, glutamine, serine, tyrosine or threonine;
(b) a variant of CDRH2 (SEQ ID NO:3) wherein:
  i. the leucine residue at position 50 is substituted for arginine, glutamic acid, tryptophan, tyrosine, glycine, glutamine, valine, asparagine, lysine or alanine;
  ii. the isoleucine residue at position 51 is substituted for leucine, valine, threonine, serine or asparagine;
  iii. the asparagine residue at position 52 is substituted for asparagine, leucine, serine or tyrosine;
  iv. the tyrosine residue at position 53 is substituted for alanine, glycine, serine, lysine, threonine or asparagine;
  v. the asparagine at position 54 is substituted for serine, threonine, lysine, asparagine or glycine;
  vi. the valine at position 56 is substituted for tyrosine, arginine, glutamic acid, aspartic acid, glycine, serine or alanine; and/or vii. the serine at position 58 is substituted for lysine, asparagine, threonine, arginine, glycine, phenylalanine or tyrosine;
(c) a variant of CDRH3 (SEQ ID NO:4) wherein the valine at position 102 is substituted for tyrosine, histidine, isoleucine, serine, aspartic acid or glycine;
(d) a variant of CDRL1 (SEQ ID NO:5) wherein:
  i. the serine at position 29 is substituted for a valine; and/or
  ii. the methionine at position 33 is substituted for a leucine; and/or
(e) a variant of CDRL3 (SEQ ID NO:7) comprising one or more of the following substitutions:
  i. the glutamine at position 89 is substituted for leucine;
  ii. the glutamic acid at position 90 is substituted for glutamine;
  iii. the tryptophan at position 91 is substituted for tyrosine; and/or
  iv. the tyrosine at position 93 is substituted for serine or arginine.

In an embodiment, the antigen binding protein is an antibody, optionally a humanised or human antibody, or an antigen binding fragment thereof.

In another aspect, the invention provides an antibody which comprises a heavy chain variable region comprising one, two or three of the following complementarity determining regions:
  (i) CDRH1 as set out in SEQ ID NO:39
  (ii) CDRH2 as set out in SEQ ID NO:40
  (iii) CDRH3 as set out in SEQ ID NO:41
wherein the antibody further comprises at least one of: a valine at position 24, a tyrosine at position 27, a serine at position 28, an isoleucine at position 29, a threonine at position 30, a methionine at position 48, a glycine at position 49, an isoleucine at position 67, an a serine at position 68, an arginine at position 71, a threonine at position 73 and a phenylalanine at position 78 of the heavy chain variable region (numbering according to Kabat).

In an embodiment, the antibody comprises at least one, two, three, four or all five of a tyrosine at position 27, a threonine at position 30, a methionine at position 48, an isoleucine at position 67 and an arginine at position 71.

The antibody may comprise a heavy chain variable region comprising CDRH1 (SEQ ID NO:39) and CDRH3 (SEQ ID NO:41); CDRH2 (SEQ ID NO:40) and CDRH3 (SEQ ID NO:41); CDRH1 (SEQ ID NO:39) and CDRH2 (SEQ ID NO:40); or CDRH1 (SEQ ID NO:39), CDRH2 (SEQ ID NO:40) and CDRH3 (SEQ ID NO:41). The antibody may comprise a heavy chain variable region of any of SEQ ID NOs:48-56 (6A3IGHV4_61.H1 $V_H$ to 6A3IGHV4_61.H9) or SEQ ID NOs:58-68 (6A3IGHV3-33.H1 $V_H$ to 6A3 IGHV3-33.H11).

The invention also provides an antibody which comprises a light chain variable region comprising one, two or three of the following complementarity determining regions:
  (iv) CDRL1 as set out in SEQ ID NO:42
  (v) CDRL2 as set out in SEQ ID NO:43
  (vi) CDRL3 as set out in SEQ ID NO:44
wherein the antibody further comprises:
  (a) one or both of a glutamine residue at position 45 and a lysine residue at position 70 of the variable region light chain, or
  (b) one or more of a leucine at position 4, a tyrosine at position 31, a methionine at position 70, a threonine at position 85, a tyrosine at position 94, a glycine at position 100 and a valine at position 104 (numbering according to Kabat).

In an embodiment, the antibody comprises both a glutamine residue at position 45 and a lysine residue at position 70. In another embodiment, the antibody comprises each of a leucine at position 4, a tyrosine at position 31, a methionine at position 70, a threonine at position 85, a tyrosine at position 94, a glycine at position 100 and a valine at position 104.

The antibody may comprise a light chain variable region comprising CDRL1 (SEQ ID NO:42) and CDRL3 (SEQ ID NO:44); CDRL2 (SEQ ID NO:43) and CDRL3 (SEQ ID NO:44); or CDRL1 (SEQ ID NO:42) and CDRL2 (SEQ ID NO:43); or CDRL1 (SEQ ID NO:42), CDRL2 (SEQ ID NO:43) and CDRL3 (SEQ ID NO:44). The antibody may comprise a light chain variable region of any of SEQ ID NOs:70-72 and 138 (6A3.L1 Vκ, 6A3.L2 Vκ, 6A3.L3 Vκ and 6A3.L27 Vκ).

In another aspect, the invention provides an antibody which comprises a heavy chain variable region comprising one, two or three of the following complementarity determining regions:
  (iv) CDRH1 as set out in SEQ ID NO:39
  (v) CDRH2 as set out in SEQ ID NO:40
  (vi) CDRH3 as set out in SEQ ID NO:41
wherein the antibody further comprises at least one of: a valine at position 24, a tyrosine at position 27, a serine at position 28, an isoleucine at position 29, a threonine at position 30, a methionine at position 48, a glycine at position 49, an isoleucine at position 67, an a serine at position 68, an arginine at position 71, a threonine at position 73 and a phenylalanine at position 78 of the heavy chain variable region, and
a light chain variable region comprising one, two or three of the following complementarity determining regions:
  (i) CDRL1 as set out in SEQ ID NO:42
  (ii) CDRL2 as set out in SEQ ID NO:43
  (iii) CDRL3 as set out in SEQ ID NO:44
wherein the antibody further comprises:
  (a) one or both of a glutamine residue at position 45 and a lysine residue at position 70 of the variable region light chain; or
  (b) one or more of a leucine at position 4, a tyrosine at position 31, a methionine at position 70, a threonine at position 85, a tyrosine at position 94, a glycine at position 100 and a valine at position 104 (numbering according to Kabat).

The antibody may comprise any combination of CDRH1, CDRH2, CDRH3, CDRL1, CDRL2 and CDRL3, including from one heavy chain and one light chain CDR, to all six of said CDRs.

In one embodiment, the antibody comprises: a heavy chain variable region comprising the following complementarity determining regions:
  (i) CDRH1 as set out in SEQ ID NO:39
  (ii) CDRH2 as set out in SEQ ID NO:40
  (iii) CDRH3 as set out in SEQ ID NO:41
  (iv) CDRL1 as set out in SEQ ID NO:42
  (v) CDRL2 as set out in SEQ ID NO:43
  (vi) CDRL3 as set out in SEQ ID NO:44
wherein the antibody further comprises at least one of:
  (a) a valine at position 24, a tyrosine at position 27, a serine at position 28, an isoleucine at position 29, a threonine at position 30, a methionine at position 48, a glycine at position 49, an isoleucine at position 67, a serine at position 68, an arginine at position 71, a threonine at position 73 and a phenylalanine at position 78 of the heavy chain variable region; and/or (b)
- a. at least one of a glutamine residue at position 45 and a lysine residue at position 70 of the variable region light chain, or
- b. one or more of a leucine at position 4, a tyrosine at position 31, a methionine at position 70, a threonine at position 85, a tyrosine at position 94, a glycine at position 100 and a valine at position 104 (numbering according to Kabat).

The invention contemplates any pairing of the described heavy and light variable domains. In an embodiment, therefore, the invention also provides an antigen binding protein comprising any one of the following heavy and light chain variable domain combinations: a heavy chain variable domain of SEQ ID NO:47 (or a sequence having 75% or greater, 80% or greater, 85% or greater, 90% or greater, 95% or greater, 98% or greater, 99% or greater identity thereto), with a light chain variable domain of any one of SEQ ID NO:69, SEQ ID NO:70, SEQ ID NO:71, SEQ ID NO:72 or SEQ ID NO:138 (or a sequence having 75% or greater, 80% or greater, 85% or greater, 90% or greater, 95% or greater, 98% or greater, or 99% or greater identity to any of SEQ ID NO:69, SEQ ID NO:70, SEQ ID NO:71, SEQ ID NO:72 or SEQ ID NO:138);

a heavy chain variable domain of SEQ ID NO:48 (or a sequence having 75% or greater, 80% or greater, 85% or greater, 90% or greater, 95% or greater, 98% or greater, 99% or greater identity thereto), with a light chain variable domain of any one of SEQ ID NO:69, SEQ ID NO:70, SEQ ID NO:71, SEQ ID NO:72 or SEQ ID NO:138 (or a sequence having 75% or greater, 80% or greater, 85% or greater, 90% or greater, 95% or greater, 98% or greater, or 99% or greater identity to any of SEQ ID NO:69, SEQ ID NO:70, SEQ ID NO:71, SEQ ID NO:72 or SEQ ID NO:138);

a heavy chain variable domain of SEQ ID NO:49 (or a sequence having 75% or greater, 80% or greater, 85% or greater, 90% or greater, 95% or greater, 98% or greater, 99% or greater identity thereto), with a light chain variable domain of any one of SEQ ID NO:70, SEQ ID NO:71, SEQ ID NO:72, SEQ ID NO:73 or SEQ ID NO:138 (or a sequence having 75% or greater, 80% or greater, 85% or greater, 90% or greater, 95% or greater, 98% or greater, or 99% or greater identity to any of SEQ ID NO:70, SEQ ID NO:71, SEQ ID NO:72, SEQ ID NO:73 or SEQ ID NO:138);

a heavy chain variable domain of SEQ ID NO:50 (or a sequence having 75% or greater, 80% or greater, 85% or greater, 90% or greater, 95% or greater, 98% or greater, 99% or greater identity thereto), with a light chain variable domain of any one of SEQ ID NO:69, SEQ ID NO:70, SEQ ID NO:71, SEQ ID NO:72 or SEQ ID NO:138 (or a sequence having 75% or greater, 80% or greater, 85% or greater, 90% or greater, 95% or greater, 98% or greater, or 99% or greater identity to any of SEQ ID NO:69, SEQ ID NO:70, SEQ ID NO:71, SEQ ID NO:72 or SEQ ID NO:138);

a heavy chain variable domain of SEQ ID NO:51 (or a sequence having 75% or greater, 80% or greater, 85% or greater, 90% or greater, 95% or greater, 98% or greater, 99% or greater identity thereto), with a light chain variable domain of any one of SEQ ID NO:69, SEQ ID NO:70, SEQ ID NO:71, SEQ ID NO:72 or SEQ ID NO:138 (or a sequence having 75% or greater, 80% or greater, 85% or greater, 90% or greater, 95% or greater, 98% or greater, or 99% or greater identity to any of SEQ ID NO:69, SEQ ID NO:70, SEQ ID NO:71, SEQ ID NO:72 or SEQ ID NO:138);

a heavy chain variable domain of SEQ ID NO:52 (or a sequence having 75% or greater, 80% or greater, 85% or greater, 90% or greater, 95% or greater, 98% or greater, 99% or greater identity thereto), with a light chain variable domain of any one of SEQ ID NO:69, SEQ ID NO:70, SEQ ID NO:71, SEQ ID NO:72 or SEQ ID NO:138 (or a sequence having 75% or greater, 80% or greater, 85% or greater, 90% or greater, 95% or greater, 98% or greater, or 99% or greater identity to any of SEQ ID NO:69, SEQ ID NO:70, SEQ ID NO:71, SEQ ID NO:72 or SEQ ID NO:138);

a heavy chain variable domain of SEQ ID NO:53 (or a sequence having 75% or greater, 80% or greater, 85% or greater, 90% or greater, 95% or greater, 98% or greater, 99% or greater identity thereto), with a light chain variable domain of any one of SEQ ID NO:69, SEQ ID NO:70, SEQ ID NO:71, SEQ ID NO:72 or SEQ ID NO:138 (or a sequence having 75% or greater, 80% or greater, 85% or greater, 90% or greater, 95% or greater, 98% or greater, or 99% or greater identity to any of SEQ ID NO:69, SEQ ID NO:70, SEQ ID NO:71, SEQ ID NO:72 or SEQ ID NO:138);

a heavy chain variable domain of SEQ ID NO:54 (or a sequence having 75% or greater, 80% or greater, 85% or greater, 90% or greater, 95% or greater, 98% or greater, 99% or greater identity thereto), with a light chain variable domain of any one of SEQ ID NO:69, SEQ ID NO:70, SEQ ID NO:71, SEQ ID NO:72 or SEQ ID NO:138 (or a sequence having 75% or greater, 80% or greater, 85% or greater, 90% or greater, 95% or greater, 98% or greater, or 99% or greater identity to any of SEQ ID NO:69, SEQ ID NO:70, SEQ ID NO:71, SEQ ID NO:72 or SEQ ID NO:138);

a heavy chain variable domain of SEQ ID NO:55 (or a sequence having 75% or greater, 80% or greater, 85% or greater, 90% or greater, 95% or greater, 98% or greater, 99% or greater identity thereto), with a light chain variable domain of any one of SEQ ID NO:69, SEQ ID NO:70, SEQ ID NO:71, SEQ ID NO:72 or SEQ ID NO:138 (or a sequence having 75% or greater, 80% or greater, 85% or greater, 90% or greater, 95% or greater, 98% or greater, or 99% or greater identity to any of SEQ ID NO:69, SEQ ID NO:70, SEQ ID NO:71, SEQ ID NO:72 or SEQ ID NO:138);

a heavy chain variable domain of SEQ ID NO:56 (or a sequence having 75% or greater, 80% or greater, 85% or greater, 90% or greater, 95% or greater, 98% or greater, 99% or greater identity thereto), with a light chain variable domain of any one of SEQ ID NO:69, SEQ ID NO:70, SEQ ID NO:71, SEQ ID NO:72 or SEQ ID NO:138 (or a sequence having 75% or greater, 80% or greater, 85% or greater, 90% or greater, 95% or greater, 98% or greater, or 99% or greater identity to any of SEQ ID NO:69, SEQ ID NO:70, SEQ ID NO:71, SEQ ID NO:72 or SEQ ID NO:138);

a heavy chain variable domain of SEQ ID NO:57 (or a sequence having 75% or greater, 80% or greater, 85% or greater, 90% or greater, 95% or greater, 98% or greater, 99% or greater identity thereto), with a light chain variable domain of any one of SEQ ID NO:69, SEQ ID NO:70, SEQ ID NO:71, SEQ ID NO:72 or SEQ ID NO:138 (or a sequence having 75% or greater, 80% or greater, 85% or greater, 90% or greater, 95% or greater, 98% or greater, or 99% or greater identity to any of SEQ ID NO:69, SEQ ID NO:70, SEQ ID NO:71, SEQ ID NO:72 or SEQ ID NO:138);

a heavy chain variable domain of SEQ ID NO:58 (or a sequence having 75% or greater, 80% or greater, 85% or greater, 90% or greater, 95% or greater, 98% or greater, 99% or greater identity thereto), with a light chain variable domain of any one of SEQ ID NO:69, SEQ ID NO:70, SEQ ID NO:71, SEQ ID NO:72 or SEQ ID NO:138 (or a sequence having 75% or greater, 80% or greater, 85% or greater, 90% or greater, 95% or greater, 98% or greater, or 99% or greater identity to any of SEQ ID NO:69, SEQ ID NO:70, SEQ ID NO:71, SEQ ID NO:72 or SEQ ID NO:138);

a heavy chain variable domain of SEQ ID NO:59 (or a sequence having 75% or greater, 80% or greater, 85% or greater, 90% or greater, 95% or greater, 98% or greater, 99% or greater identity thereto), with a light chain variable domain of any one of SEQ ID NO:69, SEQ ID NO:70, SEQ ID NO:71, SEQ ID NO:72 or SEQ ID NO:138 (or a sequence having 75% or greater, 80% or greater, 85% or greater, 90% or greater, 95% or greater, 98% or greater, or 99% or greater identity to any of SEQ ID NO:69, SEQ ID NO:70, SEQ ID NO:71, SEQ ID NO:72 or SEQ ID NO:138);

a heavy chain variable domain of SEQ ID NO:60 (or a sequence having 75% or greater, 80% or greater, 85% or greater, 90% or greater, 95% or greater, 98% or greater, 99% or greater identity thereto), with a light chain variable domain of any one of SEQ ID NO:69, SEQ ID NO:70, SEQ ID NO:71, SEQ ID NO:72 or SEQ ID NO:138 (or a sequence having 75% or greater, 80% or greater, 85% or greater, 90% or greater, 95% or greater, 98% or greater, or 99% or greater identity to any of SEQ ID NO:69, SEQ ID NO:70, SEQ ID NO:71, SEQ ID NO:72 or SEQ ID NO:138);

a heavy chain variable domain of SEQ ID NO:61 (or a sequence having 75% or greater, 80% or greater, 85% or greater, 90% or greater, 95% or greater, 98% or greater, 99% or greater identity thereto), with a light chain variable domain of any one of SEQ ID NO:69, SEQ ID NO:70, SEQ ID NO:71, SEQ ID NO:72 or SEQ ID NO:138 (or a sequence having 75% or greater, 80% or greater, 85% or greater, 90% or greater, 95% or greater, 98% or greater, or 99% or greater identity to any of SEQ ID NO:69, SEQ ID NO:70, SEQ ID NO:71, SEQ ID NO:72 or SEQ ID NO:138);

a heavy chain variable domain of SEQ ID NO:62 (or a sequence having 75% or greater, 80% or greater, 85% or greater, 90% or greater, 95% or greater, 98% or greater, 99% or greater identity thereto), with a light chain variable domain of any one of SEQ ID NO:69, SEQ ID NO:70, SEQ ID NO:71, SEQ ID NO:72 or SEQ ID NO:138 (or a sequence having 75% or greater, 80% or greater, 85% or greater, 90% or greater, 95% or greater, 98% or greater, or 99% or greater identity to any of SEQ ID NO:69, SEQ ID NO:70, SEQ ID NO:71, SEQ ID NO:72 or SEQ ID NO:138);

a heavy chain variable domain of SEQ ID NO:64 (or a sequence having 75% or greater, 80% or greater, 85% or greater, 90% or greater, 95% or greater, 98% or greater, 99% or greater identity thereto), with a light chain variable domain of any one of SEQ ID NO:69, SEQ ID NO:70, SEQ ID NO:71, SEQ ID NO:72 or SEQ ID NO:138 (or a sequence having 75% or greater, 80% or greater, 85% or greater, 90% or greater, 95% or greater, 98% or greater, or 99% or greater identity to any of SEQ ID NO:69, SEQ ID NO:70, SEQ ID NO:71, SEQ ID NO:72 or SEQ ID NO:138);

a heavy chain variable domain of SEQ ID NO:64 (or a sequence having 75% or greater, 80% or greater, 85% or greater, 90% or greater, 95% or greater, 98% or greater, 99% or greater identity thereto), with a light chain variable domain of any one of SEQ ID NO:69, SEQ ID NO:70, SEQ ID NO:71, SEQ ID NO:72 or SEQ ID NO:138 (or a sequence having 75% or greater, 80% or greater, 85% or greater, 90% or greater, 95% or greater, 98% or greater, or 99% or greater identity to any of SEQ ID NO:69, SEQ ID NO:70, SEQ ID NO:71, SEQ ID NO:72 or SEQ ID NO:138);

a heavy chain variable domain of SEQ ID NO:65 (or a sequence having 75% or greater, 80% or greater, 85% or greater, 90% or greater, 95% or greater, 98% or greater, 99% or greater identity thereto), with a light chain variable domain of any one of SEQ ID NO:69, SEQ ID NO:70, SEQ ID NO:71, SEQ ID NO:72 or SEQ ID NO:138 (or a sequence having 75% or greater, 80% or greater, 85% or greater, 90% or greater, 95% or greater, 98% or greater, or 99% or greater identity to any of SEQ ID NO:69, SEQ ID NO:70, SEQ ID NO:71, SEQ ID NO:72 or SEQ ID NO:138);

a heavy chain variable domain of SEQ ID NO:66 (or a sequence having 75% or greater, 80% or greater, 85% or greater, 90% or greater, 95% or greater, 98% or greater, 99% or greater identity thereto), with a light chain variable domain of any one of SEQ ID NO:69, SEQ ID NO:70, SEQ ID NO:71, SEQ ID NO:72 or SEQ ID NO:138 (or a sequence having 75% or greater, 80% or greater, 85% or greater, 90% or greater, 95% or greater, 98% or greater, or 99% or greater identity to any of SEQ ID NO:69, SEQ ID NO:70, SEQ ID NO:71, SEQ ID NO:72 or SEQ ID NO:138);

a heavy chain variable domain of SEQ ID NO:67 (or a sequence having 75% or greater, 80% or greater, 85% or greater, 90% or greater, 95% or greater, 98% or greater, 99% or greater identity thereto), with a light chain variable domain of any one of SEQ ID NO:69, SEQ ID NO:70, SEQ ID NO:71, SEQ ID NO:72 or SEQ ID NO:138 (or a sequence having 75% or greater, 80% or greater, 85% or greater, 90% or greater, 95% or greater, 98% or greater, or 99% or greater identity to any of SEQ ID NO:69, SEQ ID NO:70, SEQ ID NO:71, SEQ ID NO:72 or SEQ ID NO:138); and a heavy chain variable domain of SEQ ID NO:68 (or a sequence having 75% or greater, 80% or greater, 85% or greater, 90% or greater, 95% or greater, 98% or greater, 99% or greater identity thereto), with a light chain variable domain of any one of SEQ ID NO:69, SEQ ID NO:70, SEQ ID NO:71, SEQ ID NO:72 or SEQ ID NO:138 (or a sequence having 75% or greater, 80% or greater, 85% or greater, 90% or greater, 95% or greater, 98% or greater, or 99% or greater identity to any of SEQ ID NO:69, SEQ ID NO:70, SEQ ID NO:71, SEQ ID NO:72 or SEQ ID NO:138).

In a particular embodiment, there is provided an antigen binding protein comprising a heavy chain variable region having amino acid sequence as set out in a SEQ ID NO:53, 54 55 or 56, and a light chain variable region having an amino acid sequence as set out in SEQ ID NO:138.

The binding protein may be an antibody, in particular, a humanised or human antibody, or an antigen binding fragment thereof.

In another aspect, the invention provides a chimeric antibody, comprising a variable heavy chain domain of SEQ ID NO:28 and a variable light chain domain of SEQ ID NO:29, or a variable heavy chain domain of SEQ ID NO:73 and a variable light chain domain of SEQ ID NO:74.

The antigen binding protein of the invention may not inhibit TSLP signalling. In an embodiment, the antigen binding protein does not inhibit TSLP signalling.

The invention also provides a nucleic acid molecule encoding an antigen binding protein of the present invention. In an embodiment, the invention provides nucleic acid molecules of SEQ ID NO:30-38, SEQ ID NO:75-113, SEQ ID NO:119-120, and SEQ ID NOs:122, 124, 126, 128 and 130. The invention also provides an expression vector comprising a nucleic acid molecule as defined herein, and a recombinant host cell comprising an expression vector as defined herein. The expression vector may comprise a nucleic acid molecule of any one or more of SEQ ID NO:30-38, SEQ ID NO:75-113, and SEQ ID NO:119-120, and SEQ ID NOs:122, 124, 126, 128 and 130. In an embodiment, the expression vector comprises a nucleic acid molecule which encodes an antigen binding protein as hereinbefore described. In another embodiment, the invention provides a host cell comprising an expression vector as hereinbefore described. In a further embodiment, the invention provides an antibody expressed by host cell as hereinbefore described.

The invention also provides a method for the production of an antigen binding protein of the present invention which method comprises the step of culturing a host cell as defined above and recovering the antigen binding protein.

The invention also provides an antibody or antigen binding protein according to the invention which is expressed by a host cell comprising a nucleic acid sequence or sequence encoding an antibody or antigen binding fragment according to the invention.

The invention also provides a pharmaceutical composition comprising an antigen binding protein of the present invention and a pharmaceutically acceptable carrier or excipient.

The invention also provides a method of treating a subject afflicted with an autoimmune or inflammatory disease, which method comprises the step of administering to the subject an antigen binding protein of the present invention.

The invention also provides a method of treating a subject afflicted with a disease in which pathogenic $T_H17$ cells are implicated, which method comprises the step of administering to the subject an antigen binding protein of the present invention.

The invention also provides a method of treating a subject afflicted with a disease associated with upregulated expression of IL-17, which method comprises the step of administering to the subject an antigen binding protein of the present invention.

In particular, the autoimmune or inflammatory disease, the disease in which pathogenic $T_H17$ cells are implicated, or the disease associated with up-regulated expression of IL17 may be multiple sclerosis (MS), SLE, rheumatoid arthritis, Behcet's disease or asthma. In an embodiment, the antigen binding protein of the invention will be useful in a method of treating multiple sclerosis. Other diseases which may be treated by the administration of the antigen binding proteins of the invention are described herein.

The invention also provides an antigen binding protein as described herein for use in the treatment of a subject afflicted with an autoimmune or inflammatory disease; a disease in which pathogenic $T_H17$ cells are implicated; or a disease associated with up-regulated expression of IL17.

The invention provides the use of an antigen binding protein as described herein in the manufacture of a medicament for use in the treatment of a subject afflicted with an autoimmune or inflammatory disease; a disease in which pathogenic $T_H17$ cells are implicated; or a disease associated with up-regulated expression of IL17.

Other aspects and embodiments of the invention will be apparent from the detailed description that follows.

BRIEF DESCRIPTION OF THE DRAWINGS

FIGS. 4A to 4D show the inhibition of IL-7-induced IL-17 production in differentiated human Th17 cells by 1A11 H3L4 (in four different donors).

DETAILED DESCRIPTION

Figure 1:
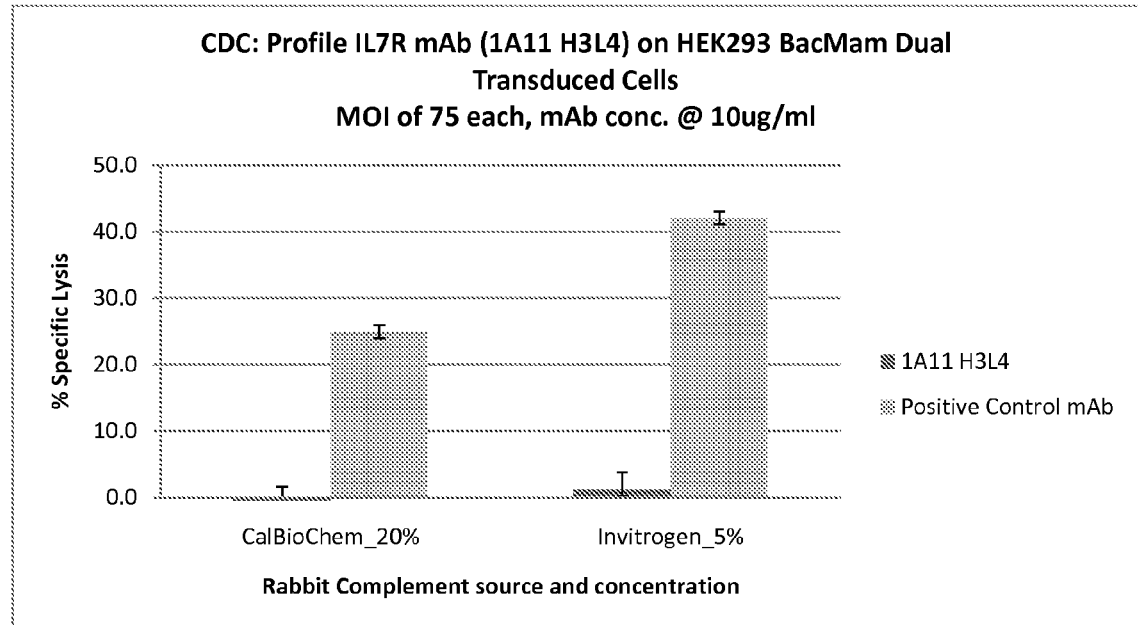
FIG. 1 shows the complement dependent cytotoxicity of the anti-IL7R mAb 1A11 H3L4 on HEK293 cells expressing hIL-7R.

IL-7/IL-7R signalling is critically required for survival and expansion of committed $T_H17$ cells in both mouse and human systems, while its role in $T_H17$ differentiation is not essential compared to that of IL-6 (Liu et al, (2010) Nature Medicine 16:191-197). Surprisingly, the in vivo effect on the immune system by IL-7R antagonism is highly selective in EAE, an animal model for multiple sclerosis, affecting $T_H17$ cells and, to a lesser extent, $T_H1$ cells predominantly of the memory phenotype, and sparing $T_{reg}$ cells. This selectivity appears to play an important role in rebalancing the ratio of pathogenic $T_H17$ cells and $T_{reg}$ cells by IL-7R antagonism in EAE and is attributable to the treatment efficacy.

The role of IL-7/IL-7R signalling in $T_H17$ cell survival and expansion supports the treatment efficacy of IL-7R antagonism in human autoimmune diseases, such as MS. IL-7 neutralization or IL-7R antagonism is likely to have unique therapeutic advantages. On one hand, the treatment offers the selectivity that distinguishes pathogenic $T_H1$ and $T_H17$ cells from $T_{reg}$ and unrelated immune cells. On the other hand, additional therapeutic advantages of IL-7R antagonism involve its selective effect on survival and expansion of differentiated $T_H17$ as opposed to $T_H17$ differentiation. It is conceivable that targeting in vivo maintenance of committed $T_H17$ versus $T_H17$ differentiation is more efficacious in a therapeutic context. Inhibition of IL-7 receptor mediated signalling therefore provides a promising therapeutic intervention for the treatment of autoimmune or inflammatory diseases.

The term IL-7R mediated signalling, as used herein, means the biological effect instigated by the IL-7 receptor complex when bound by its ligand, IL-7. IL-7R mediated signalling therefore includes, but is not necessarily limited to, one or more, or all, of IL-7 induced phosphorylation of STAT-5, IL-7 induced expansion of $T_H17$ cells and IL-7 induced survival of $T_H17$ cells.

Murine antibodies 1A11 and 6A3 are described in patent application number PCT/US2009/053136 (WO2010/017468). These antibodies specifically bind to the alpha chain of the human IL-7 receptor, CD127 (SEQ ID NO:1). The variable domains of these antibodies are described in SEQ ID NO:8 and 9 ($V_H$, Vκ 1A11, respectively) and SEQ ID NO:45 and 46 ($V_H$, Vκ 6A3, respectively).

The present invention provides antigen binding proteins comprising one or more of the complementarity determining regions (CDRs) of 1A11 or 6A3, and variants thereof. The antigen binding proteins may bind to and neutralise IL-7R signalling. In one embodiment, the invention provides humanised antibodies, comprising the from one to six of the CDRs from murine antibodies 1A11 or 6A3 (the donor antibody) in an a human acceptor antibody.

The term "antigen binding protein" as used herein refers to antibodies, antibody fragments and other protein constructs, such as domains, which are capable of binding to CD127. In an embodiment, the antigen binding protein is an antibody.

The term "antibody" is used herein in the broadest sense to refer to molecules with an immunoglobulin-like domain and includes monoclonal, recombinant, polyclonal, chimeric, humanised, bispecific and heteroconjugate antibodies; a single variable domain, a domain antibody, antigen binding fragments, immunologically effective fragments, single chain Fv, diabodies, Tandabs™, etc (for a summary of alternative "antibody" formats see Holliger and Hudson, Nature Biotechnology, 2005, Vol 23, No. 9, 1126-1136).

The phrase "single variable domain" refers to an antigen binding protein variable domain (for example, $V_H$, $V_{HH}$, $V_L$) that specifically binds an antigen or epitope independently of a different variable region or domain.

A "domain antibody" or "dAb" may be considered the same as a "single variable domain" which is capable of binding to an antigen. A single variable domain may be a human antibody variable domain, but also includes single antibody variable domains from other species such as rodent (for example, as disclosed in WO 00/29004), nurse shark and Camelid $V_{HH}$ dAbs. Camelid $V_{HH}$ are immunoglobulin single variable domain polypeptides that are derived from species including camel, llama, alpaca, dromedary, and guanaco, which produce heavy chain antibodies naturally devoid of light chains. Such $V_{HH}$ domains may be humanised according to standard techniques available in the art, and such domains are considered to be "domain antibodies". As used herein $V_H$ includes camelid $V_{HH}$ domains.

As used herein the term "domain" refers to a folded protein structure which has tertiary structure independent of the rest of the protein. Generally, domains are responsible for discrete functional properties of proteins, and in many cases may be added, removed or transferred to other proteins without loss of function of the remainder of the protein and/or of the domain. A "single variable domain" is a folded polypeptide domain comprising sequences characteristic of antibody variable domains. It therefore includes complete antibody variable domains and modified variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain. A domain can bind an antigen or epitope independently of a different variable region or domain.

An antigen binding fragment may be provided by means of arrangement of one or more CDRs on non-antibody protein scaffolds such as a domain. A non-antibody protein scaffold or domain is one that has been subjected to protein engineering in order to obtain binding to a ligand other than its natural ligand, for example a domain which is a derivative of a scaffold selected from: CTLA-4 (Evibody); lipocalin; Protein A derived molecules such as Z-domain of Protein A (Affibody, SpA), A-domain (Avimer/Maxibody); heat shock proteins such as GroEl and GroES; transferrin (trans-body); ankyrin repeat protein (DARPin); peptide aptamer; C-type lectin domain (Tetranectin); human γ-crystallin and human ubiquitin (affilins); PDZ domains; scorpion toxinkunitz type domains of human protease inhibitors; and fibronectin (adnectin); which has been subjected to protein engineering in order to obtain binding to a ligand other than its natural ligand.

CTLA-4 (Cytotoxic T Lymphocyte-associated Antigen 4) is a CD28-family receptor expressed on mainly CD4+ T-cells. Its extracellular domain has a variable domain-like Ig fold. Loops corresponding to CDRs of antibodies can be substituted with heterologous sequence to confer different binding properties. CTLA-4 molecules engineered to have different binding specificities are also known as Evibodies. For further details see Journal of Immunological Methods 248 (1-2), 31-45 (2001).

Lipocalins are a family of extracellular proteins which transport small hydrophobic molecules such as steroids, bilins, retinoids and lipids. They have a rigid β-sheet secondary structure with a number of loops at the open end of the canonical structure which can be engineered to bind to different target antigens. Anticalins are between 160-180 amino acids in size, and are derived from lipocalins. For further details see Biochim Biophys Acta 1482: 337-350 (2000), US7250297B1 and US20070224633.

An affibody is a scaffold derived from Protein A of *Staphylococcus aureus* which can be engineered to bind to an antigen. The domain consists of a three-helical bundle of approximately 58 amino acids. Libraries have been generated by randomisation of surface residues. For further details see Protein Eng. Des. Sel. 17, 455-462 (2004) and EP1641818A1.

Avimers are multidomain proteins derived from the A-domain scaffold family. The native domains of approximately 35 amino acids adopt a defined disulphide bonded structure. Diversity is generated by shuffling of the natural variation exhibited by the family of A-domains. For further details see Nature Biotechnology 23(12), 1556-1561 (2005) and Expert Opinion on Investigational Drugs 16(6), 909-917 (June 2007).

A transferrin is a monomeric serum transport glycoprotein. Transferrins can be engineered to bind different target antigens by insertion of peptide sequences, such as one or more CDRs, in a permissive surface loop. Examples of engineered transferrin scaffolds include the Trans-body. For further details see J. Biol. Chem 274, 24066-24073 (1999).

Designed Ankyrin Repeat Proteins (DARPins) are derived from Ankyrin which is a family of proteins that mediate attachment of integral membrane proteins to the cytoskeleton. A single ankyrin repeat is a 33 residue motif consisting of two α-helices and a β-turn. They can be engineered to bind different target antigens by: randomising residues in the first α-helix and a β-turn of each repeat; or insertion of peptide sequences, such as one or more CDRs. Their binding interface can be increased by increasing the number of modules (a method of affinity maturation). For further details see J. Mol. Biol. 332, 489-503 (2003), PNAS 100(4), 1700-1705 (2003) and J. Mol. Biol. 369, 1015-1028 (2007) and US20040132028A1.

Fibronectin is a scaffold which can be engineered to bind to antigen. Adnectins consists of a backbone of the natural amino acid sequence of the 10th domain of the 15 repeating units of human fibronectin type III (FN3). Three loops at one end of the β-sandwich can be engineered to enable an Adnectin to specifically recognize a therapeutic target of interest. For further details see Protein Eng. Des. Sel. 18, 435-444 (2005), US20080139791, WO2005056764 and US6818418B1.

Peptide aptamers are combinatorial recognition molecules that consist of a constant scaffold protein, typically thioredoxin (TrxA) which contains a constrained variable peptide loop inserted at the active site. For further details see Expert Opin. Biol. Ther. 5, 783-797 (2005).

Microbodies are derived from naturally occurring microproteins of 25-50 amino acids in length which contain 3-4 cysteine bridges; examples of microproteins include KalataB1 and conotoxin and knottins. The microproteins have a loop which can be engineered to include up to 25 amino acids without affecting the overall fold of the microprotein. For further details of engineered knottin domains, see WO2008098796.

Other binding domains include proteins which have been used as a scaffold to engineer different target antigen binding properties include human γ-crystallin and human ubiquitin (affilins), kunitz type domains of human protease inhibitors, PDZ-domains of the Ras-binding protein AF-6, scorpion toxins (charybdotoxin), C-type lectin domain (tetranectins) are reviewed in Chapter 7—Non-Antibody Scaffolds from Handbook of Therapeutic Antibodies (2007, edited by Stefan Dubel) and Protein Science 15:14-27 (2006). Binding domains of the present invention could be derived from any of these alternative protein domains and any combination of the CDRs of the present invention grafted onto the domain.

An antigen binding fragment or an immunologically effective fragment may comprise partial heavy or light chain variable sequences. Fragments are at least 5, 6, 8 or 10 amino acids in length. Alternatively the fragments are at least 15, at least 20, at least 50, at least 75, or at least 100 amino acids in length.

The term "specifically binds" as used throughout the present specification in relation to antigen binding proteins means that the antigen binding protein binds to CD127 with no or insignificant binding to other (for example, unrelated) proteins—i.e. the antigen binding proteins and antibodies described herein may specifically bind CD127. The term however does not exclude the fact that the antigen binding proteins may also be cross-reactive with CD127 from other species, such as murine CD127, cynomolgus monkey (*Macaca fascicularis*) or marmoset CD127. In an embodiment, the antigen binding protein binds to both cynomolgus monkey and marmoset CD127. The antigen binding proteins described herein may bind to human CD127 with at least 2, 5, 10, 50, 100, or 1000 fold greater affinity than they bind to CD127 from other species.

The binding affinity or equilibrium dissociation constant ($K_D$) of the antigen binding protein-CD127 interaction may be 100 nM or less, 10 nM or less, 2 nM or less or 1 nM or less. Alternatively the $K_D$ may be between 5 and 10 nM; or between 1 and 2 nM. The $K_D$ may be between 1 pM and 500 pM; or between 500 pM and 1 nM. The binding affinity of the antigen binding protein is determined by the association rate constant ($k_a$) and the dissociation rate constant ($k_d$) ($K_D=k_d/k_a$). The binding affinity may be measured by BIACORE™, for example by antigen capture with CD127 coupled onto a CM5 chip by primary amine coupling and antibody capture onto this surface. The BIACORE™ method described in Example 4 may be used to measure binding affinity. Alternatively, the binding affinity can be measured by FORTEbio, for example by antigen capture with CD127 coupled onto a CM5 needle by primary amine coupling and antibody capture onto this surface.

The $k_d$ may be $1\times10^{-3}$ s$^{-1}$ or less, $1\times10^{-4}$ s$^{-1}$ or less, or $1\times10^{-5}$ s$^{-1}$ or less. The $k_d$ may be between $1\times10^{-5}$ s$^{-1}$ and $1\times10^{-4}$ s$^{-1}$; or between $1\times10^{-4}$ s$^{-1}$ and $1\times10^{-3}$ s$^{-1}$. A slow $k_d$ may result in a slow dissociation of the antigen binding protein-ligand complex and improved neutralisation of the ligand.

It will be apparent to those skilled in the art that the term "derived" is intended to define not only the source in the sense of it being the physical origin for the material but also to define material which is structurally identical to the material but which does not originate from the reference source. Thus "residues found in the donor antibody" need not necessarily have been purified from the donor antibody.

By isolated it is intended that the molecule, such as an antigen binding protein, is removed from the environment in which it may be found in nature. For example, the molecule may be purified away from substances with which it would normally exist in nature. For example, the antigen binding protein can be purified to at least 95%, 96%, 97%, 98% or 99%, or greater with respect to a culture media containing the antigen binding protein. The antigen binding proteins and antibodies of the present invention may be isolated antigen binding proteins and antibodies.

A "chimeric antibody" refers to a type of engineered antibody which contains a naturally-occurring variable region (light chain and heavy chains) derived from a donor antibody in association with light and heavy chain constant regions derived from an acceptor antibody.

A "humanised antibody" refers to a type of engineered antibody having one or more of its CDRs derived from a non-human donor immunoglobulin, the remaining immunoglobulin-derived parts of the molecule being derived from one or more human immunoglobulin(s). In addition, framework support residues may be altered to preserve binding affinity (see, e.g., Queen et al. Proc. Natl Acad Sci USA, 86:10029-10032 (1989), Hodgson et al. Bio/Technology, 9:421 (1991)). A suitable human acceptor antibody may be one selected from a conventional database, e.g., the KABAT® database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody. The prior art describes several ways of producing such humanised antibodies, see for example EP-A-0239400 and EP-A-054951.

The term "donor antibody" refers to an antibody which contributes the amino acid sequences of its variable regions, one or more CDRs, or other functional fragments or analogs thereof to a first immunoglobulin partner. The donor therefore provides the altered immunoglobulin coding region and resulting expressed altered antibody with the antigenic specificity and neutralising activity characteristic of the donor antibody.

The term "acceptor antibody" refers to an antibody which is heterologous to the donor antibody, which contributes all (or any portion) of the amino acid sequences encoding its heavy and/or light chain framework regions and/or its heavy and/or light chain constant regions to the first immunoglobulin partner. A human antibody may be the acceptor antibody.

The terms "$V_H$" and "$V_L$" are used herein to refer to the heavy chain variable region and light chain variable region respectively of an antigen binding protein. Vκ is also used to refer to the variable light chain domain.

"CDRs" are defined as the complementarity determining region amino acid sequences of an antigen binding protein. These are the hypervariable regions of immunoglobulin heavy and light chains. There are three heavy chain and three light chain CDRs (or CDR regions) in the variable portion of an immunoglobulin. Thus, "CDRs" as used herein refers to all three heavy chain CDRs, all three light chain CDRs, all heavy and light chain CDRs, or at least two CDRs.

Throughout this specification, amino acid residues in variable domain sequences and full length antibody sequences are numbered according to the Kabat numbering convention, unless otherwise specified. Similarly, the terms "CDR", "CDRL1", "CDRL2", "CDRL3", "CDRH1", "CDRH2", "CDRH3" used in the Examples follow the Kabat numbering convention. For further information, see Kabat et al., Sequences of Proteins of Immunological Interest, 4th Ed., U.S. Department of Health and Human Services, National Institutes of Health (1987).

It will be apparent to those skilled in the art that there are alternative numbering conventions for amino acid residues in variable domain sequences and full length antibody sequences. There are also alternative numbering conventions for CDR sequences, for example those set out in Chothia et al. (1989) Nature 342: 877-883. The structure and protein folding of the antibody may mean that other residues are considered part of the CDR sequence and would be understood to be so by a skilled person. Therefore, the term "corresponding CDR" is used herein to refer to a CDR sequence using any numbering convention, for example those set out in Table 1.

Other numbering conventions for CDR sequences available to a skilled person include "AbM" (University of Bath) and "contact" (University College London) methods. The minimum overlapping region using at least two of the Kabat, Chothia, AbM and contact methods can be determined to provide the "minimum binding unit". The minimum binding unit may be a sub-portion of a CDR.

Table 1 below represents one definition using each numbering convention for each CDR or binding unit. The Kabat numbering scheme is used in Table 1 to number the variable domain amino acid sequence. It should be noted that some of the CDR definitions may vary depending on the individual publication used.

TABLE 1

|    | Kabat CDR      | Chothia CDR | AbM CDR        | Contact CDR    | Minimum binding unit |
|----|----------------|-------------|----------------|----------------|----------------------|
| H1 | 31-35/35A/35B  | 26-32/33/34 | 26-35/35A/35B  | 30-35/35A/35B  | 31-32                |
| H2 | 50-65          | 52-56       | 50-58          | 47-58          | 52-56                |
| H3 | 95-102         | 95-102      | 95-102         | 93-101         | 95-101               |
| L1 | 24-34          | 24-34       | 24-34          | 30-36          | 30-34                |
| L2 | 50-56          | 50-56       | 50-56          | 46-55          | 50-55                |
| L3 | 89-97          | 89-97       | 89-97          | 89-96          | 89-96                |

As used herein, the term "antigen binding site" refers to a site on an antigen binding protein which is capable of specifically binding to an antigen. This may be a single domain (for example, an epitope-binding domain), or single-chain Fv (ScFv) domains or it may be paired $V_H/V_L$ domains as can be found on a standard antibody.

The term "epitope" as used herein refers to that portion of the antigen that makes contact with a particular binding domain of the antigen binding protein. An epitope may be linear, comprising an essentially linear amino acid sequence from the antigen. Alternatively, an epitope may be conformational or discontinuous. For example, a conformational epitope comprises amino acid residues which require an element of structural constraint. A discontinuous epitope comprises amino acid residues that are separated by other sequences, i.e. not in a continuous sequence in the antigen's primary sequence. In the context of the antigen's tertiary and quaternary structure, the residues of a discontinuous epitope are near enough to each other to be bound by an antigen binding protein.

For nucleotide and amino acid sequences, the term "identical" or "sequence identity" indicates the degree of identity between two nucleic acid or two amino acid sequences, and if required when optimally aligned and compared with appropriate insertions or deletions.

The percent identity between two sequences is a function of the number of identical positions shared by the sequences (i.e., % identity=number of identical positions/total number of positions times 100), taking into account the number of gaps, and the length of each gap, which need to be introduced for optimal alignment of the two sequences. The comparison of sequences and determination of percent identity between two sequences can be accomplished using a mathematical algorithm, as described below.

The percent identity between two nucleotide sequences can be determined using the GAP program in the GCG software package, using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. 48:444-453 (1970)) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

In one method, a polynucleotide sequence may be identical to a reference polynucleotide sequence as described herein (see for example SEQ ID NO: 30-39, SEQ ID NO:76-105), that is be 100% identical, or it may include up to a certain integer number of nucleotide alterations as compared to the reference sequence, such as at least 50, 60, 70, 75, 80, 85, 90, 95, 98, or 99% identical. Such alterations are selected from at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in the reference polynucleotide sequence as described herein (see for example SEQ ID NO: 30-39, SEQ ID NO:76-105), by the numerical percent of the respective percent identity (divided by 100) and subtracting that product from said total number of nucleotides in the reference polynucleotide sequence as described herein (see for example SEQ ID NO: 30-39, SEQ ID NO:76-105), or:

$$n_n \leq x_n - (x_n \cdot y),$$

wherein $n_n$ is the number of nucleotide alterations, $x_n$ is the total number of nucleotides in the reference polynucleotide sequence as described herein (see for example SEQ ID NO: 30-39, SEQ ID NO:76-105), and y is 0.50 for 50%, 0.60 for 60%, 0.70 for 70%, 0.75 for 75%, 0.80 for 80%, 0.85 for 85%, 0.90 for 90%, 0.95 for 95%, 0.98 for 98%, 0.99 for 99% or 1.00 for 100%, · is the symbol for the multiplication operator, and wherein any non-integer product of $x_n$ and y is rounded down to the nearest integer prior to subtracting it from $x_n$.

Similarly, a polypeptide sequence may be identical to a polypeptide reference sequence as described herein (see for example SEQ ID NO:1-29, SEQ ID NO:40-75) that is be 100% identical, or it may include up to a certain integer number of amino acid alterations as compared to the reference sequence such that the % identity is less than 100%, such as at least 50, 60, 70, 75, 80, 85, 90, 95, 98, or 99% identical. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the polypeptide sequence encoded by the polypeptide reference sequence as described herein (see for example SEQ ID NO:1-29, SEQ ID NO:40-75) by the numerical percent of the respective percent identity (divided by 100) and then subtracting that product from said total number of amino acids in the polypeptide reference sequence as described herein (see for example SEQ ID NO:1-29, SEQ ID NO:40-75), or:

$$n_a \leq x_a - (x_a \cdot y),$$

wherein $n_a$ is the number of amino acid alterations, $x_a$ is the total number of amino acids in the reference polypeptide sequence as described herein (see for example SEQ ID NO:1-29, SEQ ID NO:40-75), and y is, 0.50 for 50%, 0.60 for 60%, 0.70 for 70%, 0.75 for 75%, 0.80 for 80%, 0.85 for 85%, 0.90 for 90%, 0.95 for 95%, 0.98 for 98%, 0.99 for 99%, or 1.00 for 100%, · is the symbol for the multiplication operator, and wherein any non-integer product of $x_a$ and y is rounded down to the nearest integer prior to subtracting it from $x_a$.

The % identity may be determined across the full length of the sequence, or any fragments thereof; and with or without any insertions or deletions.

The terms "peptide", "polypeptide" and "protein" each refers to a molecule comprising two or more amino acid residues. A peptide may be monomeric or polymeric.

It is well recognised in the art that certain amino acid substitutions are regarded as being "conservative". Amino acids are divided into groups based on common side-chain properties and substitutions within groups that maintain all or substantially all of the binding affinity of the antigen binding protein are regarded as conservative substitutions, see Table 2 below:

TABLE 2

| Side chain | Members |
| --- | --- |
| Hydrophobic | met, ala, val, leu, ile |
| Neutral hydrophilic | cys, ser, thr |
| Acidic | asp, glu |
| Basic | asn, gln, his, lys, arg |
| Residues that influence chain orientation | gly, pro |
| Aromatic | trp, tyr, phe |

The present invention provides an antigen binding protein which binds to CD127 and comprises CDRH3 of SEQ ID NO:4; a variant CDRH3 thereof, or a CDRH3 of SEQ ID NO:132 to SEQ ID NO:137. The antigen binding protein may specifically bind to CD127 and may also neutralise IL-7R activity.

The present invention also provides an antigen binding protein which binds to CD127 and comprises CDRH2 of SEQ ID NO:3; or a variant CDRH2 thereof. The antigen binding protein may specifically bind to CD127 and may also neutralise IL-7R activity.

The antigen binding protein may further comprise in addition to the CDRH3 or CDRH2 sequences described above, one or more CDRs, or all CDRs, in any combination, selected from: CDRH1 (SEQ ID NO:2), CDRH2 (SEQ ID NO:3), CDRH3 (SEQ ID NO:4, or any of SEQ ID NO: 132 to SEQ ID NO:137), CDRL1 (SEQ ID NO:5), CDRL2 (SEQ ID NO:6), and CDRL3 (SEQ ID NO:7); or a variant of any of said CDRs.

For example, the antigen binding protein may comprise CDRH3 (SEQ ID NO:4) and CDRH1 (SEQ ID NO:2), or variants thereof. The antigen binding protein may comprise CDRH3 (SEQ ID NO:4) and CDRH2 (SEQ ID NO:3), or variants thereof. The antigen binding protein may comprise CDRH1 (SEQ ID NO:2) and CDRH2 (SEQ ID NO:3), and CDRH3 (SEQ ID NO:4), or variants thereof.

The antigen binding protein may comprise CDRL1 (SEQ ID NO:5) and CDRL2 (SEQ ID NO:6), or variants thereof. The antigen binding protein may comprise CDRL2 (SEQ ID NO:6) and CDRL3 (SEQ ID NO:7), or variants thereof. The antigen binding protein may comprise CDRL1 (SEQ ID NO:5), CDRL2 (SEQ ID NO:6) and CDRL3 (SEQ ID NO:7), or variants thereof.

The antigen binding protein may comprise CDRH3 (SEQ ID NO:4) and CDRL3 (SEQ ID NO:7), or variants thereof. The antigen binding protein may comprise CDRH3 (SEQ ID NO:4), CDRH2 (SEQ ID NO:3) and CDRL3 (SEQ ID NO:7), or variants thereof. The antigen binding protein may comprise CDRH3 (SEQ ID NO:4), CDRH2 (SEQ ID NO:3), CDRL2 (SEQ ID NO:6) and CDRL3 (SEQ ID NO:7), or variants thereof.

The antigen binding protein may comprise CDRH1 (SEQ ID NO:2), CDRH2 (SEQ ID NO:3), CDRH3 (SEQ ID NO:4), CDRL1 (SEQ ID NO:5), CDRL2 (SEQ ID NO:6) and CDRL3 (SEQ ID NO:7). Alternatively, variant CDRs may be present, or the CDRH3 of SEQ ID NO:4 can be replaced with any of the CDRs of SEQ ID NO:132-137.

The present invention provides an antigen binding protein which binds to CD127 and comprises CDRH3 of SEQ ID NO:41; or a variant CDRH3 thereof. The antigen binding protein may also neutralise IL-7R activity.

The present invention also provides an antigen binding protein which binds to CD127 and comprises CDRH2 of SEQ ID NO:40; or a variant CDRH2 thereof. The antigen binding protein may also neutralise IL-7R activity.

The antigen binding protein may further comprise in addition to the CDRH3 or CDRH2 sequences described above, one or more CDRs, or all CDRs, in any combination, selected from: CDRH1 (SEQ ID NO:39), CDRH2 (SEQ ID NO:40), CDRH3 (SEQ ID NO:41), CDRL1 (SEQ ID NO:42), CDRL2 (SEQ ID NO:43), and CDRL3 (SEQ ID NO:44); or a variant of any of said CDRs.

For example, the antigen binding protein may comprise CDRH3 (SEQ ID NO:41) and CDRH1 (SEQ ID NO:40), or variants thereof. The antigen binding protein may comprise CDRH3 (SEQ ID NO:41) and CDRH2 (SEQ ID NO:40), or variants thereof. The antigen binding protein may comprise CDRH1 (SEQ ID NO:39) and CDRH2 (SEQ ID NO:40), and CDRH3 (SEQ ID NO:41), or variants thereof.

The antigen binding protein may comprise CDRL1 (SEQ ID NO:42) and CDRL2 (SEQ ID NO:43), or variants thereof. The antigen binding protein may comprise CDRL2 (SEQ ID NO:43) and CDRL3 (SEQ ID NO:44), or variants thereof. The antigen binding protein may comprise CDRL1 (SEQ ID NO:42), CDRL2 (SEQ ID NO:43) and CDRL3 (SEQ ID NO:44), or variants thereof.

The antigen binding protein may comprise CDRH3 (SEQ ID NO:41) and CDRL3 (SEQ ID NO:44), or variants thereof. The antigen binding protein may comprise CDRH3 (SEQ ID NO:41), CDRH2 (SEQ ID NO:40) and CDRL3 (SEQ ID NO:44), or variants thereof. The antigen binding protein may comprise CDRH3 (SEQ ID NO:41), CDRH2 (SEQ ID NO:40), CDRL2 (SEQ ID NO:43) and CDRL3 (SEQ ID NO:44), or variants thereof.

The antigen binding protein may comprise CDRH1 (SEQ ID NO:39), CDRH2 (SEQ ID NO:40), CDRH3 (SEQ ID NO:41), CDRL1 (SEQ ID NO:42), CDRL2 (SEQ ID NO:43) and CDRL3 (SEQ ID NO:44). Alternatively, variant CDRs may be present.

The present invention also provides an antigen binding protein which binds to CD127 and comprises the corresponding CDRH3 of the variable domain sequence of SEQ ID NO:8, or a variant CDRH3 thereof, in a human acceptor framework. The antigen binding protein may neutralise CD127 activity. The antigen binding protein may be a human, chimeric or a humanised antibody.

The antigen binding protein may further comprise one or more, or all of the corresponding CDRs selected from the variable domain sequence of SEQ ID NO: 8 and/or SEQ ID NO: 9, or a variant CDR thereof.

The present invention also provides an antigen binding protein which specifically binds to CD127 and comprises the corresponding CDRH3 of the variable domain sequence of SEQ ID NO:45, or a variant CDRH3 thereof, in a human acceptor framework. The antigen binding protein may neutralise CD127 activity. The antigen binding protein may be a human, chimeric or a humanised antibody.

The antigen binding protein may further comprise one or more, or all of the corresponding CDRs selected from the variable domain sequence of SEQ ID NO:45 and/or SEQ ID NO:46, or a variant CDR thereof.

For example, the antigen binding protein may comprise corresponding CDRH3 and corresponding CDRH1, or variants thereof. The antigen binding protein may comprise corresponding CDRH3 and corresponding CDRH2, or variants thereof. The antigen binding protein may comprise corresponding CDRH1, corresponding CDRH2, and corresponding CDRH3; or variants thereof.

The antigen binding protein may comprise corresponding CDRL1 and corresponding CDRL2, or variants thereof. The antigen binding protein may comprise corresponding CDRL2 and corresponding CDRL3, or variants thereof. The antigen binding protein may comprise corresponding CDRL1, corresponding CDRL2 and corresponding CDRL3, or variants thereof.

The antigen binding protein may comprise corresponding CDRH3 and corresponding CDRL3, or variants thereof. The antigen binding protein may comprise corresponding CDRH3, corresponding CDRH2 and corresponding CDRL3, or variants thereof. The antigen binding protein may comprise corresponding CDRH3, corresponding CDRH2, corresponding CDRL2 and corresponding CDRL3, or variants thereof.

The antigen binding protein may comprise corresponding CDRH1, corresponding CDRH2, corresponding CDRH3, corresponding CDRL1, corresponding CDRL2 and corresponding CDRL3, or variants thereof.

The corresponding CDRs can be defined by reference to Kabat (1987), Chothia (1989), AbM or contact methods. One definition of each of the methods can be found at Table 1 and can be applied to the reference heavy chain variable domain (SEQ ID NO:8 or SEQ ID NO:45) and the reference light chain variable domain (SEQ ID NO:9 and SEQ ID NO:46) to determine the corresponding CDR.

The present invention also provides an antigen binding protein which binds to CD127, and comprises a binding unit H3 comprising Kabat residues 95-101 of SEQ ID NO:8, or a variant H3. The antigen binding protein may be a human, humanised or chimeric antigen binding protein, such as an antibody.

The antigen binding protein may further comprise one or more or all binding units selected from: H1 comprising Kabat residues 31-32 of SEQ ID NO:8, H2 comprising Kabat residues 52-56 of SEQ ID NO:8, L1 comprising Kabat residues 30-34 of SEQ ID NO:9, L2 comprising Kabat residues 50-55 of SEQ ID NO:9 and L3 comprising Kabat residues 89-96 of SEQ ID NO:9; or a variant binding unit.

The present invention also provides an antigen binding protein which binds to CD127, and comprises a binding unit H3 comprising Kabat residues 95-101 of SEQ ID NO:45, or a variant H3. The antigen binding protein may be a human, humanised or chimeric antigen binding protein, such as an antibody.

The antigen binding protein may further comprise one or more or all binding units selected from: H1 comprising Kabat residues 31-32 of SEQ ID NO:45, H2 comprising Kabat residues 52-56 of SEQ ID NO:46, L1 comprising Kabat residues 30-34 of SEQ ID NO:46, L2 comprising Kabat residues 50-55 of SEQ ID NO:46 and L3 comprising Kabat residues 89-96 of SEQ ID NO:46; or a variant binding unit.

For example, the antigen binding protein may comprise a binding unit H3 and a binding unit H1, or variants thereof. The antigen binding protein may comprise a binding unit H3 and a binding unit H2, or variants thereof. The antigen binding protein may comprise a binding unit H1, a binding unit H2, and a binding unit H3; or variants thereof.

The antigen binding protein may comprise a binding unit L1 and a binding unit L2, or variants thereof. The antigen binding protein may comprise a binding unit L2 and a binding unit L3, or variants thereof. The antigen binding protein may comprise a binding unit L1, a binding unit L2, and a binding unit L3; or variants thereof.

The antigen binding protein may comprise a binding unit H3 and a binding unit L3, or variants thereof. The antigen binding protein may comprise a binding unit H3, a binding unit H2, and a binding unit L3; or variants thereof. The antigen binding protein may comprise a binding unit H3, a binding unit H2, a binding unit L2, and a binding unit L3; or variants thereof.

The antigen binding protein may comprise a binding unit H1, a binding unit H2, a binding unit H3, a binding unit L1, a binding unit L2, and a binding unit L3; or variants thereof.

A CDR variant or variant binding unit includes an amino acid sequence modified by at least one amino acid, wherein said modification can be chemical or a partial alteration of the amino acid sequence (for example by no more than 10 amino acids), which modification permits the variant to retain the biological characteristics of the unmodified sequence. For example, the variant is a functional variant which binds to CD127. A partial alteration of the CDR amino acid sequence may be by deletion or substitution of one to several amino acids, or by addition or insertion of one to several amino acids, or by a combination thereof (for example by no more than 10 amino acids). The CDR variant or binding unit variant may contain 1, 2, 3, 4, 5 or 6 amino acid substitutions, additions or deletions, in any combination, in the amino acid sequence. The CDR variant or binding unit variant may contain 1, 2 or 3 amino acid substitutions, insertions or deletions, in any combination, in the amino acid sequence. The substitutions in amino acid residues may be conservative substitutions, for example, substituting one hydrophobic amino acid for an alternative hydrophobic amino acid. For example leucine may be substituted with valine, or isoleucine.

The CDRs L1, L2, L3, H1, H2 and H3 tend to structurally exhibit one of a finite number of main chain conformations (canonicals). The particular canonical structure class of a CDR is defined by both the length of the CDR and by the loop packing, determined by residues located at key positions in both the CDRs and the framework regions (structurally determining residues or SDRs). Martin and Thornton (1996; J Mol Biol 263:800-815) have generated an automatic method to define the "key residue" canonical templates. Cluster analysis is used to define the canonical classes for sets of CDRs, and canonical templates are then identified by analysing buried hydrophobics, hydrogen-bonding residues, and conserved glycines and prolines. The CDRs of antibody sequences can be assigned to canonical classes by comparing the sequences to the key residue templates and scoring each template using identity or similarity matrices.

Based on the canonical class of the 1A11 H3L4 antibody (SEQ ID NO: 13 (1A11.H3 $V_H$) or SEQ ID NO:22 (1A11.L4 $V_\kappa$)), functional antibody binding could be predicted to be maintained in the presence of the following CDR substitutions, where the amino acid before the Kabat number is the original amino acid sequence of and the amino acid sequence at the end of the Kabat number is the substituted amino acid:

CDRH1 Canonicals:
  Y32I, Y32H, Y32F, Y32T, Y32N, Y32C, Y32E, Y32D
  T33Y, T33A, T33W, T33G, T33L, T33V
  M34I, M34V, M34W
  N35E, N35H, N35Q, N35S, N35Y, N35T
CDRH2 Canonicals:
  L50R, L50E, L50W, L50Y, L50G, L50Q, L50V, L50N, L50K, N50A
  I51L, I51V, I51T, I51S, I51N
  N52D, N52L, N52S, N52Y
  Y53A, Y53G, Y53S, Y53K, Y53T, Y53N
  N54S, N54T, N54K, N54D, N54G
  V56Y, V56R, V56E, V56D, V56G, V56S, V56A
  S58K, S58N, S58T, S58D, S58R, S58G, S58F, S58Y
CDRH3 Canonicals:
  V102Y, V102H, V102I, V102S, V102D, V102G
CDRL1 Canonicals:
  S29V
  M33L
CDRL3 Canonicals:
  Q89L
  E90Q
  W91Y
  Y93S, Y93R Thus, the antigen binding protein may or may not have any of the above substitutions within the CDR positions. There may be multiple substitutions per variant CDR, per corresponding CDR, per binding unit, per heavy or light chain variable region, per heavy or light chain, and per antigen binding protein, and therefore any combination of substitution may be present in the antigen binding protein of the invention, provided that the canonical structure of the CDR is maintained.

For the avoidance of doubt, the above-described substitutions should not be construed as limiting the possible CDR substitutions which may be performed whilst still retaining a functional anti-CD127 antibody.

The antigen binding protein comprising the CDRs, corresponding CDRs, variant CDRs, binding units or variant binding units described, may display a potency for binding to CD127, as demonstrated by EC50, of within 10 fold, or within 5 fold of the potency demonstrated by 1A11c (chimera, $V_H$-SEQ ID NO:28, $V_\kappa$-SEQ ID NO:29) or 6A3c (chimera, $V_H$-SEQ ID NO:74, $V_\kappa$-SEQ ID NO:75). Potency for binding to CD127, may be demonstrated by various methods, such as binding affinity (e.g. by BIACORE™), or EC50 (e.g. by an ELISA assay).

As discussed above, the particular canonical structure class of a CDR is defined by both the length of the CDR and by the loop packing, determined by residues located at key positions in both the CDRs and the framework regions. Thus in addition to the CDRs listed in SEQ ID NO:2-6, variant CDRs, corresponding CDRs, binding units, or variants thereof, substitutions may be made in the framework residues of an antigen binding protein of the invention, based on the canonical class, while retaining a functional antibody. Such may include (using Kabat numbering):

Heavy chain: V, I or G at position 2; L or V at position 4; L, I, M or V at position 20; C at position 22; T, A, V, G or S at position 24; G at position 26; I, F, L or S at position 29; W at position 36; W or Y at position 47; I, M, V or L at position 48; I, L, F, M or V at position 69; V, A, R or L at position 71; A, L, V, Y or F at position 78; L or M at position 80; Y or F at position 90; C at position 92; and/or R, K, G, S, H or N at position 94; and/or Light chain: I, L or V at position 2; V, Q, L or E at position 3; M or L at position 4; C at position 23; W at position 35; Y, L or F at position 36; S, L, R or V at position 46; Y, H, F or K at position 49; Y or F at position 71; C at position 88; and/or F at position 98.

Any one, any combination, or all of the framework positions described above may be present in the antigen binding protein of the invention. There may be multiple variant framework canonical positions per heavy or light chain variable region, per heavy or light chain, and per antigen binding protein, and therefore any combination may be present in the antigen binding protein of the invention, provided that the canonical structure of the framework is maintained.

For example, the heavy chain variable framework may comprise V at position 2, L at position 4, V at position 20, C at position 22, A at position 24, G at position 26, F at position 29, W at position 36, W at position 47, M at position 48, L at position 69, R at position 71, A at position 78, M at position 80, Y at position 90, C at position 92, and R at position 94, and, for example, the light chain variable framework may comprise I at position 2, L at position 4, C at position 23, W at position 35, Y at position 36, F at position 71, C at position 88, E at position 90, and Y at position 93.

One or more of the CDRs, corresponding CDRs, variant CDRs or binding units described herein may be present in the context of a human framework, for example as a humanised or chimeric variable domain.

The humanised heavy chain variable domain may comprise the CDRs listed in SEQ ID NO:2-4, or SEQ ID NO:39-41; variant CDRs thereof; corresponding CDRs; binding units; or variants thereof, within an acceptor antibody framework having 75% or greater, 80% or greater, 85% or greater, 90% or greater, 95% or greater, 98% or greater, 99% or greater or 100% identity in the framework regions to the human acceptor variable domain sequence in SEQ ID NO: 116.

The humanised light chain variable domain may comprise the CDRs listed in SEQ ID NO: 5-7 or SEQ ID NO:42-44; variant CDRs thereof; corresponding CDRs; binding units; or variants thereof, within an acceptor antibody framework having 75% or greater, 80% or greater, 85% or greater, 90% or greater, 95% or greater, 98% or greater, 99% or greater or 100% identity in the framework regions to the human acceptor variable domain sequence in SEQ ID NO: 117.

The invention also provides an antigen binding protein which binds to CD127 and comprises a heavy chain variable region selected from any one of SEQ ID NO:10, 11, 12, 13, 14, 15, 16, 17, 121, 123, 125, 127, 129 or 131. The antigen binding protein may comprise a light chain variable region selected from any one of SEQ ID NO:18, 19, 20, 21, 22, 23, 24, 25, 26 or 27. Any of the heavy chain variable regions may be combined with any of the light chain variable regions. The antigen binding protein may also neutralise CD127.

The invention also provides an antigen binding protein which binds to CD127 and comprises a heavy chain variable region selected from any one of SEQ ID NO:48, 49, 50, 51, 52, 53, 54, 55, 56, 57, 58, 59, 60, 61, 62, 63, 64, 65, 66, 67, 68 or 69. The antigen binding protein may comprise a light chain variable region selected from any one of SEQ ID NO:70, 71, 72, 73 or 138. Any of the heavy chain variable regions may be combined with any of the light chain variable regions. The antigen binding protein may also neutralise CD127.

The antibody heavy chain variable region may have 75% or greater, 80% or greater, 85% or greater, 90% or greater, 95% or greater, 98% or greater, 99% or greater or 100% identity to any one of SEQ ID NO:10, 11, 12, 13, 14, 15, 16, 17, 121, 123, 125, 127, 129 or 131; or SEQ ID NO:48, 49, 50, 51, 52, 53, 54, 55, 56, 57, 58, 59, 60, 61, 62, 63, 64, 65, 66, 67, 68 or 69.

The antibody light chain variable region may have 75% or greater, 80% or greater, 85% or greater, 90% or greater, 95% or greater, 98% or greater, 99% or greater, or 100% identity to any one of SEQ ID NO:18, 19, 20, 21, 22, 23, 24, 25, 26 or 27; or SEQ ID NO:70, 71, 72, 73 or 138.

The percentage identity of the variants of SEQ ID NO: 10, 11, 12, 13, 14, 15, 16, 17, 18, 19, 20, 21, 22, 23, 24, 25, 26, 27, 121, 123, 125, 127, 129 or 131 may be determined across the full length of the sequence.

The antibody heavy chain variable region may be a variant of any one of SEQ ID NO:10, 11, 12, 13, 14, 15, 16, 17, 121, 123, 125, 127, 129 or 131. which contains 30, 25, 20, 15, 10, 9, 8, 7, 6, 5, 4, 3, 2 or 1 amino acid substitutions, insertions or deletions.

The antibody light chain variable region may be a variant of any one of SEQ ID NO:18, 19, 20, 21, 22, 23, 24, 25, 26 or 27 which contains 30, 25, 20, 15, 10, 9, 8, 7, 6, 5, 4, 3, 2 or 1 amino acid substitutions, insertions or deletions;

For example, the canonical CDRs and canonical framework residue substitutions described above may also be present in the variant heavy or light chain variable regions as variant sequences that are at least 75% identical or which contain up to 30 amino acid substitutions.

In another embodiment, the antibody heavy chain variable region may be a variant of any one of SEQ ID NO: 48, 49, 50, 51, 52, 53, 54, 55, 56, 57, 58, 59, 60, 61, 62, 63, 64, 65, 66, 67, 68 or 69 which contains 30, 25, 20, 15, 10, 9, 8, 7, 6, 5, 4, 3, 2 or 1 amino acid substitutions, insertions or deletions. The antibody light chain variable region may be a variant of any one of SEQ ID NO: 70, 71, 72 or 73 which contains 30, 25, 20, 15, 10, 9, 8, 7, 6, 5, 4, 3, 2 or 1 amino acid substitutions, insertions or deletions.

For example, the canonical CDRs and canonical framework residue substitutions described above may also be present in the variant heavy or light chains as variant sequences that are at least 75% identical or which contain up to 30 amino acid substitutions.

Any of the heavy chain variable regions of the invention may be combined with a suitable human constant region. Any of the light chain variable regions of the invention may be combined with a suitable constant region.

The invention also provides an antigen binding protein which specifically binds to CD127 and comprises any the following heavy chain and light chain variable domain combination: 1A11.H3.L4 (SEQ ID NO:13 and SEQ ID NO:22), or an antigen binding protein which has a heavy chain variable domain having at least 75% identity to SEQ ID NO:13 and a light chain variable domain having at least 75% identity to SEQ ID NO:22. The antigen binding protein may also neutralise CD127.

Antigen binding proteins as described above, for example variants with a partial alteration of the sequence by chemical modification and/or insertion, deletion or substitution of one or more amino acid residues, or those with 75% or greater, 80% or greater, 85% or greater, 90% or greater, 95% or greater, 98% or greater, or 99% or greater identity to any of the sequences described above, may display a potency for binding to CD127, as demonstrated by EC50 or BIA-CORE™, of within 10 fold, or within 5 fold of the potency demonstrated by 1A11 or 6A3. Potency for binding to CD127, may be demonstrated by EC50, carried out by an ELISA assay, or by binding affinity, carried out by BIA-CORE™'

The present inventors have also determined experimentally that certain positions within CDRH3 may be substituted resulting in an reduced binding affinity (i.e. stronger binding). Such CDRH3 analogues are set out in Table 4. Substitutions at positions N98 and F100b (Kabat numbering) were seen to be particularly effective in increasing affinity. Particular substitutions include N98D, N98E, F100bE, F100bI and F100bV. CDRH3 sequences representing these substitutions are SEQ ID NO:132, 133, 134, 135, 136 and 137, respectively.

The present invention contemplates the incorporation of such substitutions into any of the antibodies described herein.

In an embodiment, the antibody of the invention has a W (Trp) residue at position 100.

It may be desirable to modify the effector function so of the antigen binding fragment—for instance, to enhance ADCC or CDC, half life, etc.

In an embodiment, the antigen binding proteins of the invention may be Fc disabled. One way to achieve Fc disablement comprises the substitutions of alanine residues at positions 235 and 237 (EU index numbering) of the heavy chain constant region. Alternatively, the antigen binding protein may be Fc enabled and not comprise the alanine substitutions at positions 235 and 237.

The antigen binding protein may have a half life of at least 6 hours, at least 1 day, at least 2 days, at least 3 days, at least 4 days, at least 5 days, at least 7 days, or at least 9 days in vivo in humans, or in a murine animal model.

The antigen binding protein may be derived from rat, mouse, primate (e.g. cynomolgus, Old World monkey or Great Ape) or human. The antigen binding protein may be a human, humanised or chimeric antibody. The antigen binding protein may comprise a constant region, which may be of any isotype or subclass. The constant region may be of the IgG isotype, for example IgG1, IgG2, IgG3, IgG4 or variants thereof. The antigen binding protein constant region may be IgG1.

Mutational changes to the Fc effector portion of the antibody can be used to change the affinity of the interaction between the FcRn and antibody to modulate antibody turnover. The half life of the antibody can be extended in vivo. This could be beneficial to patient populations as maximal dose amounts and maximal dosing frequencies could be achieved as a result of maintaining in vivo IC50 for longer periods of time. The Fc effector function of the antibody may be removed, in its entirety or in part, since it may not be desirable to kill those cells expressing CD127. This removal may result in an increased safety profile.

The antigen binding protein comprising a constant region may have reduced ADCC and/or complement activation or effector functionality. The constant domain may comprise a naturally disabled constant region of IgG2 or IgG4 isotype or a mutated IgG1 constant domain. Examples of suitable modifications are described in EP0307434. One way to achieve Fc disablement comprises the substitutions of alanine residues at positions 235 and 237 (EU index numbering) of the heavy chain constant region.

The antigen binding protein may comprise one or more modifications selected from a mutated constant domain such that the antibody has enhanced effector functions/ADCC and/or complement activation. Examples of suitable modifications are described in Shields et al. J. Biol. Chem (2001) 276:6591-6604, Lazar et al. PNAS (2006) 103:4005-4010 and U.S. Pat. No. 6,737,056, WO2004063351 and WO2004029207.

The antigen binding protein may comprise a constant domain with an altered glycosylation profile such that the antigen binding protein has enhanced effector functions/ADCC and/or complement activation. Examples of suitable methodologies to produce an antigen binding protein with an altered glycosylation profile are described in WO2003/011878, WO2006/014679 and EP1229125.

The CD127 polypeptide to which the antigen binding protein binds may be a recombinant polypeptide, and may comprise the extracellular domain (ECD), optionally fused to another protein, such as an Fc domain, or may comprise the full length CD127 protein. CD127 may be in solution or may be attached to a solid surface. For example, CD127 may be attached to beads such as magnetic beads. CD127 may be biotinylated. The biotin molecule conjugated to CD127 may be used to immobilize CD127 on a solid surface by coupling biotinstreptavidin on the solid surface.

The present invention also provides a nucleic acid molecule which encodes an antigen binding protein as described herein. The nucleic acid molecule may comprise a sequence encoding (i) one or more CDRHs, the heavy chain variable sequence, or the full length heavy chain sequence; and (ii) one or more CDRLs, the light chain variable sequence, or the full length light chain sequence, with (i) and (ii) on the same nucleic acid molecule. Alternatively, the nucleic acid molecule which encodes an antigen binding protein described herein may comprise sequences encoding (a) one or more CDRHs, the heavy chain variable sequence, or the full length heavy chain sequence; or (b) one or more CDRLs, the light chain variable sequence, or the full length light chain sequence, with (a) and (b) on separate nucleic acid molecules.

The nucleic acid molecule which encodes the heavy chain variable domain may comprise SEQ ID NO:30-36. The nucleic acid molecule which encodes the light chain variable domain may comprise SEQ ID NO:10-113.

The nucleic acid molecule which encodes the heavy chain variable domain may comprise SEQ ID NO:75-96. The nucleic acid molecule which encodes the light chain variable domain may comprise SEQ ID NO:97-100.

The present invention also provides an expression vector comprising a nucleic acid molecule as described herein. Also provided is a recombinant host cell comprising an expression vector as described herein.

The antigen binding protein described herein may be produced in a suitable host cell. A method for the production of the antigen binding protein as described herein may comprise the step of culturing a host cell as described herein and recovering the antigen binding protein. A recombinant transformed, transfected, or transduced host cell may comprise at least one expression cassette, whereby said expression cassette comprises a polynucleotide encoding a heavy chain of the antigen binding protein described herein and further comprises a polynucleotide encoding a light chain of the antigen binding protein described herein. Alternatively, a recombinant transformed, transfected or transduced host cell may comprise at least one expression cassette, whereby a first expression cassette comprises a polynucleotide encoding a heavy chain of the antigen binding protein described herein and further comprise a second cassette comprising a polynucleotide encoding a light chain of the antigen binding protein described herein. A stably transformed host cell may comprise a vector comprising one or more expression cassettes encoding a heavy chain and/or a light chain of the antigen binding protein described herein. For example such host cells may comprise a first vector encoding the light chain and a second vector encoding the heavy chain.

The host cell may be eukaryotic, for example mammalian. Examples of such cell lines include CHO or NS0. The host cell may be a non-human host cell. The host cell may be a non-embryonic host cell. The host cell may be cultured in a culture media, for example serum-free culture media. The antigen binding protein may be secreted by the host cell into the culture media. The antigen binding protein can be purified to at least 95% or greater (e.g. 98% or greater) with respect to said culture media containing the antigen binding protein.

A pharmaceutical composition comprising the antigen binding protein and a pharmaceutically acceptable carrier is also provided by the present invention. A kit-of-parts comprising the pharmaceutical composition together with instructions for use is further provided. For convenience, the kit-of-parts may comprise the reagents in predetermined amounts with instructions for use.

Antibody Structures
Intact Antibodies

The light chains of antibodies from most vertebrate species can be assigned to one of two types called Kappa and Lambda based on the amino acid sequence of the constant region. Depending on the amino acid sequence of the constant region of their heavy chains, human antibodies can be assigned to five different classes, IgA, IgD, IgE, IgG and IgM. IgG and IgA can be further subdivided into subclasses, IgG1, IgG2, IgG3 and IgG4; and IgA1 and IgA2. Species variants exist with mouse and rat having at least IgG2a, IgG2b.

The more conserved portions of the variable region are called Framework regions (FR). The variable domains of intact heavy and light chains each comprise four FR connected by three CDRs. The CDRs in each chain are held together in close proximity by the FR regions and with the CDRs from the other chain contribute to the formation of the antigen binding site of antibodies.

The constant regions are not directly involved in the binding of the antibody to the antigen but exhibit various effector functions such as participation in antibody dependent cell-mediated cytotoxicity (ADCC), phagocytosis via binding to Fcγ receptor, half-life/clearance rate via neonatal Fc receptor (FcRn) and complement dependent cytotoxicity via the C1q component of the complement cascade.

The human IgG2 constant region has been reported to essentially lack the ability to activate complement by the classical pathway or to mediate antibody-dependent cellular cytotoxicity. The IgG4 constant region has been reported to lack the ability to activate complement by the classical pathway and mediates antibody-dependent cellular cytotoxicity only weakly. Antibodies essentially lacking these effector functions may be termed 'non-lytic' antibodies. It may be desirable to reduce the effector functon of the antibody according to the invention, optionally to the extent that the antibody has essentially no effector function. In an embodiment, the antibody according to the invention is non-lytic. In an embodiment, the antibody according to the invention has essentially no effector function. The antibody may, or may not, be conjugated to another molecule, for instance a molecule intended to modify the effector function such as a cytotoxic moiety or a radioactive moiety. In an embodiment, the antibody is not conjugated to another molecule such as a radiolabel or cytotoxic molecule. In this embodiment, the antibody achieves its functional effect by blocking a natural biological interaction, rather than by a direct cell-killing effect.

Human Antibodies

Human antibodies may be produced by a number of methods known to those of skill in the art. Human antibodies can be made by the hybridoma method using human myeloma or mouse-human heteromyeloma cells lines see Kozbor (1984) J. Immunol 133, 3001, and Brodeur, Monoclonal Antibody Production Techniques and Applications, 51-63 (Marcel Dekker Inc, 1987). Alternative methods include the use of phage libraries or transgenic mice both of which utilize human variable region repertoires (see Winter (1994) Annu. Rev. Immunol 12: 433-455; Green (1999) J. Immunol. Methods 231: 11-23).

Several strains of transgenic mice are now available wherein their mouse immunoglobulin loci has been replaced with human immunoglobulin gene segments (see Tomizuka (2000) PNAS 97: 722-727; Fishwild (1996) Nature Biotechnol. 14: 845-851; Mendez (1997) Nature Genetics, 15: 146-156). Upon antigen challenge such mice are capable of producing a repertoire of human antibodies from which antibodies of interest can be selected.

Phage display technology can be used to produce human antigen binding proteins (and fragments thereof), see McCafferty (1990) Nature 348: 552-553 and Griffiths et al. (1994) EMBO 13: 3245-3260.

The technique of affinity maturation (Marks Bio/technol (1992) 10: 779-783) may be used to improve binding affinity wherein the affinity of the primary human antibody is improved by sequentially replacing the H and L chain variable regions with naturally occurring variants and selecting on the basis of improved binding affinities. Variants of this technique such as "epitope imprinting" are now also available, see for example WO 93/06213; Waterhouse (1993) Nucl. Acids Res. 21: 2265-2266.

Chimeric and Humanised Antibodies

Chimeric antibodies are typically produced using recombinant DNA methods. DNA encoding the antibodies (e.g. cDNA) is isolated and sequenced using conventional procedures (e.g. by using oligonucleotide probes that are capable of binding specifically to genes encoding the H and L chains of the antibody. Hybridoma cells serve as a typical source of such DNA. Once isolated, the DNA is placed into expression vectors which are then transfected into host cells such as E. coli, COS cells, CHO cells or myeloma cells that do not otherwise produce immunoglobulin protein to obtain synthesis of the antibody. The DNA may be modified by substituting the coding sequence for human L and H chains for the corresponding non-human (e.g. murine) H and L constant regions, see for example Morrison (1984) PNAS 81: 6851.

A large decrease in immunogenicity can be achieved by grafting only the CDRs of a non-human (e.g. murine) antibodies ("donor" antibodies) onto human framework ("acceptor framework") and constant regions to generate humanised antibodies (see Jones et al. (1986) Nature 321: 522-525; and Verhoeyen et al. (1988) Science 239: 1534-1536). However, CDR grafting per se may not result in the complete retention of antigen-binding properties and it is frequently found that some framework residues (sometimes referred to as "back mutations") of the donor antibody need to be preserved in the humanised molecule if significant antigen-binding affinity is to be recovered (see Queen et al. (1989) PNAS 86: 10,029-10,033: Co et al. (1991) Nature 351: 501-502). In this case, human variable regions showing the greatest sequence homology to the non-human donor antibody are chosen from a database in order to provide the human framework (FR). The selection of human FRs can be made either from human consensus or individual human antibodies. Where necessary, key residues from the donor antibody can be substituted into the human acceptor framework to preserve CDR conformations. Computer modelling of the antibody maybe used to help identify such structurally important residues, see WO 99/48523.

Alternatively, humanisation maybe achieved by a process of "veneering". A statistical analysis of unique human and murine immunoglobulin heavy and light chain variable regions revealed that the precise patterns of exposed residues are different in human and murine antibodies, and most individual surface positions have a strong preference for a small number of different residues (see Padlan et al. (1991) Mol. Immunol. 28: 489-498; and Pedersen et al. (1994) J. Mol. Biol. 235: 959-973). Therefore it is possible to reduce the immunogenicity of a non-human Fv by replacing exposed residues in its framework regions that differ from those usually found in human antibodies. Because protein antigenicity may be correlated with surface accessibility, replacement of the surface residues may be sufficient to render the mouse variable region "invisible" to the human immune system (see also Mark et al. (1994) in Handbook of Experimental Pharmacology Vol. 113: The pharmacology of Monoclonal Antibodies, Springer-Verlag, 105-134). This procedure of humanisation is referred to as "veneering" because only the surface of the antibody is altered, the supporting residues remain undisturbed. Further alternative approaches include that set out in WO04/006955 and the procedure of Humaneering™ (Kalobios) which makes use of bacterial expression systems and produces antibodies that are close to human germline in sequence (Alfenito-M Advancing Protein Therapeutics January 2007, San Diego, Calif.).

Bispecific Antigen Binding Proteins

A bispecific antigen binding protein is an antigen binding protein having binding specificities for at least two different epitopes. Methods of making such antigen binding proteins are known in the art. Traditionally, the recombinant production of bispecific antigen binding proteins is based on the co-expression of two immunoglobulin H chain-L chain pairs, where the two H chains have different binding specificities, see Millstein et al. (1983) Nature 305: 537-539; WO 93/08829; and Traunecker et al. (1991) EMBO 10: 3655-3659. Because of the random assortment of H and L chains, a potential mixture of ten different antibody structures are produced of which only one has the desired binding specificity. An alternative approach involves fusing the variable domains with the desired binding specificities to heavy chain constant region comprising at least part of the hinge region, CH2 and CH3 regions. The CH1 region containing the site necessary for light chain binding may be present in at least one of the fusions. DNA encoding these fusions, and if desired the L chain are inserted into separate expression vectors and are then co-transfected into a suitable host organism. It is possible though to insert the coding sequences for two or three chains into one expression vector. In one approach, the bispecific antibody is composed of a H chain with a first binding specificity in one arm and a H-L chain pair, providing a second binding specificity in the other arm, see WO 94/04690. Also see Suresh et al. (1986) Methods in Enzymology 121: 210.

Antigen Binding Fragments

Fragments lacking the constant region lack the ability to activate complement by the classical pathway or to mediate antibody-dependent cellular cytotoxicity. Traditionally such fragments are produced by the proteolytic digestion of intact antibodies by e.g. papain digestion (see for example, WO 94/29348) but may be produced directly from recombinantly transformed host cells. For the production of ScFv, see Bird et al. (1988) Science 242: 423-426. In addition, antigen binding fragments may be produced using a variety of engineering techniques as described below.

Fv fragments appear to have lower interaction energy of their two chains than Fab fragments. To stabilise the association of the $V_H$ and $V_L$ domains, they have been linked with peptides (Bird et al. (1988) Science 242: 423-426; Huston et al. (1988) PNAS 85(16): 5879-5883), disulphide bridges (Glockshuber et al. (1990) Biochemistry 29: 1362-1367) and "knob in hole" mutations (Zhu et al. (1997) Protein Sci., 6: 781-788). ScFv fragments can be produced by methods well known to those skilled in the art, see Whitlow et al. (1991) Methods Companion Methods Enzymol, 2: 97-105 and Huston et al. (1993) Int. Rev. Immunol 10: 195-217. ScFv may be produced in bacterial cells such as E. coli or in eukaryotic cells. One disadvantage of ScFv is the monovalency of the product, which precludes an increased avidity due to polyvalent binding, and their short half-life. Attempts to overcome these problems include bivalent $(ScFv')_2$ produced from ScFv containing an additional C-terminal cysteine by chemical coupling (Adams et al. (1993) Can. Res 53: 4026-4034; and McCartney et al. (1995) Protein Eng. 8: 301-314) or by spontaneous site-specific dimerisation of ScFv containing an unpaired C-terminal cysteine residue (see Kipriyanov et al. (1995) Cell. Biophys 26: 187-204). Alternatively, ScFv can be forced to form multimers by shortening the peptide linker to 3 to 12 residues to form "diabodies", see Holliger et al. (1993) PNAS 90: 6444-6448. Reducing the linker still further can result in ScFv trimers ("triabodies", see Kortt et al. (1997) Protein Eng 10: 423-433) and tetramers ("tetrabodies", see Le Gall et al. (1999) FEBS Lett, 453: 164-168). Construction of bivalent ScFv molecules can also be achieved by genetic fusion with protein dimerising motifs to form "miniantibodies" (see Pack et al. (1992) Biochemistry 31: 1579-1584) and "minibodies" (see Hu et al. (1996) Cancer Res. 56: 3055-3061). ScFv-Sc-Fv tandems $((ScFv)_2)$ may also be produced by linking two ScFv units by a third peptide linker, see Kurucz et al. (1995) J. Immol. 154: 4576-4582. Bispecific diabodies can be produced through the noncovalent association of two single chain fusion products consisting of $V_H$ domain from one antibody connected by a short linker to the $V_L$ domain of another antibody, see Kipriyanov et al. (1998) Int. J. Can 77: 763-772. The stability of such bispecific diabodies can be enhanced by the introduction of disulphide bridges or "knob in hole" mutations as described supra or by the formation of single chain diabodies (ScDb) wherein two hybrid ScFv fragments are connected through a peptide linker see Kontermann et al. (1999) J. Immunol. Methods 226:179-188. Tetravalent bispecific molecules are available by e.g. fusing a ScFv fragment to the CH3 domain of an IgG molecule or to a Fab fragment through the hinge region, see Coloma et al. (1997) Nature Biotechnol. 15: 159-163. Alternatively, tetravalent bispecific molecules have been created by the fusion of bispecific single chain diabodies (see Alt et al. (1999) FEBS Lett 454: 90-94. Smaller tetravalent bispecific molecules can also be formed by the dimerization of either ScFv-ScFv tandems with a linker containing a helix-loop-helix motif (DiBi miniantibodies, see Muller et al. (1998) FEBS Lett 432: 45-49) or a single chain molecule comprising four antibody variable domains ($V_H$ and $V_L$) in an orientation preventing intramolecular pairing (tandem diabody, see Kipriyanov et al. (1999) J. Mol. Biol. 293: 41-56). Bispecific $F(ab')_2$ fragments can be created by chemical coupling of Fab' fragments or by heterodimerization through leucine zippers (see Shalaby et al. (1992) J. Exp. Med. 175: 217-225; and Kostelny et al. (1992). J. Immunol. 148: 1547-1553). Also available are isolated $V_H$ and $V_L$ domains (Domantis plc), see U.S. Pat. No. 6,248,516; U.S. Pat. No. 6,291,158; and U.S. Pat. No. 6,172,197.

Heteroconjugate Antibodies

Heteroconjugate antibodies are composed of two covalently joined antibodies formed using any convenient cross-linking methods. See, for example, U.S. Pat. No. 4,676,980.

Other Modifications

The antigen binding proteins of the present invention may comprise other modifications to enhance or change their effector functions. The term "Effector Function" as used herein is meant to refer to one or more of Antibody dependant cell mediated cytotoxic activity (ADCC), Complement-dependant cytotoxic activity (CDC) mediated responses, Fc-mediated phagocytosis and antibody recycling via the FcRn receptor. For IgG antibodies, effector functionalities including ADCC and ADCP are mediated by the interaction of the heavy chain constant region with a family of Fcγ receptors present on the surface of immune cells. In humans these include FcγRI (CD64), FcγRII (CD32) and FcγRIII (CD16). Interaction between the antigen binding protein bound to antigen and the formation of the Fc/Fcγ complex induces a range of effects including cytotoxicity, immune cell activation, phagocytosis and release of inflammatory cytokines.

The interaction between the constant region of an antigen binding protein and various Fc receptors (FcR) is believed to mediate the effector functions of the antigen binding protein. Significant biological effects can be a consequence of effector functionality, in particular, antibody-dependent cellular cytotoxicity (ADCC), fixation of complement (complement dependent cytotoxicity or CDC), and half-life/clearance of the antigen binding protein. Usually, the ability to mediate effector function requires binding of the antigen binding protein to an antigen and not all antigen binding proteins will mediate every effector function.

Effector function can be measured in a number of ways including for example via binding of the FcγRIII to Natural Killer cells or via FcγRI to monocytes/macrophages to measure for ADCC effector function. For example an antigen binding protein of the present invention can be assessed for ADCC effector function in a Natural Killer cell assay. Examples of such assays can be found in Shields et al, 2001 The Journal of Biological Chemistry, Vol. 276, p6591-6604; Chappel et al, 1993 The Journal of Biological Chemistry, Vol 268, p25124-25131; Lazar et al, 2006 PNAS, 103; 4005-4010.

Examples of assays to determine CDC function include that described in 1995 J Imm Meth 184:29-38.

Some isotypes of human constant regions, in particular IgG4 and IgG2 isotypes, essentially lack the functions of a) activation of complement by the classical pathway; and b) antibody-dependent cellular cytotoxicity. Various modifications to the heavy chain constant region of antigen binding proteins may be carried out depending on the desired effector property. IgG1 constant regions containing specific mutations have separately been described to reduce binding to Fc receptors and therefore reduce ADCC and CDC (Duncan et al. Nature 1988, 332; 563-564; Lund et al. J. Immunol. 1991, 147; 2657-2662; Chappel et al. PNAS 1991, 88; 9036-9040; Burton and Woof, Adv. Immunol. 1992, 51; 1-84; Morgan et al., Immunology 1995, 86; 319-324; Hezareh et al., J. Virol. 2001, 75 (24); 12161-12168).

Various modifications to the Fc region of antibodies may be carried out depending on the desired property. For example, specific mutations in the Fc region to render an otherwise lytic antibody, non-lytic are detailed in EP 0629 240 and EP 0307 434 or one may incorporate a salvage receptor binding epitope into the antibody to increase serum half life see U.S. Pat. No. 5,739,277. Human Fcγ receptors include FcγR (I), FcγRIIa, FcγRIIb, FcγRIIIa and neonatal FoRn. Shields et al. (2001) J. Biol. Chem 276: 6591-6604 demonstrated that a common set of IgG1 residues is involved in binding all FcγRs, while FcγRII and FcγRIII utilize distinct sites outside of this common set. One group of IgG1 residues reduced binding to all FcγRs when altered to alanine: Pro-238, Asp-265, Asp-270, Asn-297 and Pro-239. All are in the IgG CH2 domain and clustered near the hinge joining CH1 and CH2. While FcγRI utilizes only the common set of IgG1 residues for binding, FcγRII and FcγRIII interact with distinct residues in addition to the common set. Alteration of some residues reduced binding only to FcγRII (e.g. Arg-292) or FcγRIII (e.g. Glu-293). Some variants showed improved binding to FcγRII or FcγRIII but did not affect binding to the other receptor (e.g. Ser-267Ala improved binding to FcγRII but binding to FcγRIII was unaffected). Other variants exhibited improved binding to FcγRII or FcγRIII with reduction in binding to the other receptor (e.g. Ser-298Ala improved binding to FcγRIII and reduced binding to FcγRII). For FcγRIIIa, the best binding IgG1 variants had combined alanine substitutions at Ser-298, Glu-333 and Lys-334. The neonatal FcRn receptor is believed to be involved in both antibody clearance and the transcytosis across tissues (see Junghans (1997) Immunol. Res 16: 29-57: and Ghetie et al. (2000) Annu. Rev. Immunol, 18: 739-766). Human IgG1 residues determined to interact directly with human FcRn includes Ile253, Ser254, Lys288, Thr307, Gln311, Asn434 and His435. Substitutions at any of the positions described in this section may enable increased serum half-life and/or altered effector properties of the antibodies.

Other modifications include glycosylation variants of the antibodies. Glycosylation of antibodies at conserved positions in their constant regions is known to have a profound effect on antibody function, particularly effector functioning such as those described above, see for example, Boyd et al. (1996) Mol. Immunol, 32: 1311-1318. Glycosylation variants of the antibodies or antigen binding fragments thereof wherein one or more carbohydrate moiety is added, substituted, deleted or modified are contemplated. Introduction of an asparagine-X-serine or asparagine-X-threonine motif creates a potential site for enzymatic attachment of carbohydrate moieties and may therefore be used to manipulate the glycosylation of an antibody. In Raju et al, (2001) Biochemistry 40: 8868-8876 the terminal sialyation of a TNFR-IgG immunoadhesin was increased through a process of regalactosylation and/or resialylation using beta-1,4-galactosyltransferace and/or alpha, 2,3 sialyltransferase, Increasing the terminal sialylation is believed to increase the half-life of the immunoglobulin, Antibodies, in common with most glycoproteins, are typically produced as a mixture of glycoforms. This mixture is particularly apparent when antibodies are produced in eukaryotic, particularly mammalian cells, A variety of methods have been developed to manufacture defined glycoforms, see Zhang et al. (2004) Science 303: 371: Sears et al. (2001) Science 291: 2344; Wacker et al. (2002) Science 298: 1790; Davis et al. (2002) Chem. Rev. 102: 579; Hang et al. (2001) Acc. Chem. Res 34: 727. The antibodies (for example of the IgG isotype, e.g. IgG1) as herein described may comprise a defined number (e.g. 7 or less, for example 5 or less, such as two or a single) of glycoform(s).

The antibodies may or may not be coupled to a non-proteinaceous polymer such as polyethylene glycol (PEG), polypropylene glycol or polyoxyalkylene. Conjugation of proteins to PEG is an established technique for increasing half-life of proteins, as well as reducing antigenicity and immunogenicity of proteins. The use of PEGylation with different molecular weights and styles (linear or branched) has been investigated with intact antibodies as well as Fab' fragments, see Koumenis et al. (2000) int. J. Pharmaceut. 198: 83-95.

Production Methods

Antigen binding proteins may be produced in transgenic organisms such as goats (see Pollock et al. (1999) J. Immunol. Methods 231: 147-157), chickens (see Morrow (2000) Genet. Eng. News 20: 1-55, mice (see Pollock et al.) or plants (see Doran (2000) Curr. Opinion Biotechnol. 11: 199-204; Ma (1998) Nat. Med. 4: 601-606; Baez et al. (2000) BioPharm 13: 50-54; Stoger et al. (2000) Plant Mol. Biol. 42: 583-590).

Antigen binding proteins may also be produced by chemical synthesis. However, antigen binding proteins are typically produced using recombinant cell culturing technology well known to those skilled in the art. A polynucleotide encoding the antigen binding protein is isolated and inserted into a replicable vector such as a plasmid for further cloning (amplification) or expression. One expression system is a glutamate synthetase system (such as sold by Lonza Biologics), particularly where the host cell is CHO or NS0. Polynucleotide encoding the antigen binding protein is readily isolated and sequenced using conventional procedures (e.g. oligonucleotide probes). Vectors that may be used include plasmid, virus, phage, transposons, minichromosomes of which plasmids are typically used. Generally such vectors further include a signal sequence, origin of replication, one or more marker genes, an enhancer element, a promoter and transcription termination sequences operably linked to the antigen binding protein polynucleotide so as to facilitate expression. Polynucleotide encoding the light and heavy chains may be inserted into separate vectors and introduced (for example by transformation, transfection, electroporation or transduction) into the same host cell concurrently or sequentially or, if desired both the heavy chain and light chain can be inserted into the same vector prior to said introduction.

Codon optimisation may be used with the intent that the total level of protein produced by the host cell is greater when transfected with the codon-optimised gene in comparison with the level when transfected with the wild-type sequence. Several methods have been published (Nakamura et al. (1996) Nucleic Acids Research 24: 214-215; WO98/34640; WO97/11086). Due to the redundancy of the genetic code, alternative polynucleotides to those disclosed herein (particularly those codon optimised for expression in a given host cell) may also encode the antigen binding proteins described herein. The codon usage of the antigen binding protein of this invention thereof can be modified to accommodate codon bias of the host cell such to augment transcript and/or product yield (eg Hoekema et al Mol Cell Biol 1987 7(8): 2914-24). The choice of codons may be based upon suitable compatibility with the host cell used for expression.

Signal Sequences

Antigen binding proteins may be produced as a fusion protein with a heterologous signal sequence having a specific cleavage site at the N-terminus of the mature protein. The signal sequence should be recognised and processed by the host cell. For prokaryotic host cells, the signal sequence may be for example an alkaline phosphatase, penicillinase, or heat stable enterotoxin II leaders. For yeast secretion the signal sequences may be for example a yeast invertase leader, a factor leader or acid phosphatase leaders see e.g. WO90/13646. In mammalian cell systems, viral secretory leaders such as herpes simplex gD signal and a native immunoglobulin signal sequence may be suitable. Typically the signal sequence is ligated in reading frame to DNA encoding the antigen binding protein.

Origin of Replication

Origin of replications are well known in the art with pBR322 suitable for most gram-negative bacteria, 2µ, plasmid for most yeast and various viral origins such as SV40, polyoma, adenovirus, VSV or BPV for most mammalian cells. Generally the origin of replication component is not needed for mammalian expression vectors but the SV40 may be used since it contains the early promoter.

Selection Marker

Typical selection genes encode proteins that (a) confer resistance to antibiotics or other toxins e.g. ampicillin, neomycin, methotrexate or tetracycline or (b) complement auxiotrophic deficiencies or supply nutrients not available in the complex media or (c) combinations of both. The selection scheme may involve arresting growth of the host cell. Cells, which have been successfully transformed with the genes encoding the antigen binding protein, survive due to e.g. drug resistance conferred by the co-delivered selection marker. One example is the DHFR selection marker wherein transformants are cultured in the presence of methotrexate. Cells can be cultured in the presence of increasing amounts of methotrexate to amplify the copy number of the exogenous gene of interest. CHO cells are a particularly useful cell line for the DHFR selection. A further example is the glutamate synthetase expression system (Lonza Biologics). An example of a selection gene for use in yeast is the trp1 gene, see Stinchcomb et al. (1979) Nature 282: 38.

Promoters

Suitable promoters for expressing antigen binding proteins are operably linked to DNA/polynucleotide encoding the antigen binding protein. Promoters for prokaryotic hosts include phoA promoter, beta-lactamase and lactose promoter systems, alkaline phosphatase, tryptophan and hybrid promoters such as Tac. Promoters suitable for expression in yeast cells include 3-phosphoglycerate kinase or other glycolytic enzymes e.g. enolase, glyceralderhyde 3 phosphate dehydrogenase, hexokinase, pyruvate decarboxylase, phosphofructokinase, glucose 6 phosphate isomerase, 3-phosphoglycerate mutase and glucokinase. Inducible yeast promoters include alcohol dehydrogenase 2, isocytochrome C, acid phosphatase, metallothionein and enzymes responsible for nitrogen metabolism or maltose/galactose utilization.

Promoters for expression in mammalian cell systems include viral promoters such as polyoma, fowlpox and adenoviruses (e.g. adenovirus 2), bovine papilloma virus, avian sarcoma virus, cytomegalovirus (in particular the immediate early gene promoter), retrovirus, hepatitis B virus, actin, rous sarcoma virus (RSV) promoter and the early or late Simian virus 40. Of course the choice of promoter is based upon suitable compatibility with the host cell used for expression. A first plasmid may comprise a RSV and/or SV40 and/or CMV promoter, DNA encoding light chain variable region ($V_L$), κC region together with neomycin and ampicillin resistance selection markers and a second plasmid comprising a RSV or SV40 promoter, DNA encoding the heavy chain variable region ($V_H$), DNA encoding the γ1 constant region, DHFR and ampicillin resistance markers.

Enhancer Element

Where appropriate, e.g. for expression in higher eukaryotes, an enhancer element operably linked to the promoter element in a vector may be used. Mammalian enhancer sequences include enhancer elements from globin, elastase, albumin, fetoprotein and insulin. Alternatively, one may use an enhancer element from a eukaroytic cell virus such as SV40 enhancer (at bp100-270), cytomegalovirus early promoter enhancer, polyma enhancer, baculoviral enhancer or murine IgG2a locus (see WO04/009823). The enhancer may be located on the vector at a site upstream to the promoter. Alternatively, the enhancer may be located elsewhere, for example within the untranslated region or downstream of the polyadenylation signal. The choice and positioning of enhancer may be based upon suitable compatibility with the host cell used for expression.

Polyadenylation/Termination

In eukaryotic systems, polyadenylation signals are operably linked to DNA/polynucleotide encoding the antigen binding protein. Such signals are typically placed 3' of the open reading frame. In mammalian systems, non-limiting examples include signals derived from growth hormones, elongation factor-1 alpha and viral (eg SV40) genes or retroviral long terminal repeats. In yeast systems non-limiting examples of polydenylation/termination signals include those derived from the phosphoglycerate kinase (PGK) and the alcohol dehydrogenase 1 (ADH) genes. In prokaryotic system polyadenylation signals are typically not required and it is instead usual to employ shorter and more defined terminator sequences. The choice of polyadenylation/termination sequences may be based upon suitable compatibility with the host cell used for expression.

Other Methods/Elements for Enhanced Yields

In addition to the above, other features that can be employed to enhance yields include chromatin remodelling elements, introns and host-cell specific codon modification.

Host Cells

Suitable host cells for cloning or expressing vectors encoding antigen binding proteins are prokaroytic, yeast or higher eukaryotic cells. Suitable prokaryotic cells include eubacteria e.g. enterobacteriaceae such as *Escherichia* e.g. *E. coli* (for example ATCC 31,446; 31,537; 27,325), *Enterobacter, Erwinia, Klebsiella Proteus, Salmonella* e.g. *Salmonella typhimurium, Serratia* e.g. *Serratia marcescans* and *Shigella* as well as *Bacilli* such as *B. subtilis* and *B. licheniformis* (see DD 266 710), *Pseudomonas* such as *P. aeruginosa* and *Streptomyces*. Of the yeast host cells, *Saccharomyces cerevisiae, Schizosaccharomyces pombe, Kluyveromyces* (e.g. ATCC 16,045; 12,424; 24178; 56,500), yarrowia (EP402, 226), *Pichia pastoris* (EP 183 070, see also Peng et al. (2004) J. Biotechnol. 108: 185-192), *Candida, Trichoderma reesia* (EP 244 234), Penicillin, *Tolypocladium* and *Aspergillus* hosts such as *A. nidulans* and *A. niger* are also contemplated.

Higher eukaryotic host cells include mammalian cells such as COS-1 (ATCC NO.CRL 1650) COS-7 (ATCC CRL 1651), human embryonic kidney line 293, baby hamster kidney cells (BHK) (ATCC CRL.1632), BHK570 (ATCC NO: CRL 10314), 293 (ATCC NO.CRL 1573), Chinese hamster ovary cells CHO (e.g. CHO-K1, ATCC NO: CCL 61, DHFR-CHO cell line such as DG44 (see Urlaub et al. (1986) Somatic Cell Mol. Genet. 12: 555-556), particularly those CHO cell lines adapted for suspension culture, mouse sertoli cells, monkey kidney cells, African green monkey kidney cells (ATCC CRL-1587), HELA cells, canine kidney cells (ATCC CCL 34), human lung cells (ATCC CCL 75), Hep G2 and myeloma or lymphoma cells e.g. NS0 (see U.S. Pat. No. 5,807,715), Sp2/0, Y0.

Such host cells may also be further engineered or adapted to modify quality, function and/or yield of the antigen binding protein. Non-limiting examples include expression of specific modifying (e.g. glycosylation) enzymes and protein folding chaperones.

Cell Culturing Methods

Host cells transformed with vectors encoding antigen binding proteins may be cultured by any method known to those skilled in the art. Host cells may be cultured in spinner flasks, roller bottles or hollow fibre systems but for large scale production that stirred tank reactors are used particularly for suspension cultures. The stirred tankers may be adapted for aeration using e.g. spargers, baffles or low shear impellers. For bubble columns and airlift reactors direct aeration with air or oxygen bubbles maybe used. Where the host cells are cultured in a serum free culture media, the media is supplemented with a cell protective agent such as pluronic F-68 to help prevent cell damage as a result of the aeration process. Depending on the host cell characteristics, either microcarriers maybe used as growth substrates for anchorage dependent cell lines or the cells maybe adapted to suspension culture (which is typical). The culturing of host cells, particularly invertebrate host cells may utilise a variety of operational modes such as fed-batch, repeated batch processing (see Drapeau et al. (1994) Cytotechnology 15: 103-109), extended batch process or perfusion culture. Although recombinantly transformed mammalian host cells may be cultured in serum-containing media such as fetal calf serum (FCS), for example such host cells are cultured in synthetic serum-free media such as disclosed in Keen et al. (1995) Cytotechnology 17: 153-163, or commercially available media such as ProCHO-CDM or UltraCHO™ (Cambrex N.J., USA), supplemented where necessary with an energy source such as glucose and synthetic growth factors such as recombinant insulin. The serum-free culturing of host cells may require that those cells are adapted to grow in serum free conditions. One adaptation approach is to culture such host cells in serum containing media and repeatedly exchange 80% of the culture medium for the serum-free media so that the host cells learn to adapt in serum free conditions (see e.g. Scharfenberg et al. (1995) in Animal Cell Technology: Developments towards the 21st century (Beuvery et al. eds, 619-623, Kluwer Academic publishers).

Antigen binding proteins secreted into the media may be recovered and purified using a variety of techniques to provide a degree of purification suitable for the intended use. For example the use of antigen binding proteins for the treatment of human patients typically mandates at least 95% purity, more typically 98% or 99% or greater purity (compared to the crude culture medium). Cell debris from the culture media is typically removed using centrifugation followed by a clarification step of the supernatant using e.g. microfiltration, ultrafiltration and/or depth filtration. A variety of other techniques such as dialysis and gel electrophoresis and chromatographic techniques such as hydroxyapatite (HA), affinity chromatography (optionally involving an affinity tagging system such as polyhistidine) and/or hydrophobic interaction chromatography (HIC, see U.S. Pat. No. 5,429,746) are available. The antibodies, following various clarification steps, can be captured using Protein A or G affinity chromatography. Further chromatography steps can follow such as ion exchange and/or HA chromatography, anion or cation exchange, size exclusion chromatography and ammonium sulphate precipitation. Various virus removal steps may also be employed (e.g. nano-filtration using e.g. a DV-20 filter). Following these various steps, a purified (for example a monoclonal) preparation comprising at least 75 mg/ml or greater, or 100 mg/ml or greater, of the antigen binding protein is provided. Such preparations are substantially free of aggregated forms of antigen binding proteins.

Bacterial systems may be used for the expression of antigen binding fragments. Such fragments can be localised intracellularly, within the periplasm or secreted extracellularly. Insoluble proteins can be extracted and refolded to form active proteins according to methods known to those skilled in the art, see Sanchez et al. (1999) J. Biotechnol. 72: 13-20; and Cupit et al. (1999) Lett Appl Microbiol 29: 273-277.

Pharmaceutical Compositions

The terms diseases, disorders and conditions are used interchangeably. Purified preparations of an antigen binding protein as described herein may be incorporated into pharmaceutical compositions for use in the treatment of the human diseases described herein. The pharmaceutical composition can be used in the treatment of diseases where IL-7 contributes to the disease or where inhibition/neutralisation of IL-7R-mediated signalling will be beneficial. The pharmaceutical composition comprises a therapeutically effective amount of the antigen binding protein described herein.

The pharmaceutical preparation may comprise an antigen binding protein in combination with a pharmaceutically acceptable carrier. The antigen binding protein may be administered alone, or as part of a pharmaceutical composition.

Typically such compositions comprise a pharmaceutically acceptable carrier as known and called for by acceptable pharmaceutical practice, see e.g. Remingtons Pharmaceutical Sciences, 16th edition (1980) Mack Publishing Co. Examples of such carriers include sterilised carriers such as saline, Ringers solution or dextrose solution, optionally buffered with suitable buffers to a pH within a range of 5 to 8.

Pharmaceutical compositions may be administered by injection or continuous infusion (e.g. intravenous, intraperitoneal, intradermal, subcutaneous, intramuscular or intraportal). Such compositions are suitably free of visible particulate matter. Pharmaceutical compositions may comprise between 1 mg to 10 g of antigen binding protein, for example between 5 mg and 1 g of antigen binding protein. Alternatively, the composition may comprise between 5 mg and 500 mg, for example between 5 mg and 50 mg.

Methods for the preparation of such pharmaceutical compositions are well known to those skilled in the art. Pharmaceutical compositions may comprise between 1 mg to 10 g of antigen binding protein in unit dosage form, optionally together with instructions for use. Pharmaceutical compositions may be lyophilised (freeze dried) for reconstitution prior to administration according to methods well known or apparent to those skilled in the art. Where antibodies have an IgG1 isotype, a chelator of copper, such as citrate (e.g. sodium citrate) or EDTA or histidine, may be added to the pharmaceutical composition to reduce the degree of copper-mediated degradation of antibodies of this isotype, see EP0612251. Pharmaceutical compositions may also comprise a solubiliser such as arginine base, a detergent/anti-aggregation agent such as polysorbate 80, and an inert gas such as nitrogen to replace vial headspace oxygen.

Effective doses and treatment regimes for administering the antigen binding protein are generally determined empirically and may be dependent on factors such as the age, weight and health status of the patient and disease or disorder to be treated. Such factors are within the purview of the attending physician. Guidance in selecting appropriate doses may be found in e.g. Smith et al (1977) Antibodies in human diagnosis and therapy, Raven Press, New York. Thus the antigen binding protein of the invention may be administered at a therapeutically effective amount.

The dosage of antigen binding protein administered to a subject is generally between 1 μg/kg to 150 mg/kg, between 0.1 mg/kg and 100 mg/kg, between 0.5 mg/kg and 50 mg/kg, between 1 and 25 mg/kg or between 1 and 10 mg/kg of the subject's body weight. For example, the dose may be 10 mg/kg, 30 mg/kg, or 60 mg/kg. The antigen binding protein may be administered parenterally, for example subcutaneously, intravenously or intramuscularly.

If desired, the effective daily dose of a therapeutic composition may be administered as two, three, four, five, six or more sub-doses administered separately at appropriate intervals, optionally, in unit dosage forms. For example, the dose may be administered subcutaneously, once every 14 or 28 days in the form of multiple sub-doses on each day of administration.

The administration of a dose may be by intravenous infusion, typically over a period of from 15 minutes to 24 hours, such as from 2 to 12 hours, or from 2 to 6 hours. This may result in reduced toxic side effects.

The administration of a dose may be repeated one or more times as necessary, for example, three times daily, once every day, once every 2 days, once a week, once a fortnight, once a month, once every 3 months, once every 6 months, or once every 12 months. The antigen binding proteins may be administered by maintenance therapy, for example once a week for a period of 6 months or more. The antigen binding proteins may be administered by intermittent therapy, for example for a period of 3 to 6 months and then no dose for 3 to 6 months, followed by administration of antigen binding proteins again for 3 to 6 months, and so on in a cycle.

The dosage may be determined or adjusted by measuring the amount of IL-17 in a biological sample. Other means of determining or adjusting dosage may be utilized, including but not limited to biologic markers ('biomarkers') of pharmacology, measures of muscle mass and/or function, safety, tolerability, and therapeutic response. The antigen binding protein can be administered in an amount and for a duration effective to down-regulate IL-7 mediated signalling activity in the subject.

The antigen binding protein may be administered to the subject in such a way as to target therapy to a particular site. For example, the antigen binding protein may be injected locally into muscle, for example skeletal muscle.

The antigen binding protein may be used in combination with one or more other therapeutically active agents, for example: immunomodulators such as interferon beta (IFNβ-1a or IFNβ-1b) and glatiramer acetate, immunosuppresants such as cyclophosphamide, methotrexate, azathioprine, cladribine, cyclosporine and mitoxantrone, other immune therapies such as intravenous immune globulin (IVIg), plasma replacement and sulphasalazine. The additional therapeutic may be administered as in a manner (dosage, timing, mechanism) as prescribed by a physician. In an embodiment, the additional therapeutic agent may be administered simultaneously or sequentially or separately from the antigen binding protein of the present invention. In an embodiment, the additional therapeutic agent and the antigen binding protein are administered such that their pharmacological effects on the patient overlap; in other words, they exert their biological effects on the patient at the same time.

When the antigen binding protein is used in combination with other therapeutically active agents, the individual components may be administered either together or separately, sequentially or simultaneously, in separate or combined pharmaceutical formulations, by any appropriate route. If administered separately or sequentially, the antigen binding protein and the therapeutically active agent(s) may be administered in any order.

The combinations referred to above may be presented for use in the form of a single pharmaceutical formulation comprising a combination as defined above optionally together with a pharmaceutically acceptable carrier or excipient.

When combined in the same formulation it will be appreciated that the components must be stable and compatible with each other and the other components of the formulation and may be formulated for administration. When formulated separately they may be provided in any convenient formulation, for example in such a manner as known for antigen binding proteins in the art.

When in combination with a second therapeutic agent active against the same disease, the dose of each component may differ from that when the antigen binding protein is used alone. Appropriate doses will be readily appreciated by those skilled in the art.

The antigen binding protein and the therapeutically active agent(s) may act synergistically. In other words, administering the antigen binding protein and the therapeutically active agent(s) in combination may have a greater effect on the disease, disorder, or condition described herein than the sum of the effect of each alone.

The pharmaceutical composition may comprise a kit of parts of the antigen binding protein together with other medicaments, optionally with instructions for use. For convenience, the kit may comprise the reagents in predetermined amounts with instructions for use.

The terms "individual", "subject" and "patient" are used herein interchangeably. The subject is typically a human. The subject may also be a mammal, such as a mouse, rat or primate (e.g. a marmoset or monkey). The subject can be a non-human animal. The antigen binding proteins may also have veterinary use. The subject to be treated may be a farm animal for example, a cow or bull, sheep, pig, ox, goat or horse or may be a domestic animal such as a dog or cat. The animal may be any age, or a mature adult animal.

Treatment may be therapeutic, prophylactic or preventative. The subject may be one who is in need thereof. Those in need of treatment may include individuals already suffering from a particular medical disease in addition to those who may develop the disease in the future.

Thus, the antigen binding protein described herein can be used for prophylactic or preventative treatment. In this case, the antigen binding protein described herein is administered to an individual in order to prevent or delay the onset of one or more aspects or symptoms of the disease. The subject can be asymptomatic. The subject may have a genetic predisposition to the disease. A prophylactically effective amount of the antigen binding protein is administered to such an individual. A prophylactically effective amount is an amount which prevents or delays the onset of one or more aspects or symptoms of a disease described herein.

The antigen binding protein described herein may also be used in methods of therapy. The term "therapy" encompasses alleviation, reduction, or prevention of at least one aspect or symptom of a disease. For example, the antigen binding protein described herein may be used to ameliorate or reduce one or more aspects or symptoms of a disease described herein.

The antigen binding protein described herein is used in an effective amount for therapeutic, prophylactic or preventative treatment. A therapeutically effective amount of the antigen binding protein described herein is an amount effective to ameliorate or reduce one or more aspects or symptoms of the disease. The antigen binding protein described herein may also be used to treat, prevent, or cure the disease described herein.

The antigen binding protein described herein may have a generally beneficial effect on the subject's health, for example it can increase the subject's expected longevity.

The antigen binding protein described herein need not affect a complete cure, or eradicate every symptom or manifestation of the disease to constitute a viable therapeutic treatment. As is recognised in the pertinent field, drugs employed as therapeutic agents may reduce the severity of a given disease state, but need not abolish every manifestation of the disease to be regarded as useful therapeutic agents. Similarly, a prophylactically administered treatment need not be completely effective in preventing the onset of a disease in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur (for example by delaying the onset of the disease) or worsen in a subject, is sufficient.

The antigen binding proteins of the present invention may be used in the therapy of multiple sclerosis and in other autoimmune or inflammatory diseases, particularly those in which pathogenic $T_H17$ cells are implicated. Such diseases are associated with high levels of IL-17 expression. Elevated levels of IL-17 have been reported in serum and CSF of MS patients (Matusevicius, D. et al.; Mult. Scler. 5, 101-104; 1999) and in the synovial fluid obtained from rheumatoid arthritis patients. IL-17 has also been implicated in psoriasis (Homey et al.; J. Immunol. 164(12):6621-32; 2000), while Hamzaoui et al reported high levels of IL-17 in Behcet's disease (Scand. J. Rhuematol.; 31:4, 205-210; 2002). Elevated IL-17 levels have also been observed in systemic lupus erythrematosus (SLE) (Wong et al.; Lupus 9(8):589-93; 2000).

Inhibition of IL-7 receptor mediated signalling may also be useful in the treatment of inflammatory (non-autoimmune) diseases in which elevated IL-17 has been implicated, such as asthma.

Accordingly, inflammatory and/or autoimmune diseases of the invention include inflammatory skin diseases including psoriasis and atopic dermatitis; systemic scleroderma and sclerosis; inflammatory bowel disease (IBD); Crohn's disease; ulcerative colitis; ischemic reperfusion disorders including surgical tissue reperfusion injury, myocardial ischemic conditions such as myocardial infarction, cardiac arrest, reperfusion after cardiac surgery and constriction after percutaneous transluminal coronary angioplasty, stroke, and abdominal aortic aneurysms; cerebral edema secondary to stroke; cranial trauma, hypovolemic shock; asphyxia; adult respiratory distress syndrome; acute-lung injury; Behcet's Disease; dermatomyositis; polymyositis; multiple sclerosis (MS); dermatitis; meningitis; encephalitis; uveitis; osteoarthritis; lupus nephritis; autoimmune diseases such as rheumatoid arthritis (RA), Sjorgen's syndrome, vasculitis; diseases involving leukocyte diapedesis; central nervous system (CNS) inflammatory disorder, multiple organ injury syndrome secondary to septicaemia or trauma; alcoholic hepatitis; bacterial pneumonia; antigen-antibody complex mediated diseases including glomerulonephritis; sepsis; sarcoidosis; immunopathologic responses to tissue/organ transplantation; inflammations of the lung, including pleurisy, alveolitis, vasculitis, pneumonia, chronic bronchitis, bronchiectasis, diffuse panbronchiolitis, hypersensitivity pneumonitis, idiopathic pulmonary fibrosis (IPF), and cystic fibrosis; psoriatic arthritis; neuromyelitis optica, Guillain-Barre syndrome (GBS), COPD, type 1 diabetes, etc.

In particular, the antagonists of the present invention may be useful in the therapy of multiple sclerosis, in all its forms, including neuromyelitis optica. Treatment with an antagonist of the present invention is predicted to be most efficacious when administered in the context of active inflammatory disease, i.e. when used in the treatment of clinically isolated syndrome or relapsing forms of MS. These stages of disease can be defined clinically and/or by imaging criteria such as gadolinium enhancement or other more sensitive techniques, and/or other as yet undefined biomarkers of active disease. Particularly, the antagonists of the invention can be used to treat RRMS (via intravenous, subcutaneous, oral or intramuscular delivery) when the patients are entering or are in relapse. In an embodiment, the antagonist of the invention is administered to the patient at the onset of relapse, or within 1 hr, 2 hrs, 3 hrs, 6 hrs, 12 hrs, 24 hrs, 2 days, 3 days, 4 days, 5 days, 6 days, 7 days, 8 days, 9 days or 10 days from the onset of relapse.

The antigen binding proteins of the invention are capable of binding to CD127. In an embodiment the antigen binding proteins of the invention are capable of antagonising the biological effect of the IL-7 receptor. In an embodiment, the antigen binding proteins are capable of antagonising at least one of: IL-7 receptor mediated $T_H17$ expansion, and IL-7 receptor mediated $T_H17$ survival.

The term inhibit, antagonise and neutralise are used herein synonymously. No term is intended to suggest the requirement of total neutralisation; partial neutralisation—corresponding to a reduction but not complete abolition of the biological effect—is also contemplated.

IL-7 receptor mediated $T_H17$ expansion and/or survival can be observed at a cellular level by an increase or maintenance of $T_H17$ cell count, or by an increase in the ratio of $T_H17$ cell numbers compared to the numbers of other CD4+ T cells, or more specifically by an increase in the ratio of $T_H17:T_H1$ cells, the ratio of $T_H17:T_{reg}$ cells, the ratio of $(T_H17 \text{ plus } T_H1):T_{reg}$ cells, and/or the ratio of $T_H17:(T_H1 \text{ plus } T_{reg})$ cells.

At a molecular level, $T_H17$ expansion and/or survival can be observed by an increase in IL-17 production by a population of CD4+ T cells (or by a population of $T_H17$ cells). In an embodiment, therefore, the antigen binding proteins of the invention reduce IL-17 production by a population of CD4+ T cells. IL-7 receptor mediated $T_H17$ expansion and survival can also be observed by an increase in IFN-γ production by a population of CD4+ T cells (or by a population of $T_H17$ cells). Thus, in an embodiment, the antigen binding proteins of the invention antagonise (reduce) IFN-γ production by a population of CD4+ T cells. At a molecular level, the antigen binding proteins of the invention may inhibit IL-7 receptor mediated STAT-5 phosphorylation.

At the molecular level, one can observe and measure the blocking effect of the antigen binding proteins of the invention by assays such as IL-7-induced P-STAT5 or Bcl-2. At the cellular level, one can observe and measure the blocking effect by assays such as Th17 secretion of IL-17 or IFNγ. Exemplary assays are described in PCT application number PCT/US2009/053136 (WO2010/017468).

In an exemplary pSTAT-5 assay, PBMCs are stimulated with IL-7 in the presence and absence of a test agent. Cells are subsequently assessed quantitatively for the level of pSTAT-5, e.g. by staining for pSTAT-5 (e.g. with a labelled anti-pSTAT-5 antibody, such as Alexa Fluor® 647 Mouse Anti-Stat5 (pY694, BD [#612599])) followed by fluorescence activated cell sorting. The levels of phosphorylated STAT-5 could also be determined by ELISA. Those agents which reduce the level of phosphorylated STAT-5 may be potential therapeutic candidates for autoimmune disease.

The antagonist may be capable of reducing levels of phosphorylated STAT-5 by at least 20%, 50%, 75%, 80%, 85%, 90%, 95% or 100% when compared to STAT-5 levels in the absence of the antagonist, or when compared to a negative control, or untreated cells. The antagonist may have an $IC_{50}$ of 50 µg/ml, 25 µg/ml or less, 10 µg/ml or less, 5 µg/ml or less, or 2 µg/ml or less. In an embodiment, the antagonist has an $IC_{50}$ of less than or equal to 1 µg/ml, less than or equal to 0.75 µg/ml, less than or equal to 0.5 µg/ml, less than or equal to 0.25 µg/ml, or less than or equal to 0.1 µg/ml.

The antagonists of the invention are particularly effective in inhibiting the expansion of $T_H17$ cells. Expansion of $T_H17$ cells can be determined in a $T_H17$ expansion assay, which comprises stimulating a population of naïve T cells to expand in the presence and absence of a test agent, followed by stimulating the cells to produce IL-17 and assessing the level of IL-17 produced by the cells in the presence and absence of the test agent.

In an exemplary assay, human CD4+ T cells are differentiated into $T_H17$ by stimulation with T cell receptor activation in the presence of IL-1, IL-6, and IL-23. After 5 days of differentiation, CCR6+ cells are sorted out to produce an enriched $T_H17$ population. This population is then stimulated with human IL-7 and the increase in IL-17 and IFN-γ in the supernatant are determined. The ability of a test agent, such as an antigen binding fragment of the present invention to block the interaction between the IL-7 and CD127 can be determined as the presence of an antagonist of this interaction during the incubation period should prevent the expansion of the $T_H17$ cells leading to the reduction of IL-17 and IFN-γ production.

The antigen binding proteins of the invention may be capable of from 20% or more inhibition of IL-17 secretion in such an assay, versus a negative control. More typically, the antigen binding protein is capable of from 50%, from 75%, from 85% or from 90% or more inhibition of IL-17 secretion versus the control. The antigen binding fragment may, in some embodiments, exhibit an $IC_{50}$ of less than or equal to 50 µg/ml in the assay. In other embodiments, the $IC_{50}$ may be less than or equal to 20 µg/ml, 10 µg/ml or 5 µg/ml.

Thus, in another aspect, the invention provides a method for the treatment of an autoimmune disease or inflammatory disorder, comprising administering to a patient an antigen binding protein of the invention in an amount sufficient to reduce the $T_H17$ cell count in the patient.

In another aspect, the invention provides a method for the treatment of an autoimmune disease in a human subject, comprising administering to the subject an antigen binding protein in an amount sufficient to reduce IL-7 receptor mediated STAT-5 phosphorylation.

In another aspect, the present invention provides a method for treating multiple sclerosis in a patient comprising administering an antigen binding protein of the invention to the patient, wherein the patient is suffering from relapsing remitting multiple sclerosis.

In another aspect, the invention provides a method of treating an autoimmune or inflammatory disease in a human subject, comprising administering to the subject an antigen binding protein of the invention to the patient in an amount effective to reduce the ratio of $T_H17$ cells relative to $T_H1$ cells.

In another aspect, the invention provides a method of treating an autoimmune or inflammatory disease in a human subject, comprising administering to the subject an antigen binding protein of the invention to the patient in an amount effective to reduce the ratio of $T_H$ cells relative to (Foxp3+) $T_{reg}$ cells.

Diagnostic Methods of Use

The antigen binding proteins described herein may be used to detect CD127 in a biological sample in vitro or in vivo for diagnostic purposes. For example, the anti-CD127 antigen binding proteins can be used to detect CD127 in cultured cells, in a tissue or in serum. The tissue may have been first removed (for example a biopsy) from a human or animal body. Conventional immunoassays may be employed, including ELISA, Western blot, immunohistochemistry, or immunoprecipitation.

The antigen binding proteins may be provided in a diagnostic kit comprising one or more antigen binding proteins, a detectable label, and instructions for use of the kit. For convenience, the kit may comprise the reagents in predetermined amounts with instructions for use.

Gene Therapy

Nucleic acid molecules encoding the antigen binding proteins described herein may be administered to a subject in need thereof. The nucleic acid molecule may express the CDRs in an appropriate scaffold or domain, the variable domain, or the full length antibody. The nucleic acid molecule may be comprised in a vector which allows for expression in a human or animal cell. The nucleic acid molecule or vector may be formulated for administration with a pharmaceutically acceptable excipient and/or one or more therapeutically active agents as discussed above.

EXAMPLES 1.0 Humanization of 1A11

1.1 1A11 Cloning of the Hybridoma Variable Regions

Total RNA was prepared from a cell pellets of the 1A11 hybridomas and RT-PCR performed to generate cDNA of the variable regions. The amplified variable regions for heavy and light chain of each hybridoma were cloned into a pCR2.1 cloning vector. Sequence for the heavy and light variable regions of each hybridoma was obtained. Sequence analysis predicted the peptide sequences as follows (with the complementarity determining regions highlighted):

A) 1A11 VH
EVQLQQSGPELLKPGASMKISCKASGYSFTGYTMNWVKQSHGKNLEWIGL

INPYNGVTSYNQKFKGKATLTVAKSSSTAYMELLSLTSEDSAVYYCARGD

GNYWYFDVWGAGTTVTVSS (SEQ ID NO: 8)

B) 1A11 VL
EIVLTQSPAITAASLGQKVTITCSASSSVTYMHWYQQKSGTSPKPWIYEI

SKLASGVPVRFSGSGSGTSYSLTISSMEAEDAAIYYCQEWNYPYTFGGGT

KLEIK (SEQ ID NO: 9)

A recombinant chimeric form of the antibody was made by fusing the variable heavy and light regions to human IgG1 Fc and kappa constant regions respectively.

1.2 1A11 Heavy Chain Humanization Strategy

Following a BLAST analysis of the human V gene germline databases, human germline IGHV1_2 which had 64% identity (including CDRs) with the mouse 1A11 variable heavy chain sequence was selected as the preferred acceptor framework for humanisation. The germline V region was combined in silico with a suitable FR4, in this case the JH6 minigene (Kabat Vol.II) based on sequence similarity. The first six residues of the JH6 minigene residues preceding the WGQG motif fall within the CDR3 region which is replaced by the incoming CDR from the donor antibody. Eight humanised heavy chain variants were generated on the basis of sequence comparison and possible impact on antibody function. Construct H0 was a straight graft of mouse CDRs from 1A11 (using the Kabat definition) into the human acceptor framework selected above. Constructs H1 through H3 are based on H0; each incorporates one additional framework mutation which was different in each construct; positions 71, 66 and 69 respectively. H4 through H7 constructs incorporate two or three of the above back mutations optionally with further back mutations at positions 72 and 73.

1A11 Heavy Chain Humanization Rationale for framework IGHV1-2

| | Kabat position | | | | |
|---|---|---|---|---|---|
| | 66 | 69 | 71 | 72 | 73 |
| VH1A11 | K | L | V | A | K |
| IGHV1_2 | R | M | R | D | T |
| 1A11H0 | R | M | R | D | T |
| 1A11H1 | R | M | V | D | T |
| 1A11H2 | K | M | R | D | T |
| 1A11H3 | R | L | R | D | T |
| 1A11H4 | K | M | V | D | T |
| 1A11H5 | K | L | V | D | T |
| 1A11H6 | K | L | V | D | K |
| 1A11H7 | K | L | V | A | K |

1.4 1A11 Light Chain Humanization Strategy

Following a BLAST analysis of the human V gene germline databases, human germline IGKV3_11 which had 53% identity (including CDRs) with the mouse 1A11 variable light chain sequence was selected as the preferred acceptor framework for humanisation. The germline V region was combined in silico with a suitable FR4, in this case the J-region kappa 4 minigene (Kabat Vol.II) based on sequence similarity. The first three residues of the JK-4 minigene residues fall within the CDR3 region which is replaced by the incoming CDR from the donor antibody. Ten humanised light chain variants were generated on the basis of sequence comparison and possible impact on antibody function. Construct L0 was a straight graft of mouse CDRs from 1A11 (using the Kabat definition) into the human acceptor framework selected above. Constructs L1, L2, L4 are based on L0, each incorporates one additional framework mutation which were different in each construct; positions 47, 71 and 46 respectively. Construct L3 incorporates both of the above back mutations 47 and 71. Construct L5 incorporates three of the above back mutations 47 and 71 and 46. Construct L6 through L9 are based on L5, each incorporates one, two, three and four additional framework mutations which were different in each construct; positions 58, 45, 70 and 60 respectively.

1A11 Light Chain Humanization Rationale for framework IGKV3-11

| | Kabat position | | | | | | |
|---|---|---|---|---|---|---|---|
| | 45 | 46 | 47 | 58 | 60 | 70 | 71 |
| Vk1A11 | K | P | W | V | V | S | Y |
| IGkV3_11 | R | L | L | I | A | D | F |
| 1A11L0 | R | L | L | I | A | D | F |
| 1A11L1 | R | L | W | I | A | D | F |
| 1A11L2 | R | L | L | I | A | D | Y |
| 1A11L3 | R | L | W | I | A | D | Y |
| 1A11L4 | R | P | L | I | A | D | F |
| 1A11L5 | R | P | W | I | A | D | F |
| 1A11L6 | R | P | W | V | A | D | Y |
| 1A11L7 | K | P | W | V | A | D | Y |
| 1A11L8 | K | P | W | V | A | S | Y |
| 1A11L9 | K | P | W | V | V | S | Y |

2.0 Humanization of 6A3

2.1 6A3 Heavy Chain Humanisation Strategy

Following a BLAST analysis of the human V gene germline databases, human germline IGHV4_61 which had 71% identity (including CDRs) with the mouse 6A3 variable heavy chain sequence and human germline IGHV3_33 which had 51% identity (which has been previously shown to express well with IGKV1_39) were selected as the preferred acceptor frameworks for humanisation. The germline V region was combined in silico with a suitable FR4, in this case the JH6 minigene (Kabat Vol.II) based on sequence similarity. The first two residues of the JH6 minigene residues preceding the WGQG motif fall within the CDR3 region which is replaced by the incoming CDR from the donor antibody. Ten humanised heavy chain variants with framework IGHV4_61 and twelve humanised heavy chain variants with framework IGHV3_33 were generated on the basis of sequence comparison and possible impact on antibody function. Construct H0 was a straight graft of mouse CDRs from 6A3 (using the Kabat definition) into the human acceptor framework selected above. H1 through H5 constructs with framework IGHV4_61 are based on H0, each incorporates one additional framework mutation which was different in each construct; positions 71, 27, 30, 67 and 48 respectively. H6 through H9 constructs incorporate two, three, four or five of the above back mutations. H1 through H11 constructs with framework IGHV3-33 are based on H0, each incorporates one additional framework mutation which was different in each construct; positions 27, 30, 28, 29, 67, 73, 78, 49, 68, 24 and 48 respectively.

6A3 Heavy Chain Humanization Rationale for framework IGHV4 61

| | Kabat position | | | | |
|---|---|---|---|---|---|
| | 27 | 30 | 48 | 67 | 71 |
| VH6A3 | Y | T | M | I | R |
| IGHV4_61 | G | S | I | V | V |
| 6A3H0 | G | S | I | V | V |
| 6A3H1 | G | S | I | V | R |
| 6A3H2 | Y | S | I | V | V |
| 6A3H3 | G | T | I | V | V |
| 6A3H4 | G | S | I | I | V |
| 6A3H5 | G | S | M | V | V |
| 6A3H6 | Y | S | I | V | R |
| 6A3H7 | Y | T | I | V | R |
| 6A3H8 | Y | T | I | I | R |
| 6A3H9 | Y | T | M | I | R |

6A3 Heavy Chain Humanization Rationale for framework IGHV3_33

| | Kabat position | | | | | | | | | |
|---|---|---|---|---|---|---|---|---|---|---|
| | 27 | 28 | 29 | 30 | 48 | 49 | 67 | 68 | 73 | 78 |
| VH6A3 | Y | S | I | T | M | G | I | S | T | F |
| IGHV3_33 | F | T | F | S | V | A | F | T | N | L |
| 6A3H0 | F | T | F | S | V | A | F | T | N | L |
| 6A3H1 | Y | T | F | S | V | A | F | T | N | L |
| 6A3H2 | F | T | F | T | V | A | F | T | N | L |
| 6A3H3 | F | S | F | S | V | A | F | T | N | L |
| 6A3H4 | F | T | I | S | V | A | F | T | N | L |
| 6A3H5 | F | T | F | S | V | A | I | T | N | L |
| 6A3H6 | F | T | F | S | V | A | F | T | T | L |
| 6A3H7 | F | T | F | S | V | A | F | T | N | F |
| 6A3H8 | F | T | F | S | V | G | F | T | N | L |
| 6A3H9 | F | T | F | S | M | A | F | S | N | L |

2.4 6A3 Light Chain Humanisation Strategy

Following a BLAST analysis of the human V gene germline databases, human germline IGKV1_39 which had 72% identity (including CDRs) with the mouse 6A3 variable light chain sequence was selected as the preferred acceptor framework for humanisation. The germline V region was combined in silico with a suitable FR4, in this case the J-region kappa 2 minigene (Kabat Vol.II) based on sequence similarity. The first two residues of the JK-2 minigene residues fall within the CDR3 region and are identical to the last two residues in the mouse 6A3 light chain CDR3. Five humanised light chain variants were generated on the basis of sequence comparison and possible impact on antibody function. Construct L0 was a straight graft of mouse CDRs from 6A3 (using the Kabat definition) into the human acceptor framework selected above. Constructs L1, L2 are based on L0, each incorporates one additional framework mutation which were different in each construct; positions 45, 70 respectively. Construct L3 incorporates both of the above back mutations.

6A3 Light Chain Humanization Rationale for framework IGKV1_39

| | Kabat position | |
|---|---|---|
| | 45 | 70 |
| Vk6A3 | Q | K |
| IGkV1_39 | K | D |
| 6A3L0 | K | D |
| 6A3L1 | Q | D |
| 6A3L2 | K | K |
| 6A3L3 | Q | K |

Five humanised light chain variants were generated on the basis of sequence comparison and possible impact on antibody function. Construct L0 was a straight graft of mouse CDRs from 6A3 (using the Kabat definition) into the human acceptor framework selected above. Constructs L1, L2 are based on L0, each incorporates one additional framework mutation which were different in each construct; positions 45, 70 respectively. Construct L3 incorporates both of the above back mutations; Construct L27 incorporates more mutations include T4L, A31Y, D70M, V85T, T94Y, Q100G, L104V (SEQ ID NO:138).

TABLE 3

6A3 variable light humanised variants

| Humanised VL | Template | Backmutations (Kabat#) |
|---|---|---|
| L0 | Straight graft of 6A3VLCDRs onto IGKV1-39 + JK-2 minigene | None |
| L1 | L0 | K45Q |
| L2 | L0 | D70K |
| L3 | L1 | K45Q, D70K |
| L27 | L0 | T4L, A31Y, D70M, V85T, T94Y, Q100G, L104V |

2.5 Construction of Fc Disabled Variable Heavy Chain

Two amino acid substitutions, L237A and G239A were made to the 1A11 H3 construct. These modifications render the molecule less able to recruit immune effector cells or complement. The resulting VH construct is identified as 1A11 H3-Fc, and has a sequence as shown in SEQ ID NO:118 (encoded by a polynucleotide having the sequence of SEQ ID NO:119). The antibody comprising 1A11 H3-Fc and the 1A11.L4 light chain (1A11 H3L4Fc) was further analysed as described in Example 4 below.

2.6 Affinity Maturation of 1A11 H3L4

2.6.1 Construction of Recombinant Anti-IL7R 1A11 H3L4 CDRH3 Variants

A number of variants of the humanised anti-IL7R monoclonal antibody 1A11 H3L4 were produced. These all differed by only one amino acid substitution in the CDRH3 region of the heavy chain of the antibody having the heavy chain amino acid sequence set out in SEQ ID NO:114 (H3), and the light chain amino acid sequence set out in SEQ ID NO:115 (L4).

Humanised CDRH3 variants of 1A11 H3L4 within the pLEFD mammalian expression vector were generated using site-directed mutagenesis.

2.6.2 Small Scale Antibody Expression in HEK 293 6E Cells pLEFN and pLEFD plasmids encoding the light and heavy chains of 1A11 H3L4 and CDRH3 variants respectively were transiently co-transfected into HEK 293 6E cells at 96-well scale (500 μl expression volume) using 293fectin (Invitrogen, 12347019). Supernatants were harvested by centrifugation for 10 minutes at 1500 rpm. The supernatants containing antibody were then filtered using a 0.45 μm filtration plate. Antibodies were assessed directly from the tissue culture supernatant.

2.6.3 Proteon Analysis of Anti-IL7R 1A11 H3L4 CDRH3 Variants

The initial screen to determine the binding affinity of the CDRH3 antibody variants (which were derived from small scale antibody expressions in HEK 293 6E cells and assessed directly from the tissue culture supernatant, as described in Example 2.6.2) was carried out on the ProteOn XPR36 (Biorad). The method was as follows; Protein A was immobilised on a GLC chip by primary amine coupling, CDRH3 mutant antibodies were then captured on this surface and IL7R passed over at 256, 64, 16, 4, 1 nM with a 0 nM injection (i.e. buffer alone) used to double reference the binding curves. 50 mM NaOH was used to regenerate the capture surface, removing the bound CDRH3 mutant antibodies ready for another cycle of capture and analyte injection. The data was fitted to the 1:1 model using the analysis software inherent to the machine. Binding analysis for mutant antibodies was carried out directly from tissue culture supernatants.

The screen identified several antibodies that appeared to have better kinetic profiles than the parental molecule (1A11 H3L4). The data obtained from this analysis is shown in 4.2.3, showing that several CDRH3 mutations at the N98 and F100b residues appeared to improve the binding affinity to IL7R. From this data set, six molecules were selected for further analysis (Example 2.6.4).

2.6.4 Larger Scale Antibody Expression in HEK 293 6E Cells

The data highlighted that several CDRH3 mutations at the N98 and F100b residues appeared to improve the binding affinity to IL7R (data shown in 4.2.3). Therefore, purified antibody was produced for these six CDRH3 variants. Constructs encoding the heavy and light chain of 1A11 H3L4 CDRH3 variants were sub-cloned from the pLEFD and pLEFN plasmids into the pTT vector for optimal large scale HEK 293 6E expression. Plasmids were transiently co-transfected into 50-100 ml of HEK 293 6E (plasmid details summarised in Table 7) using 293fectin (Invitrogen, 12347019). A tryptone feed was added to the cell culture after 24 hours and the cells were harvested after a further 72 hours. Antibody was then affinity purified using immobilised Protein A columns and quantified by reading the absorbance at 280 nm.

3.0 Construction of Humanised Vectors

The DNA sequences of the humanised variable regions were sequence optimised using the LETO 1.0 software (Entelechon GmbH) and synthesised de novo by build up of overlapping oligonucleotide and PCR amplification. Primers included restriction sites for cloning into mammalian expression vectors and human immunoglobulin signal sequences for secretion. The humanised variable heavy regions were cloned into mammalian expression vectors containing the human gamma 1 constant region using Age1/Kas1. In parallel, the humanised variable light regions were cloned into mammalian expression vectors containing the human kappa constant region using HindIII and BsiWI.

4.0 Characterisation of Humanised Antibodies

4.1 Determination of Binding Kinetics of 1A11 and 6A3 Constructs: BIACORE™ 3000

The binding kinetics of the anti-CD127 antibodies for human CD127 ECD was assessed using a BIACORE™ 3000 device (GE Healthcare). Humanised 6A3 or 1A11 constructs were captured on a CM5 biosensor chip which was already immobilized BIACORE™ (GE Healthcare cat# BR-1008-39) anti-human IgG (Fc specific) monoclonal antibody using supplied coupling buffer. A range of human CD127 ECD concentrations (512, 256, 128, 64, 32, 16 nM) were injected for 240 s at a flow rate of 30 ul/min.
1) Capture MAb of interest
2) Association of Analyte to captured MAb
3) Dissociation of Analyte (buffer)
4) Regenerate with BIACORE™ optimized buffer. Removes all but covalently coupled anti-H Ab. BIACORE™ Kinetic run Cycles: buffer, 512, 256, 128, 64, 32, 16 nM IL7R ECD; buffer cycle used for double referencing.

The antibody surfaces were regenerated with 3 M $MgCl_2$. Kinetics were determined by global fitting of data to the 1:1 Langmuir model using BIAEVALUATION software. Results are shown in Example 4.2.1 (1A11) and 4.2.2 (6A3).

4.1.1 Determination of Binding Kinetics of Selected 1A11 H3L4 CDRH3 Variants BIACORE™ analysis was used to determine the binding affinity of the purified CDRH3 mutant antibodies (which were derived from larger scale antibody expressions in HEK 293 6E cells, as described in Example 2.6.4).

4.1.1.1 Method 1: BIACORE™ T100

An anti-human IgG (GE Healthcare/-BIACORE™ BR-1008-39) was immobilised on a CM3 chip by primary amine coupling to a level of ~1300 resonance units (RU's), CDRH3 mutant antibodies were then captured on this, all the antibodies were captured to a similar level (44-56 RU's) and IL-7R passed over at 256, 64, 16, 4, 1 nM with a 0 nM injection (i.e. buffer alone) used to double reference the binding curves, regeneration of this surface was achieved using 3M $MgCl_2$. The binding data was fitted to the 1:1 model inherent to the BIACORE™ T100 analysis software. The run was carried out using HBS-EP as running buffer and carried out at 25° C. on the BIACORE™ T100. Results are shown in 4.2.4.

4.1.1.2: Method 2: BIACORE™ 3000

An anti-human IgG (GE Healthcare/BIACORE™ BR-1008-39) was immobilised on a CM5 chip by primary amine coupling to a level of ~5400 resonance units (RU's), CDRH3 mutant antibodies were then captured on this surface, all the antibodies were captured to a similar level (175-205 RU's) and IL7R passed over at 64, 16, 4, 1 nM with a 0 nM injection (i.e. buffer alone) used to double reference the binding curves, regeneration of this surface was achieved using 3M $MgCl_2$. The binding data was fitted to the 1:1 model inherent to the BIACORE™ 3000 analysis software. The run was carried out using HBS-EP as running buffer and carried out at 25° C. on the BIACORE™ 3000. Results are shown in 4.2.5.

4.1.2 Determination of Species Cross-Reactivity of 1A11 H3L4 in Cynomolgus and Marmoset The binding kinetics of 1A11 H3L4 for Cynomolgus and Marmoset CD127 ECD was assessed using a BIACORE™ 3000. 1A11 H3L4 was captured on a CM5 biosensor chip which was already immobilized BIACORE™ (GE Healthcare cat# BR-1008-39) anti-human IgG (Fc specific) monoclonal antibody. The antibody surfaces were regenerated with 3 M $MgCl_2$. Kinetics was determined by global fitting of data to the 1:1 Langmuir model using BIAEVALUATION software. Results are shown in 4.3.

4.1.3 IL7 Receptor Inhibition Assay

BIACORE™ analysis was also used to demonstrate that the purified CDRH3 mutant antibodies (which were derived from larger scale antibody expressions in HEK 293 6E cells, as described in Example 2.6.4) were able to inhibit the interaction between IL7 and IL7R.

IL7 (R&D Systems) was immobilised on a CM5 chip by primary amine coupling; the surface was conditioned with 10 mM glycine, pH3.0 to provide a stable surface for the neutralisation assay. IL7R at 64 nM was incubated with the test antibodies at concentrations of 256 nM, 128 nM, 64 nM, 16 nM, 8 nM, 4 nM, 2 nM and 1 nM in run 1 and of 256 nM, 128 nM, 64 nM, 16 nM, 8 nM, 4 nM, 2 nM, 1 nM, 0.5 nM and 0.25 nM in run 2. Samples were then incubated at room temperature for 3 hrs before being run over the IL7/CM5 chip, 10 mM glycine, pH3.0 was used to regenerate the surface for the next interaction. $IC_{50}$ values were calculated using Robosage, whereby the binding signals were converted into percentage values based around the maximum signal achieved using IL7R at 64 nM with 0 nM antibody. Results are shown in 4.7.

4.2 Binding kinetics Results

4.2.1 1A11

TABLE 4

Binding kinetics for 1A11 constructs

| Sample | ka (1/Ms) | kd (1/s) | KD (M) |
|---|---|---|---|
| 1A11 Chimera | 9.26e4 | 2.98e−4 | 3.22e−9 |
| 1A11 H0L0 | No binding seen | — | — |
| 1A11 H1L1 | No binding seen | — | — |
| 1A11 H6L6 | No binding seen | — | — |
| 1A11 H7L5 | No expression seen | — | — |
| 1A11 H3L4 | 1.77e5 | 4.64e−4 | 2.62e−9 |
| 1A11 H3L5 | 2.94e4 | 6.07e−3 | 2.07e−7 |
| 1A11 H3L9 | 4.32e4 | 1.84e−3 | 4.25e−8 |
| 1A11 H3L6 | 1.82e4 | 2.82e−3 | 1.55e−7 |
| 1A11 H4L4 | No binding seen | — | — |

TABLE 4-continued

Binding kinetics for 1A11 constructs

| Sample | ka (1/Ms) | kd (1/s) | KD (M) |
|---|---|---|---|
| 1A11 H6L4 | No binding seen | — | — |
| 1A11 H7L4 | No expression seen | — | — |
| Biotin-labelled 1A11 H3L4 | 1.69e5 | 4.52e−4 | 2.67e−9 |
| 1A11 H3L4Fc | 1.8e5 | 6.62e−4 | 3.68e−9 |

4.2.2 6A3

TABLE 5

Binding kinetics for 6A3 constructs

| Sample | ka (1/Ms) | kd (1/s) | KD (M) |
|---|---|---|---|
| H4-61_6L27 | 1.6e4 | 2.99e−4 | 19 |
| H4-61_7L27 | 3.77e4 | 1.04e−3 | 28 |
| H4-61_8L27 | 2.43e4 | 3.7e−4 | 15 |
| H4-61_9L27 | 6.99e4 | 1.22e−3 | 18 |

4.2.3 Selection of Various Anti-IL7R 1A11 H3L4 CDRH3 Variants of 1A11 H3L4 by BIACORE™ Analysis

TABLE 6

Proteon analysis of anti-IL-7R 1A11 H3L4 CDRH3 variants (KD, in nM)

| Amino Acid positions within 1A11 H3L4 CDRH3 | CDRH3 | | | | | | | | | |
|---|---|---|---|---|---|---|---|---|---|---|
| | G95 | D96 | G97 | N98 | Y99 | W100 | Y100a | F100b | D101 | V102 |
| Ala | 0.30 | 14.60 | 0.18 | 0.23 | 0.21 | 5.75 | 0.20 | 0.17 | 0.76 | 0.13 |
| Cys | 1.16 | 1.97 | 1.34 | 0.24 | 2.74 | 40.90 | 0.32 | 0.06 | 0.94 | 0.15 |
| Asp | 2.48 | Parental | 0.35 | 0.03 | 0.39 | Poor Binder | 0.26 | 0.08 | Parental | 0.10 |
| Glu | 2.06 | 0.16 | 2.28 | 0.05 | 0.39 | Poor Binder | 0.88 | 0.04 | 0.44 | 0.10 |
| Phe | 2.18 | 19.20 | 1.51 | 0.48 | 0.15 | 9.61 | 0.48 | Parental | 1.25 | 0.10 |
| Gly | Parental | 30.40 | Parental | 0.18 | 0.52 | 11.50 | 0.89 | 0.24 | 1.00 | 0.10 |
| His | 0.63 | 3.05 | 1.66 | 0.24 | 0.41 | 12.20 | 0.23 | 0.06 | 0.85 | 0.18 |
| Iso | Not present | 4.73 | 0.21 | 0.37 | 0.93 | Poor Binder | 0.20 | 0.06 | 0.71 | 0.09 |
| Lys | | 25.70 | 2.27 | Not present | 4.64 | 7.97 | 2.34 | 0.07 | 1.24 | 0.25 |
| Leu | 2.14 | 2.67 | 1.08 | | 2.42 | 3.38 | 0.44 | 0.15 | 0.92 | 0.33 |
| Met | 0.82 | 7.81 | 2.26 | 0.27 | 1.70 | 10.60 | 0.17 | 0.06 | 0.89 | 0.08 |
| Asn | 2.44 | 0.46 | 0.43 | Parental | 1.50 | 10.90 | 0.09 | 0.14 | 0.41 | 0.14 |
| Pro | 6.92 | 6.84 | 0.19 | 5.38 | 6.90 | Poor Binder | 1.24 | 0.90 | 0.26 | 0.71 |
| Gln | 3.02 | 1.21 | 2.07 | 0.30 | 1.31 | 12.80 | 0.68 | 0.07 | 0.74 | 0.25 |
| Arg | 29.50 | 15.70 | 2.06 | No Binding | 3.26 | Poor Binder | 2.55 | 3.49 | 0.95 | 0.31 |
| Ser | 0.79 | 3.76 | 0.53 | 0.10 | 0.25 | 10.40 | 0.46 | 0.10 | 0.60 | 0.08 |
| Thr | 3.29 | 2.32 | 0.28 | 0.10 | 1.11 | Poor Binder | 0.31 | 0.14 | 0.49 | 0.10 |
| Val | 2.36 | 3.72 | 0.08 | Not present | 1.65 | Poor Binder | 0.17 | 0.05 | 0.59 | Parental |
| Trp | | 15.80 | 4.96 | 0.52 | 0.31 | Parental | 1.73 | 0.44 | 1.50 | 0.07 |
| Tyr | | 21.90 | 1.31 | 0.71 | Parental | 8.67 | Parental | 0.26 | 1.18 | No Binding |

▨ CDRH3 variants with improved binding affinity for IL7R
■ Not present
Representative KD value for 1A11 H3L4 = 0.116 nM

TABLE 7

Selected CDRH3 variant mAbs constructed and expressed

| Antibody ID | Alternative names | Batch No. | Molecule description | DNA sequence ID No. | Protein sequence ID No. |
|---|---|---|---|---|---|
| BPC4398 | 1A11 H3L4 N98D | HEK1023 | H chain: Anti-human IL7R 1A11 VH3 N98D | 120 | 121 |

TABLE 7-continued

Selected CDRH3 variant mAbs constructed and expressed

| Antibody ID | Alternative names | Batch No. | Molecule description | DNA sequence ID No. | Protein sequence ID No. |
|---|---|---|---|---|---|
| | (CDRH3 variant) | | L chain: Anti-human IL7R 1A11 VL4 | 108 | 22 |
| BPC4399 | 1A11 H3L4 N98E (CDRH3 variant) | HEK1024 | H chain: Anti-human IL7R 1A11 VH3 N98E | 122 | 123 |
| | | | L chain: Anti-human IL7R 1A11 VL4 | 108 | 22 |
| BPC4400 | 1A11 H3L4 F100bE (CDRH3 variant) | HEK1025 | H chain: Anti-human IL7R 1A11 VH3 F100bE | 124 | 125 |
| | | | L chain: Anti-human IL7R 1A11 VL4 | 108 | 22 |
| BPC4401 | 1A11 H3L4 F100bH (CDRH3 variant) | HEK1026 | H chain: Anti-human IL7R 1A11 VH3 F100bH | 126 | 127 |
| | | | L chain: Anti-human IL7R 1A11 VL4 | 108 | 22 |
| BPC4402 | 1A11 H3L4 F100bI (CDRH3 variant) | HEK1027 | H chain: Anti-human IL7R 1A11 VH3 F100bI | 128 | 129 |
| | | | L chain: Anti-human IL7R 1A11 VL4 | 108 | 22 |
| BPC4403 | 1A11 H3L4 F100bV (CDRH3 variant) | HEK1028 | H chain: Anti-human IL7R 1A11 VH3 F100bV | 130 | 131 |
| | | | L chain: Anti-human IL7R 1A11 VL4 | 108 | 22 |
| BPC1142 | 1A11 H3L4 | HEK1029 GRITS37988 | H chain: Anti-human IL7R 1A11 VH3 | 13 | 32 |
| | | | L chain: Anti-human IL7R 1A11 VL4 | 108 | 22 |

4.2.4 BIACORE™ T100 Analysis of Selected 1A11 H3L4 CDRH3 Variants

Table 8 shows the data obtained from the 4.1.1.1 study, which shows that all the CDRH3 mutations appeared to have better affinities than the parental molecules with the best construct appearing to be BPC4398 (Anti-IL7R 1A11 H3L4 N98D).

TABLE 8

| Molecule identifier/number | Molecule description | ka (M/s) | Kd (1/s) | KD (nM) |
|---|---|---|---|---|
| BPC1142 (GRITS37988) Replicate 1 | Anti-IL7R 1A11 H3L4 | 1.08E+06 | 7.06E−05 | 0.065 |
| BPC1142 (GRITS37988) Replicate 2 | Anti-IL7R 1A11 H3L4 | 1.12E+06 | 5.86E−05 | 0.052 |
| BPC4398 | Anti-IL7R 1A11 H3L4 N98D (CDRH3 variant) | 1.71E+06 | 3.70E−05 | 0.022 |
| BPC4399 | Anti-IL7R 1A11 H3L4 N98E (CDRH3 variant) | 1.45E+06 | 4.08E−05 | 0.028 |
| BPC4400 | Anti-IL7R 1A11 H3L4 F100bE (CDRH3 variant) | 9.24E+05 | 2.68E−05 | 0.029 |
| BPC4401 | Anti-IL7R 1A11 H3L4 F100bH (CDRH3 variant) | 9.10E+05 | 3.06E−05 | 0.034 |
| BPC4402 | Anti-IL7R 1A11 H3L4 F100bI (CDRH3 variant) | 8.26E+05 | 3.32E−05 | 0.040 |
| BPC4403 | Anti-IL7R 1A11 H3L4 F100bV (CDRH3 variant) | 8.47E+05 | 3.30E−05 | 0.039 |
| BPC1142 (HEK1029) | Anti-IL7R 1A11 H3L4 | 1.16E+06 | 6.48E−05 | 0.056 |

The parental molecule (BPC1142-anti-IL7R 1A11 H3L4) was run multiple times within the experiment using CHO expressed material (GRITS37988)) and HEK expressed material (HEK1029), no significant difference was seen between affinities for the different expression systems for the parental molecule.

4.2.5 BIACORE™ 3000 Analysis of Selected 1A11 H3L4 CDHR3 Variants

Table 9 shows the data obtained from the 4.1.1.2 study and shows that all the CDRH3 mutations appeared to have better affinities than the parental molecules with the best constructs appearing to be BPC4398 (1A11 H3L4 N98D) and BPC4399 (1A11 H3L4 N98E).

TABLE 9

| Molecule identifier/number | Molecule description | ka (M/s) | kd (1/s) | KD (nM) |
|---|---|---|---|---|
| BPC1142 (GRITS37988) Replicate 1 | Anti-IL7R 1A11 H3L4 | 3.60E+05 | 2.70E−04 | 0.751 |
| BPC1142 (GRITS37988) Replicate 2 | Anti-IL7R 1A11 H3L4 | 3.62E+05 | 2.36E−04 | 0.651 |
| BPC4398 | Anti-IL7R 1A11 H3L4 N98D (CDRH3 variant) | 5.44E+05 | 2.09E−04 | 0.385 |

TABLE 9-continued

| Molecule identifier/number | Molecule description | ka (M/s) | kd(1/s) | KD (nM) |
|---|---|---|---|---|
| BPC4399 | Anti-IL7R 1A11 H3L4 N98E (CDRH3 variant) | 5.97E+05 | 2.33E−04 | 0.39 |
| BPC4400 | Anti-IL7R 1A11 H3L4 F100bE (CDRH3 variant) | 3.51E+05 | 1.91E−04 | 0.546 |
| BPC4401 | Anti-IL7R 1A11 H3L4 F100bH (CDRH3 variant) | 3.37E+05 | 1.96E−04 | 0.582 |
| BPC4402 | Anti-IL7R 1A11 H3L4 F100bI (CDRH3 variant) | 3.00E+05 | 2.00E−04 | 0.668 |
| BPC4403 | Anti-IL7R 1A11 H3L4 F100bV (CDRH3 variant) | 2.98E+05 | 1.89E−04 | 0.636 |
| BPC1142 (HEK1029) | Anti-IL7R 1A11 H3L4 | 3.49E+05 | 2.29E−04 | 0.656 |

The parental molecule (BPC1142-anti-IL7R 1A11 H3L4) was run multiple times within the experiment using CHO expressed material (GRITS37988) and HEK expressed material (HEK1029), no significant difference was seen between affinities for the different expression systems for the parental molecule.

Differences were seen in the overall affinities calculated between the two methods. This is likely to be due to the fact that IL7R is a homodimer and therefore the amount of avidity and cross linking of the antibodies with the antigen may increase or decrease dependent on the different densities of IL7R immobilised by the different capture surfaces used in the two assays. Despite the different affinities seen between the two runs the ranking in the two experiments shows that BPC4398 (1A11 H3L4 N98D) has an improved affinity over the parental molecule 1A11 H3L4.

4.3 Species Cross-Reactivity

1A11 H3L4 (wild type) was observed to cross react with marmoset and cynomolgus IL-7R tested at a comparable level by BIACORE™ system (Table 10).

TABLE 10

1A11 H3L4 with Human IL7R, Mouse IL7R and Cynomolgus IL7R Comparison

| Sample | ka (1/Ms) | kd (1/s) | KD (M) |
|---|---|---|---|
| 1A11 H3L4 with Human IL7R | 1.77e5 | 4.64e−4 | 2.62e−9 |
| 1A11 H3L4 with Cynomolgus IL7R | 2.58e4 | 2.34e−4 | 9.06e−9 |
| 1A11 H3L4 with Marmoset IL7R | 4.93e4 | 2.99e−4 | 6.05e−9 |

4.4 Epitope Binding by X-Ray Crystallography

Using a 1A11 H3L4 Fab, X-ray crystallography coupled with in silico modelling was used to predict binding interfaces for the mAbs to help provide mechanistic insight into the functional neutralization observed, and to make rational choices for antibody maturation. A high resolution (2.08A) structure of 1A11 H3L4 Fab/human IL7 receptor complex was established. Human IL7 Receptor extracellular domain and 1A11 H3L4 were expressed in CHO lec cells and purified by affinity chromatography and size exclusion chromatography. The Fab fragment of 1A11 H3L4 was generated by papain cleavage. Fab1A11H3L4/IL7R ECD complex was generated by mixing 1:1.2 molar ratio of Fab1A11H3L4 with IL7Receptor ECD. Proteins were concentrated and crystallized using the hanging drop vapor diffusion method. X-ray diffraction data were collected at the Advanced Photon Source in the Argonne National Laboratory. Diffraction data were indexed and scaled using the HKL2000 software. The structure was determined by molecular replacement in the program X-PLOR. The initial molecular replacement solution was subject to multiple rounds of molecular dynamics refinement in CNX and rebuilding with the program Win-Coot.

Based on the high resolution 2.08A crystal structure, it is predicted that 1A11 H3L4 binds IL7 Receptor at 4 of the IL-7R extracellular loops, thereby blocking IL7-ligand binding:

Loop 2: 55Gly 56Ala 57Leu 58Val 59Glu 60Val 61 Lys
Loop 3: 80Leu 81Leu 8211e 83Gly 84Lys 100Lys
Loop 4: 138Lys 139Tyr 142Val
Loop 5: 192Tyr 193Phe These findings are consistent with the observed competition for binding to hIL7 observed between 1A11 and 6A3.

4.5 Analysis of Effector Functions

4.5.1 1A11 H3L4 Lacks Complement-Mediate Cytotoxicity

A total of six separate experiments showed that 1A11 H3L4 (wild type) had no measurable complement-mediated cytotoxicity. These experiments were performed with a hIL-7r BacMam transduced HEK 293 MSR II cell line used as the target. These cells were transduced (moi 75) for ~21 hours at 37° C., 5% $CO_2$ in T175 culture flasks. The adherent cells were then removed from the flasks using TrypLE and washed several times before plating at $1 \times 10^5$ cells/50 μl/well into a 96-well plate. 25 μl of antibody was added for 30 minutes at 37° C., 5% $CO_2$. Following this incubation, 20 μl of rabbit complement was added and the plate and then returned to the incubator for 2 hours. An assessment of cell viability was carried out by adding 100 μl of CellTiter-Glo to each well with gentle mixing using a multichannel pipet. The plate was then read for luminescence signal on a Victor V plate reader (viable cells have increased signal). An example of one of those experiments is shown in FIG. 1.

The positive control antibody (Grits 32092) used in the above experiment was specific towards a cell-surface receptor for HER3 that was co-expressed on the same target cell which expressed the hIL-7Rα. This control antibody was used at the same concentration as 1A11 H3L4 (10 μg/ml), and was combined with the same two sources of rabbit complement (Calbiochem and Invitrogen). These results showed that both the target cells and complement which were used in the assay were able to induce complement dependent cytotoxicity.

4.5.2 1A11 H3L4Fc has Reduced Antibody Dependent Cell-Mediated Cytotoxicity (ADCC)

Purified peripheral blood mononuclear cells from seven human donors were profiled as effector cells in an ADCC assay. These experiments were performed with a hIL-7r BacMam transduced HEK 293 MSR II cell line used as the target cell. These cells were transduced (moi 75) for ~21 hours at 37° C., 5% $CO_2$ in T175 culture flasks. These adherent cells were then removed from the flasks using Tryple and washed several times before "loading" with europium. These loaded cells were combined into a 96-well plate (2×10⁴ cells/25 ul/well) which contained anti-IL-7R antibody for 30 minutes at 37° C., 5% CO$_2$. After incubation, effector cells were added at ratios of 200, 100, 50 and 25:1 (100 µl/well) and returned to 37° C., 5% CO$_2$ for 2 hours. Following this incubation, 25 µl of supernatant was removed and added to a 96-well plate containing 100 µl/well of Delfia enhancement solution. The plate was then incubated on a room temperature plate shaker for 5 minutes and then read in a Victor V plate reader. Any europium released by lysed cells into the surrounding supernatant (cell cytotoxicity) was measured as fluorescent units.

Figure 2:
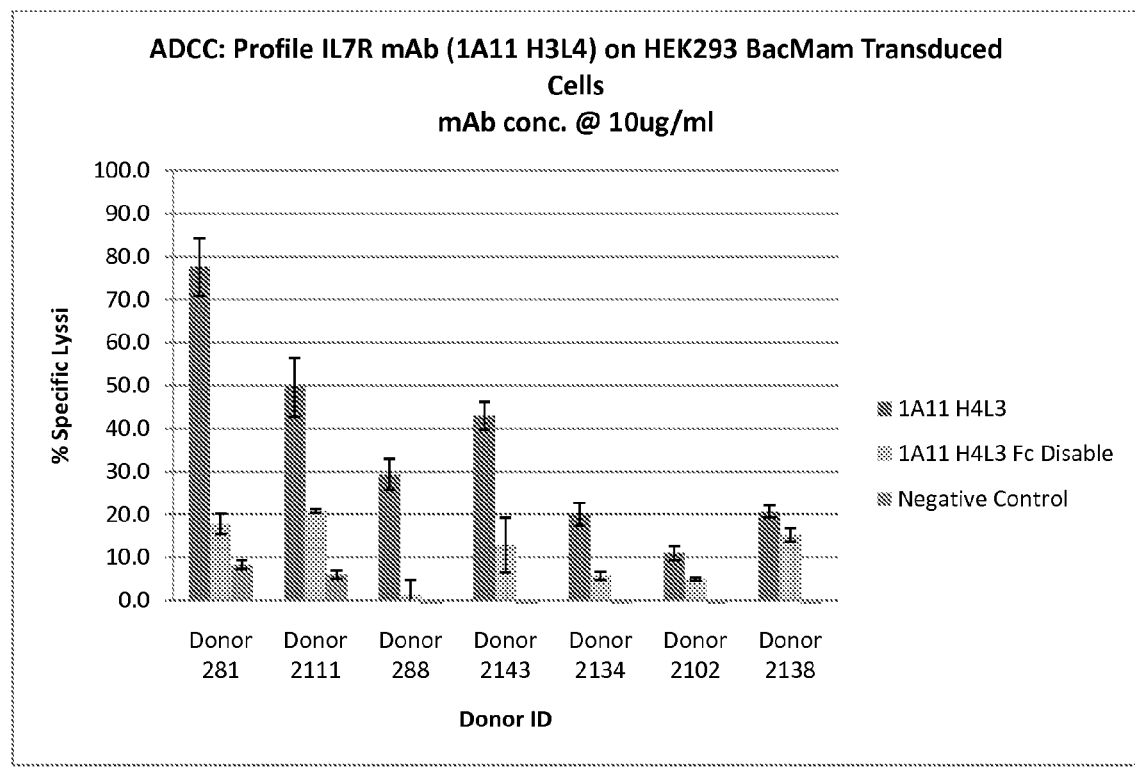
FIG. 2 shows the antibody dependent cell-mediated cytotoxicity of the humanised anti-IL7R mAb 1A11 H3L4 and the Fc-disabled anti-IL7R mAb (1A11 H3L4Fc) on HEK293 cells expressing hIL-7R, in the presence of peripheral blood mononuclear cells.

These assays compared the ability of "wild-type" 1A11 H3L4 and the Fc-disabled molecule 1A11 H3L4Fc to bind human effector cells via their Fc receptors, and kill IL-7 receptor positive target cells. The overall results from these experiments showed that the Fc-disabled 1A11 H3L4Fc was at least 2-fold less potent in initiating antibody dependent cell-mediated cytotoxicity than "wild-type" 1A11 H3L4. These results also showed that in six out of seven donors the disabled antibody was capable of inducing some level of ADCC activity (one donor showed little activity with both wild-type and disabled 1A11 H3L4). The results are shown in FIG. 2.

4.5.3 Fc Receptor Binding

1A11 H3L4 and 1A11 H3L4Fc were assessed for their ability to bind to multiple Fc effector receptors (Fc Gamma I, IIa and IIIa), and FcRn of numerous species and compared to control wild-type and Fc disabled antibodies. The work was carried out on the ProteOn XPR36 surface plasmon resonance machine (BioRad). The antibodies to be tested were coupled to a GLM biosensor chip by primary amine coupling. The various Fcγ receptors were used as analytes at 2048 nM, 512 nM, 128 nM, 32 nM and 8 nM using HBS-EP (pH7.4) as running buffer. For FcRn receptor binding, human, cyno, mouse and rat FcRn were used as analyte at 2048 nM, 512 nM, 128 nM, 32 nM and 8 nM, with the run being carried out at pH6.0 and pH7.4. All binding sensograms were double referenced with a 0 nM injection (i.e. buffer alone). The data was fitted to the Equilibrium model inherent to the ProteOn analysis software.

Table 11 shows the affinities generated for the antibody binding to the various Fc receptors assessed in this study, and shows that 1A11 H3L4 and 1A11 H3L4Fc behaved in a comparable manner to their control antibody counterparts. The disabled Fc antibodies (1A11 H3L4Fc) showed either no binding or a much reduced binding for Fcγ receptors and hence accurate analysis could not be carried out. The data for FcRn binding showed that the Fc disabled and Fc wild type had similar affinities for all species tested, the data in the table is for the pH6.0 assay, binding was either absent or much reduced at pH7.4 as expected.

TABLE 11

Binding affinities of 1A11 H3L4 (Fc disabled and wt Fc) to Fc Receptors (nM)

| Constructs | Fcγ2a (Arg) | Fcγ2a (His) | Fcγ3a (Phe) | Fcγ (Val) | Fcγ1 | Human FcRn | Cyno FcRn | Mouse FcRn | rat FcRn |
|---|---|---|---|---|---|---|---|---|---|
| Control Ab (Fc WT) | 1290 | 1500 | 1840 | 442 | 14.9 | 95 | 156 | 160 | 112 |
| Control Ab (Fc disabled) | Much Reduced Binding | no binding | no binding | no binding | Much Reduced Binding | 154 | 195 | 171 | 118 |
| 1A11 H3L4 | 1250 | 1040 | 990 | 319 | 21.4 | 183 | 210 | 192 | 145 |
| 1A11 H3L4Fc | Much Reduced Binding | no binding | no binding | no binding | Much Reduced Binding | 158 | 248 | 207 | 163 |

4.6 In Vitro Potency Assays

4.6.1 Inhibition of IL-7 Stimulated STAT5 Phosphorylation by 1A11 and 1A11 H3L4

For screening functional antibody to IL-7Rα, hybridoma culture medium, positive control antibody or testing supernatant samples were incubated with PBMC cells for 30 mins before stimulating with IL-7. The untreated cells were analyzed as the background signal, while IL-7 treated cells were set as negative control. After 30 mins incubation with the controls or testing samples, the cells were stimulated with IL-7 for 15 mins at 37° C. Cells then were fixed 1.6% of paraformaldehyde/PBS for 10 min at 37° C. and were permeabilized in 100% methanol for 20-30 mins. Cells then were washed twice in stain buffer (1% BSA in PBS) and stained with Alexa-647 labelled anti-pStat5 antibody (BD Biosciences Inc #612599) for 1 hr. Samples were analyzed on BD LSR II FACS instrument.

Figure 3A:
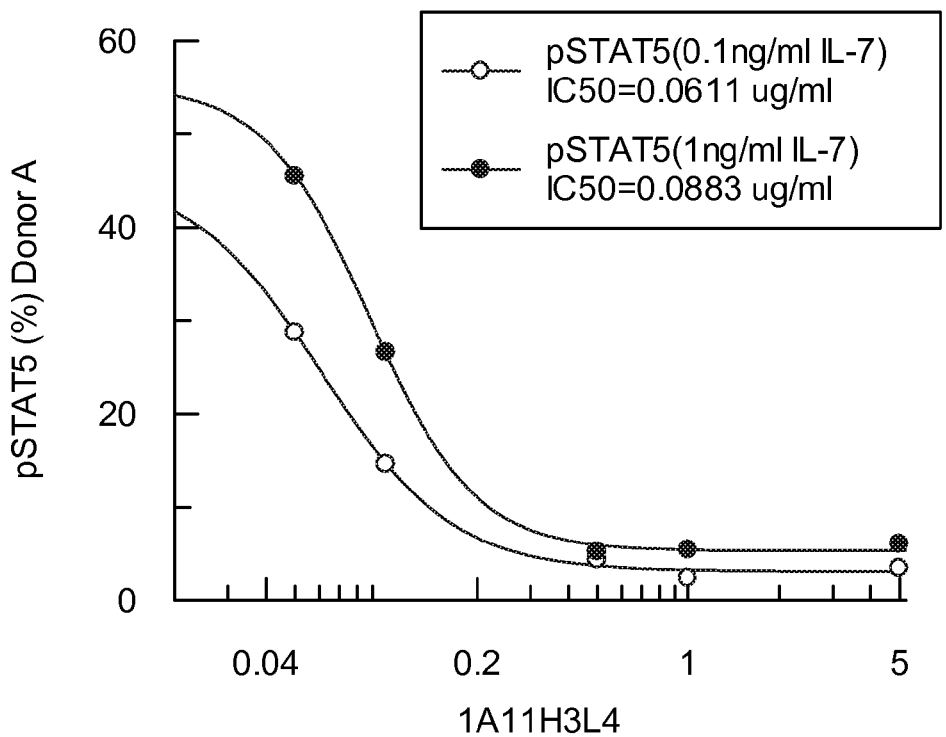
FIGS. 3A and 3B show the inhibition of IL-7-induced STAT5 phosphorylation by 1A11 H3L4 in human PBMC provided by two separate donors.
Figure 3B:
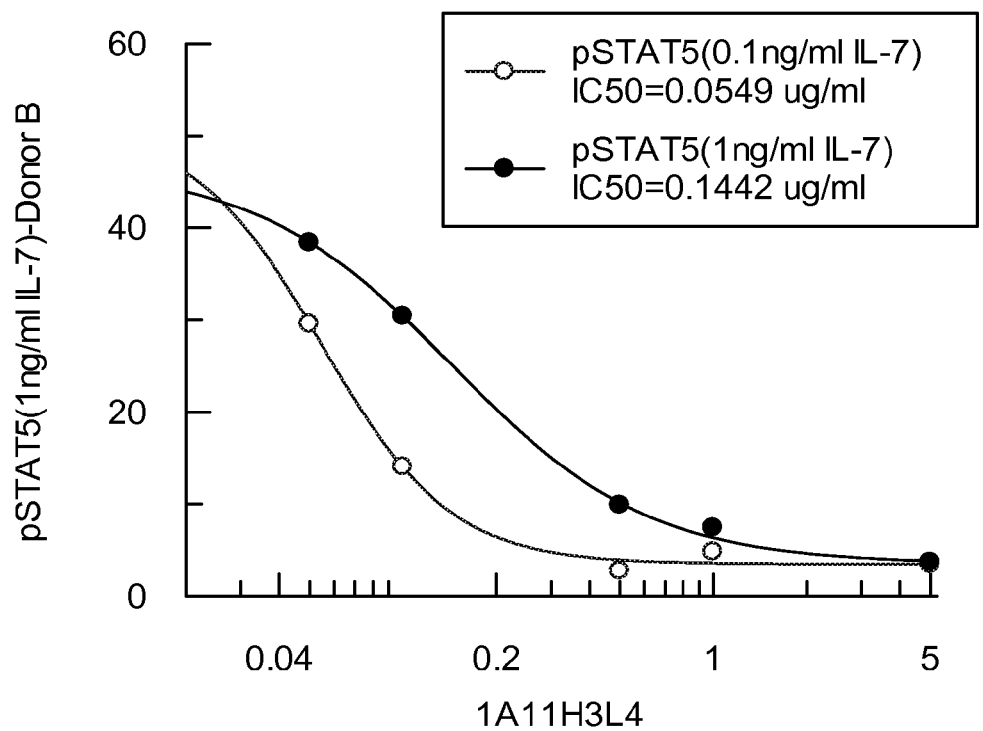
Figures 5A, 5B, 5C, 5D, 5E:
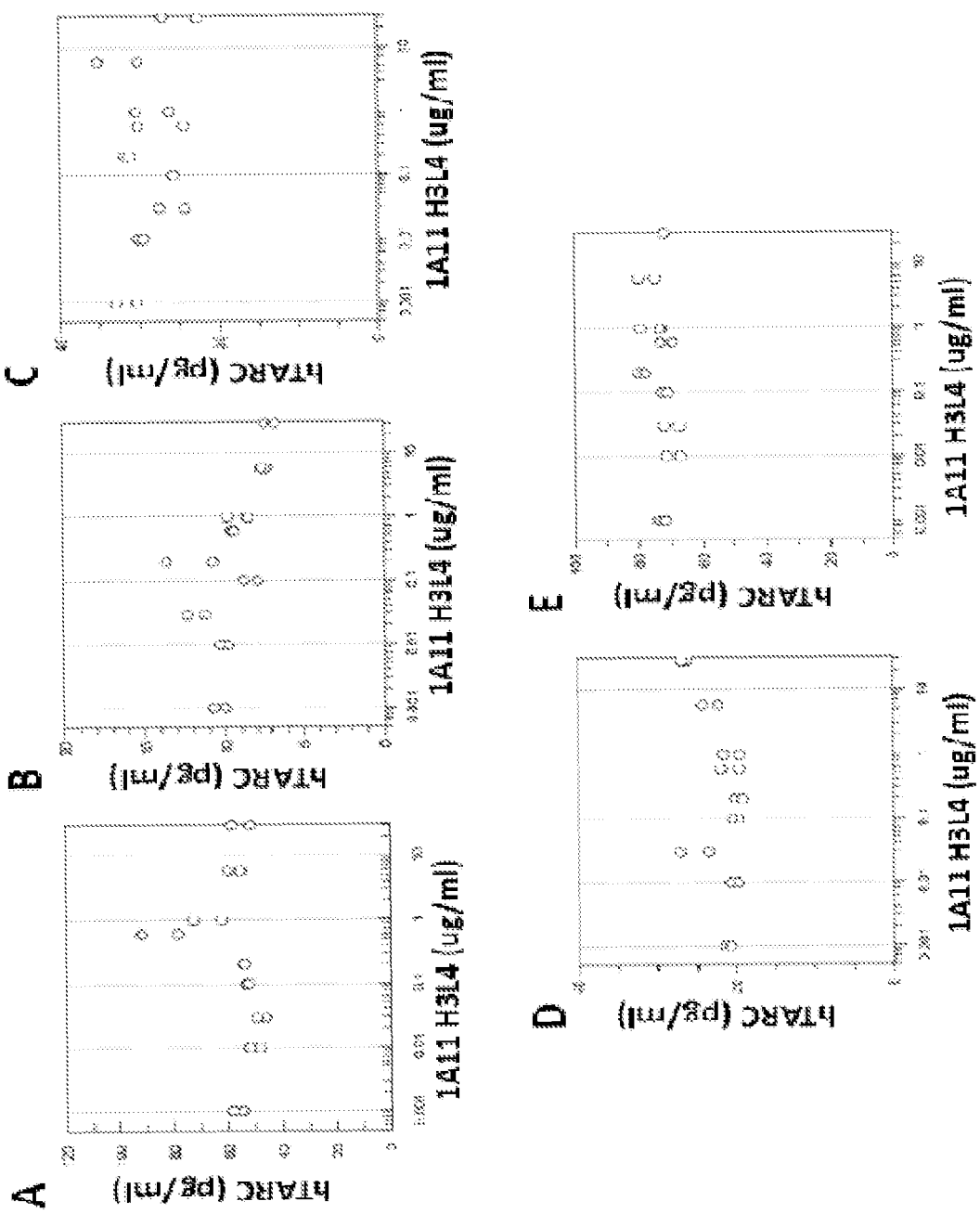
FIGS. 5A to 5E show that 1A11 H3L4 does not affect TSLP-induction of TARC (thymus and activation-regulated chemokine).

The parental 1A11 monoclonal antibody blocks IL-7 induction of STAT5 phosphorylation in human PBMC with an IC50 of 0.088 ug/ml (data not shown). 1A11 H3L4 was tested in the same assay using PBMCs from two donors at two human IL-7 concentrations (0.1 ng/ml and 1 ng/ml). 1A11 H3L4 demonstrated a very similar IC50 (average=0.087 ug/ml) compared to 1A11 indicating that the humanization process did not affect the ability of the antibody to inhibit IL-7-induced pSTAT5 (FIGS. 3A and 3B).

4.6.2 Inhibition of IL-7-Induced IL-17 Production by 1A11 H3L4

1A11 H3L4 was assayed according to the following protocol, to determine its ability to inhibit Th17 expansion. CD4+ cells were isolated according to the manual (#130-091-155, Miltenyi). Approximately 1×10⁶/ml of the CD4+ cells in 100 µl were mixed with equal volume of a 2× concentration of Th17 differentiation medium (2 µg/ml anti-CD28+10 µg/ml anti-IFN-γ+10 µg/ml anti-IL-4+12.5ng/ml IL-1β+20 ng/ml IL-23+50 ng/ml IL-6) and cultured in 37° C. with 5% CO$_2$ for 5 days. Treatment by the various cytokines and growth factors in the Th17 medium preferentially differentiated the CD4+ cells into Th17 cells. CCR6+ cells from the differentiated cultured cells at day 5 were sorted using BD FACS SORP Aria II. The CCR6+ cells were then adjusted to 2×10⁶/ml for the IL-17 production assay.

To measure IL-17 and IFN-γ level, 100 µl of CCR6+ cells were pre-incubated with testing antibody for 1 h at 37° C., and then mixed with 100 µl of 10 ng/ml IL-7. The cells were cultured for 24-40 hours in 37° C. with supplement of 5% $CO_2$. IFN-γ and IL-17 levels in 100 µl of culture supernatant were measured by FlowCytomix (Bender MedSystems) at 24 h and 40 h, respectively.

1A11 H3L4 was tested in the Th17 expansion assay in a total of four human CD4+ cell samples (FIGS. 4A-D). The humanized antibody demonstrated significant inhibition of IL-17 production in two samples and trends of inhibition in the other two samples. Given the donor-to-donor variation in this assay, we conclude that 1A11 H3L4 is able to block IL-7-mediated Th17 cell expansion.

4.6.3 Effects on TSLP Signalling

The IL-7Rα subunit is shared by both the IL-7R and the TSLP receptor complex (TSLPR). The effect of 1A11 H3L4 on TSLP signaling was tested in an in vitro assay based on TSLP-induction of TARC production by human blood monocytes. A commercial anti IL-7Rα antibody, R34.34, was used as a positive control for blocking TSLP-induction of TARC. Furthermore an Fc-disabled humanized IgG1 (HuIgG1; GRITS39633) was also used as a negative control. Monocytes from 5 donors were used, with TSLP used at 1 ng/ml, 1A11 H3L4 and HuIgG1 used at doses of 0.001-30 µg/ml, and R34.34 used at 0.4, 2, and 10 µg/ml. Cell survival was also assessed by cell counting.

1A11 H3L4 did not affect TSLP-induction of TARC as shown in FIGS. 5A-E, whilst for the same 5 donors, R34.34 substantially inhibited TARC production. The humanized negative control antibody had no effect on TARC production. This data set shows that 1A11 H3L4 does not neutralize TSLP signaling in human monocytes. Therefore it is anticipated that 1A11 H3L4 is specific for neutralization of IL-7 signaling through IL-7R and does not impact upon TSLP signaling through TSLPR.

4.7 IL7 Receptor Inhibition Assay

Table 12A shows the $IC_{50}$ values obtained in run 1 and shows that all of the constructs had better $IC_{50}$ values than the best value obtained for the parental 1A11 H3L4 molecule and that the top two molecules were BPC4401 (Anti-IL7R 1A11 H3L4 F100bH) and BPC4398 (1A11 VH3 N98D L4). Table 12B shows the $IC_{50}$ values obtained in run 2, and also shows that both the constructs, BPC4401 (Anti-IL7R 1A11 H3L4 F100bH) and BPC4398 (1A11 VH3 N98D L4) had better $IC_{50}$ values than the best value obtained for the parental 1A11 H3L4 molecule. Runs 1 and 2 were carried out on separate IL7R/CM5 surfaces.

TABLE 12A

IC50s Receptor inhibition assay (Run1)

| Molecule identifier/number | Molecule description | IC50 (nM) |
|---|---|---|
| BPC1142 (GRITS37988) Replicate 1 | Anti-IL7R 1A11 H3L4 | 19.42 |
| BPC4398 | Anti-IL7R 1A11 H3L4 N98D (CDRH3 variant) | 14.94 |
| BPC4399 | Anti-IL7R 1A11 H3L4 N98E (CDRH3 variant) | 15.8 |
| BPC4400 | Anti-IL7R 1A11 H3L4 F100bE (CDRH3 variant) | 15.33 |
| BPC4401 | Anti-IL7R 1A11 H3L4 F100bH (CDRH3 variant) | 14.75 |
| BPC4402 | Anti-IL7R 1A11 H3L4 F100bI (CDRH3 variant) | 15.23 |

TABLE 12A-continued

IC50s Receptor inhibition assay (Run1)

| Molecule identifier/number | Molecule description | IC50 (nM) |
|---|---|---|
| BPC4403 | Anti-IL7R 1A11 H3L4 F100bV (CDRH3 variant) | 15.54 |
| BPC1142 (HEK1029) | Anti-IL7R 1A11 H3L4 | 16.21 |
| BPC1142 (GRITS37988) Replicate 2 | Anti-IL7R 1A11 H3L4 | 17.23 |

The parental molecule (BPC1142-anti-IL7R 1A11 H3L4) was run multiple times within the experiment using CHO expressed material (GRITS37988) and HEK expressed material (HEK1029).

TABLE 12B

IC50s Receptor inhibition assay (Run 2)

| Molecule identifier/number | Molecule description | $IC_{50}$ (nM) |
|---|---|---|
| BPC1142 (GRITS37988) Replicate 1 | 1A11 H3L4 | 16.44 |
| BPC4398 Replicate1 | 1A11 VH3 N98D L4 | 14.86 |
| BPC4401 Replicate1 | 1A11 VH3 F100bH L4 | 14.92 |
| BPC1142 (GRITS37988) Replicate 2 | 1A11 H3L4 | 16.57 |
| BPC1142 (GRITS37988) Replicate 3 | 1A11 H3L4 | 16.79 |
| BPC4398Replicate 2 | 1A11 VH3 N98D L4 | 14.17 |
| BPC4401 (Replicate 2 | 1A11 VH3 F100bH L4 | 15.15 |
| BPC1142 (GRITS37988) Replicate 4 | 1A11 H3L4 | 17.35 |

The parental molecule (BPC1142-anti-IL7R 1A11 H3L4) was run multiple times within the experiment using CHO expressed material (GRITS37988), replicate runs of BPC4398 (1A11 VH3 N98D L4) and BPC4401 (1A11 VH3 F100bH L4).

4.8 IL-7R Polymorph Binding Assay

IL-7R exists as two polymorphic forms, variant 1: Thr66-Ile128, variant 2: Ile66-Thr128. Binding of 1A11 H3L4 to both polymorphic forms was assayed. An anti-human IgG (GE Healthcare/BIACORE™ BR-1008-39) was immobilised on a CM5 chip by primary amine coupling to a level of ~9000 resonance units (RU's), 1A11 H3L4 was then captured on this surface, and IL7R passed over at 512 n, 256 n, 128 n, 64 nnM, 32 nM and 16 nM with a 0 nM injection (i.e. buffer alone) used to double reference the binding curves, regeneration of this surface was achieved using 3M MgCl2. The binding data was fitted to the 1:1 model inherent to the BIACORE™ 3000 analysis software. The run was carried out using HBS-EP as running buffer and carried out at 25° C. on the BIACORE™ 3000. Table 13 shows the data obtained and showed that 1A11 H3L4 had the same or similar binding affinity to both polymorphic variants (i.e. it binds to both polymorphs).

TABLE 13

IL-7R polymorph binding

| | | | |
|---|---|---|---|
| 1A11H3L4 with hIL7R variant1: Thr66-Ile128 | Kon (Ka) 1.52e5 | Koff (Kd) 4.15e-4 | KD 2.73e-9 |
| 1A11H3L4 with hIL7R variant2: ILE66-Thr128 | Kon (Ka) 1.46e5 | Koff (Kd) 4.56e-4 | KD 3.1e-9 |

Within this specification the invention has been described, with reference to embodiments, in a way which enables a clear and concise specification to be written. It is intended and should be appreciated that embodiments may be variously combined or separated without parting from the invention.

What is claimed is:

1. An isolated antigen-binding protein comprising a heavy chain variable region with a sequence selected from the group consisting of SEQ ID NO:11, 12, 13, 14, 15, 16, 17, 121, 123, 125, 127, 129 and 131 and a light chain variable region comprising the following complementarity determining regions:
   (i) CDRL1 as set out in SEQ ID NO:5,
   (ii) CDRL2 as set out in SEQ ID NO:6, and
   (iii) CDRL3 as set out in SEQ ID NO:7.

2. The isolated antigen-binding protein of claim 1, which comprises a heavy chain variable region of SEQ ID NO:13.

3. The isolated antigen-binding protein of claim 1, comprising a heavy chain amino acid sequence selected from the group consisting of: SEQ ID NO:114 and SEQ ID NO:118.

4. The isolated antigen-binding protein of claim 1, which comprises a heavy chain variable region amino acid sequence selected from the group consisting of: SEQ ID NO:121 and SEQ ID NO:123.

5. The isolated antigen-binding protein of claim 1, comprising a light chain variable region of SEQ ID NO:22.

6. The isolated antigen-binding protein of claim 1, comprising a light chain of SEQ ID NO:115.

7. An isolated nucleic acid molecule encoding an isolated antigen-binding protein according to claim 1.

8. An expression vector comprising a nucleic acid molecule according to claim 7.

9. An isolated host cell comprising an expression vector according to claim 8.

10. An isolated antigen-binding protein expressed by a host cell according to claim 9.

11. A method for the production of an isolated antigen-binding protein, comprising the step of culturing a host cell according to claim 9 in a medium to produce the isolated antigen-binding protein, and isolating or purifying the isolated antigen-binding protein therefrom.

12. A method according to claim 9, wherein said culturing step is performed in conditions conducive for expression of the isolated antigen-binding protein from the host cell, and secretion of the isolated antigen-binding protein from the cell.

13. A pharmaceutical composition comprising an isolated antigen-binding protein according to claim 1 and a pharmaceutically acceptable carrier or excipient.

14. A method of treating a human subject afflicted with an autoimmune or inflammatory disease, comprising the step of administering to the subject an isolated antigen-binding protein according to claim 1.

15. A method according to claim 14, wherein the autoimmune or inflammatory disease is multiple sclerosis.

16. An isolated antigen-binding protein comprising the following complementarity determining regions:
   (i) CDRH1 as set out in SEQ ID NO:2,
   (ii) CDRH2 as set out in SEQ ID NO:3,
   (iii) CDRH3 as set out in any one of SEQ ID NO:132-137,
   (iv) CDRL1 as set out in SEQ ID NO:5,
   (v) CDRL2 as set out in SEQ ID NO:6, and
   (vi) CDRL3 as set out in SEQ ID NO:7.

17. The isolated antigen-binding protein of claim 16, which comprises a light chain variable region of SEQ ID NO:22.

18. The isolated antigen-binding protein of claim 16, which comprises a heavy chain variable region of SEQ ID NO:13, with at least one substitution in the heavy chain, said substitution selected from the group consisting of: N98D, N98E, F100bE, F100bH, F100bI and F100bV.

19. The isolated antigen-binding protein according to claim 16, which comprises a heavy chain variable region selected from the group consisting of SEQ ID NO:121, 123, 125, 127, 129 and 131.

* * * * *